(12) United States Patent
Cook

(10) Patent No.: US 6,991,902 B2
(45) Date of Patent: Jan. 31, 2006

(54) NUCLEOBASE HETEROCYCLIC COMBINATORIALIZATION

(75) Inventor: Phillip Dan Cook, Escondido, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 67 days.

(21) Appl. No.: 10/087,424

(22) Filed: Mar. 1, 2002

(65) Prior Publication Data

US 2003/0003505 A1 Jan. 2, 2003

Related U.S. Application Data

(60) Continuation of application No. 09/076,983, filed on May 13, 1998, now abandoned, which is a division of application No. 08/884,873, filed on Jun. 30, 1997.

(51) Int. Cl.
*C12Q 1/68* (2006.01)

(52) U.S. Cl. .......................................... 435/6; 544/265
(58) Field of Classification Search .................... 435/6, 435/DIG. 46, DIG. 50; 536/25.3, 25.31; 544/265
See application file for complete search history.

(56) References Cited

U.S. PATENT DOCUMENTS 3,687,808 A  8/1972  Merigan, Jr. et al. ..... 195/28 N

OTHER PUBLICATIONS

Norman, T. C.; Gray, N. S.; Koh, J. T.; Schultz, P. G. "A Structure–Based Library Approach to Kinase Inhibitors" J. Am. Chem. Soc. 1996, 118, 6430–7431.*
Konings, D. A. M.; Wyatt, J. R.; Ecker, D. J.; Freier, S. M. "Deconvolution of Combinatorial Libraries for Drug Discovery: Theoretical Comparison of Pooling Strategies" J. Med. Chem. 1996, 39, 2710–2719.*
Siani, M. A.; Weininger, D.; James, C. A.; Blaney, J. M. "CHORTLES: A Method for Representing Oligomeric and Template–Based Mixtures" J. Chem. Inf. Comput. Sci. 1995, 35, 1026–1033.*
Carell, T.; Wintner, E. A.; Rebek, J. "A Solution–Phase Screening Procedure for the Isolation of Active Compounds from a Library of Molecules" Angew Chem. Int. Ed. Engl. 1994, 33(20), 2061–2064.*
Achari et al., "Facing up to Membranes: Structure/Function Relationships in Phospholipases", *Cold Spring Harbor Symp. Quant. Biol.*, 1987, 52, 441–452.
Albert, "Purine Studies. Part IV. A Search for Covalent Hydration in 8–Substituted Purines", *J. Chem. Soc. B.*, 1966, 438–441.
Albert et al., "Purine Studies. Part I. Stability to Acid and Alkali. Solubility. Ionization. Comparison with Pteridines", *J. Chem. Soc.*, 1954, 2060–2071.

Anderson et al., "t–Butyloxycarbonylamino Acids and Their Use in Peptide Synthesis", *J. Am. Chem. Soc.*, 1957, 79, 6180–6183.
Andrews et al., "Experiments on the Synthesis of Purine Nucleosides. Part XXVI. 9–D–Glucopyranosidoisoguanine", *J. Chem. Soc.*, 1949, 2490–2497.
Arantz et al., "Pyrimidine Reactions. Part XXII. The Relative Reactivities of Some Corresponding Chlori–, Bromo–, and Iodo–pyrimidines in Aminolysis", *J. Chem. Soc.*, 1971, 1889–1891.
Badger et al., "Kinetics of Reactions in heterocycles. Part XV. Reactions of 2–, 6–, or 8–Methylthio–1–, –3–, –7–, or –9–methylpurines and Related Compounds with Methoxide Ions in Methanol", *J. Chem. Soc., Perkin Trans 2*, 1976, 1176–1180.
Barany et al., "A New Amino Protecting Group Removable by Reduction. Chemistry of the Dithiasuccinoly (Dts) Function", *J. Am. Chem. Soc.*, 1977, 99(22), 7363–7365.
Bargioni, "Memorie Scientifiche E Note Practiche Originali", *Boll. Chin. Farm.*, 1935, 64, 869–871.
Barlin, "Kinetics of Reactions in Heterocycles. Part IV. The Reaction Chloropurines and their 9–Methyl Derivatives with Sodium Ethoxide Peperidine", *J. Chem. Soc. B.*, 1967, 954–958.
Barlin et al., "Nucleophilic Displacement Reactions in Aromatic Systems. Part IX. Kinetics of the Reactions of 2–, 6–, or 8–Chloro–9–methylpurine with Piperidine in Ethanol", *J. Chem. Soc.*, 1965, 5, 3017–3021.
Beaman et al., "Purine Sulfonamides", *J. Med. Chem.*, 1996, 9, 373–378.
Beaucage et al., "Advances in the Synthesis of Oligonucleotides by the Phosphoramidite Approach", *Tetrahedron*, 1992, 48(12), 2223–2311.
Bomalaski et al., "Human Extracellular Recombinant Phospholipase $A_2$ Induces an Inflammatory Response in Rabbit Joints", *J. Immunol.*, 1991, 146(11), 3904–3910.
Brady et al., "Some Novel, Acid–Labile Amine Protecting Groups", *J. Org. Chem.*, 1977, 42(1), 143–146.
Breshears et al., "Purines. VIII. The Aminolysis of Certain Chlorosubstituted Purines", *J. Am. Chem.*, 1959, 81, 3789–3792.
Bretschneider et al., "Neue Sulfonamide, 14. Mitt.: Zwei weitere Synthesen des 6–Sulfanilamido–2,4–dimethoxy–pyrimidins (Sulfadimethoxins)", *Monatsh. Chem.*, 1964, 95, 207–213.

(Continued)

*Primary Examiner*—Bennett Celsa
*Assistant Examiner*—Jon D. Epperson
(74) *Attorney, Agent, or Firm*—ISIS Patent Department

(57) ABSTRACT

Mixtures of chemical compounds are provided having antibacterial and other utility. The mixtures are formed, preferably in solution phase, from the reaction of a purine or pyrimiding heterocyclic scaffold with a set of related chemical substituients, optionally through employment of a tether moiety. Libraries formed in accordance with the invention have utility per se and are articles of commerce. They can be used to screen for pesticides, drugs and other biologically active compounds.

17 Claims, No Drawings

Bridson et al., "Conversion of Guanosine into its $N^2$–Methyl Derivative", *J. Chem. Soc., Chem. Commun.*, 1977, 447–448.

Brossmer et al., "Darstellung und Eigenschaften von 2.6–Dichlor–5–chlormethyl–pyrimidin", *Liebigs Ann. Chem.*, 1966, 692, 119–133.

Brown et al., "Simple Pyrimidines. Part XIV. The Formation and Reactions of Some Derivatives of Simple Pyrimidine-sulphonic Acids", *J. Chem. Soc.*, 1972, 522–527.

Brown et al., "Bis–s–triazolo[1,5–α:1',5'–c]pyrimidine and Some Simple Derivatives", *Aust. J. Chem.*, 1980, 33, 1147–1152.

Brown et al., "Some Pyrimidines. Part X. The Formation and Reactivity of 2–, 4–, and 5–Pyrimidinyl Sulphones and Sulphoxides", *J. Chem. Soc.*, 1967, 568–572.

Burack et al., "Role of Lateral Phase Separation in the Modulation of Phospholipase $A_2$ Activity", *Biochem.*, 1993, 32, 583–589.

Butula, "Catalytic Hydrogenation of Purines", *Liebigs Ann. Chem.*, 1969, 729, 73–82 (English summary included).

Campbell et al., "Inhibition of Phospholipase $A_2$; a Molecular Recognition Study", *J. Chem. Soc., Chem. Commun.*, 1988, 1560–1562.

Carell et al., "New promise in combinatorial chemistry: synthesis, characterization, and screening of small–molecule libraries in solution", *Chem. Biol.*, 1995, 2, 171–183.

Carpino, "Oxidative Reactions of Hydrazines. IV. Elimination of Nitrogen from 1,1–Disubstituted–2–arenesulfonhydrazides", *J. Am. Chem. Soc.*, 1957, 79, 4427–4431.

Carpino et al., "The 9–Fluorenylmethoxycarbonyl Function, a New Base–Sensitive Amino–Protecting Group", *J. Am. Chem. Soc.*, 1970, 92(19), 5748–5749.

Carpino et al., "The 9–Fluorenylmethoxycarbonyl Amino–Protecting Group", *J. Org. Chem.*, 1972, 37(22), 3404–3409.

Challis et al., "Substitution at an amino nitrogen", *The Chemistry of the Amino Group*, Patai, S. (ed.), Interscience, J. Wiley, 1968, 277–347.

Cheng et al., "Novel Solution Phase Strategy for the Synthesis of Chemical Libraries Containing Small Organic Molecules", *J. Am. Chem. Soc.*, 1996, 118, 2567–2573.

Cho et al., "The Chemical Basis for Interfacial Activation of Monomeric Phospholipases $A_2$", *J. Biol. Chem.*, 1988, 263(23), 11237–11241.

Corse et al., "An Improved Synthesis of trans–Zeatin", *Synthesis*, 1972, 618–619.

Davidson et al., "1–Stearyl, 2–Stearoylaminodeoxy Phosphatidylcholine, A Potent Reversible Inhibitor of Phospholipase $A_2$", *Biochem. Biophys. Res. Commun.*, 1986, 137(2), 587–592.

Davidson et al., "Inhibition of Phospholipase $A_2$ by "Lipocortins" and Calpactins", *J. Biol. Chem.*, 1987, 262(4), 1698–1705.

Dennis, E.A., "Phospholipases", *The Enzymes*, Boyer, P.D. (ed.), Academic Press, New York, vol. 16, 1983, 307–353.

Dornow et al., "Synthesen von Pyrazolo–pyrimidinen aus neuen Pyrazol– und Pyrimidin–Derivaten", *Chem. Ber.*, 1967, 100, 2577–2584.

Dyer et al., "Derivatives of Purinethiols. Purine Thiolcarbonates and Related Compounds", *J. Med. Chem.*, 1964, 7, 10–14.

Elion et al., "The Direct Thiation of Uracils", *J. Am. Chem. Soc.*, 1947, 69, 2138–2139.

Elion et al., "Studies on Condensed Pyrimidine Systems. XIII. Some Amino–substituted Derivatives of Guanine and 6–Thioguanine", *J. Am. Chem. Soc.*, 1956, 78, 217–220.

Elion et al., "Condensed Pyrimidine Systems. XX. Purines Related to 6–Mercaptopurine and Thioguanine", *J. Am. Chem. Soc.*, 1959, 81, 1898–1902.

Englisch et al., "Chemically Modified Oligonucleotides as Probes and Inhibitors", *Angewandte Chemie, International Edition*, 1991, 30(6), 613–722.

Franson et al., "Phospholipid metabolism by phagocytic cells. Phospholipases $A_2$ associated with rabbit polymorphonuclear leukocyte granules", *J. Lipid Res.*, 1974, 15, 380–388.

Fu et al., "Abolition of Immunosuppressive Activity of 6–Mercaptopurine and Thioguanine by 8–Phenyl Substitution", *J. Med. Chem.*, 1967, 10, 109–110.

Giner–Sorolla et al., "Synthesis and Properties of Some 6–Substituted Purines", *J. Am. Chem. Soc.*, 1958, 80, 3932–3937.

Glaser et al., "Phospholipase $A_2$ enzymes: regulation and inhibition", *TiPs Reviews*, 1992, 14, 92–98.

Gracheva et al., *Izv. Akad. Nauk. SSSR, Ser. Khim*, 1970, 420–423 (English summary included).

Grainger et al., "An enzyme caught in action: direct imaging of hydrolytic function and domain formation of phospholipase A2 in phosphatidylcholine monolayers", *FEBS Lett.*, 1989, 252(1,2), 73–82.

Hass et al., "Adamantyloxycarbonyl, a New Blocking Group, Preparation of 1–Adamantyl Chloroformate", *J. Am. Chem. Soc.*, 1966, 88(9), 1988–1992.

Hubert et al., "Thermolyse von v–Triazolyl–Derivaten", *Chem. Ber.*, 1970, 103, 3811–3816 (English summary included).

Johnson et al., "Substituent Effects in the Reaction of Sodium 4–Nitrophenoxide with 2–Bromoacetanilides", *J. Org. Chem.*, 1971, 36(14), 1921–1925.

Kajihara et al., "Reactions of Aromatic Heterocyclic N–Oxides with 2–Bromopyrimidine", *J. Chem. Soc. Japan (Nippon Kagaku Zasshi)*, 1966, 87(8), 884–887.

Keck et al., "Regiospecific Substituent Effects in 6–Substituted Purines as Measured by Proton Magnetic Resonance", *J. Org. Chem.*, 1978, 43(13), 2587–2590.

Kemp et al., "New Protective Groups for Peptide Synthesis—I The Bic Group Base and Solvent Lability of the 5–Benzisoxazolylmethyleneoxycarbonylamino Function", *Tetra. Lett.*, 1975, 4625–4628.

Kosolapoff et al., "Synthesis of Some Pyrimidylphosphonates", *J. Org. Chem.*, 1961, 26, 1895–1898.

Kroschwitz, J.I. (ed.), "Polynucleotides", *Concise Encyclopedia of Polymer Science and Engineering*, John Wiley & Sons, 1990, 858–859.

Leonard et al., "A Stereoselective Synthesis of cis–Zeatin", *J. Am. Chem. Soc.*, 1971, 93, 3056–3058.

Lewis et al., "The Preparation and Reactions of Some Simple 2,8–Disubstituted Purines and Related Derivatives", *Can. J. Chem.*, 1963, 41, 1807–1812.

Lombardo et al., "Cobra Venom Phospholipase $A_2$ Inhibition by Manoalide", *J. Biol. Chem.*, 1985, 260(12), 7234–7240.

McKay et al., "New Amine–masking Groups for Peptide Synthesis", *J. Am. Chem. Soc.*, 1957, 79, 4686–4690.

Marki et al., "Differential inhibition of human secretory and cytosolic phospholipase $A_2$", *Agents Actions*, 1993, 38, 202–211.

Martin et al., "Synthèse De Dérivés De L 'Imidazolino–[1, 2–c]Pyrimidine Et Caractérisation De Ces Produits Par Leurs Diagrammes De Poudre (Rayons X)", *Tetrahedron*, 1957, 1, 75–85 (English Abstract Only).

Matsuda et al., "Synthesis of 2– and 8–Cyanoadenosines and Their Derivatives (Nucleosides and Nucleotides. XXVII)", *Chem. Pharm. Bull.*, 1979, 27(1), 183–192.

Mautner et al., "The Synthesis and Antineoplastic Properties of Selenoguanine, Selenocytosine and Related Compounds", *J. Med. Chem.*, 1963, 6, 36–39.

Miyake et al., "The Novel Natural Product YM–26567–1 [(+)–trans–4–(3–dodecanoyl–2,4, 6–trihydroxyphenyl)–7–hydroxy–2–(4–hydroxyphenyl) chroman]: A competitive Inhibitor of Group II Phospholipase $A_2$", *J. Pharmacol. Exp. Ther.*, 1992, 263(3), 1302–1307.

Montgomery et al., "Synthesis of Potential Anticancer Agents. XI. $N^{2,6}$–Alkyl Derivatives of 2,6–Diaminopurine", *J. Am. Chem. Soc.*, 1958, 80, 404–408.

Montgomery et al., "Synthesis of Potential Anticancer Agents. III. Hydrazino Analogs of Biologically Active Purines", *J. Am. Chem. Soc.*, 1957, 79, 2185–2188.

Nagase et al., *Yakugaku Zasshi*, 1962, 82, 528–531 (English summary included).

Nagpal et al., "4β–Chloroethylaminopyrimidines and the Formation of Imidazolidino[1.2–c]Pyrimidines on Acid Treatment of 4–Bis–β–Hydroxyethylamino–Pyrimidines", *Tetra.*, 1967, 23, 1297–1304.

Noel et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.

Noell et al., "Potential Purine Antagonists. XVII. Synthesis of Some 2–Methyl–and 2–Methylthio–6,8–Disubstituted Purines", *J. Org. Chem.*, 1959, 24, 320–323.

Noell et al., "Potential Purine Antagonists. XX. The Preparation and Reactions of Some Methylthiopurines", *J. Am. Chem. Soc.*, 1959, 81, 5997–6007.

Oinuma et al., "Synthesis and Biological Evaluation of Substituted Benzenesulfonamides as Novel Potent Membrane–Bound Phospholipase $A_2$ Inhibitors", *J. Med. Chem.*, 1991, 34, 2260–2267.

Omura et al., "Synthesis of 2–Phenylaminoadenosine from Imidazole Nucleosides", *Chem. Pharm. Bull.*, 1981, 29(7), 1870–1875.

Ostresh et al., "Peptide Libraries: Determination of Relative Reaction Rates of Protected Amino Acids in Competitive Couplings", *J. Biopolymers*, 1994, 34, 1681–1689.

Pon, R. T., "Solid–Phase Supports for Oligonucleotide Synthesis", Protocols for Oligonucleotides and Analogs, Agrawal, S. (ed.), Humana Press, Totowa, NJ, 1993, Ch. 19, 465–496.

Profft et al., "Über in 2– under 6–Stellung substituierte 4–Methylpyrimidine", *Arch. Pharm. Ber. Dtsch. Pharm.*, 1962, 295(9), 649–662.

Pruzanski et al., "Enzymatic Activity and Immunoreactivity of Extracellular Phospholipase $A_2$ in Inflammatory Synovial Fluids", *Inflammation*, 1992, 16(5), 451–457.

Ragnarsson et al., "Studies on the Coupling Step in Solid Phase Peptide Synthesis. Further Competition Experiments and Attempts to Assess Formation of Ion Pairs", *J. Org. Chem.*, 1974, 39(26), 3837–3841.

Sadykov et al., "A New Synthesis of Quinuclidine", *Zh. Obshch. Khim.*, 1963, 33, 3342–3344.

Sampson et al., "Identification and Characterization of a New Gene of *Escherichia coli* K–12 Involved in Outer Membrane Permeability", *Genetics*, 1989, 122, 491–501.

Saneyoshi et al., "Synthetic Nucleosides and Nucleotides. I. On Synthesis and Properties of Several Thiocyanato Derivatives of Purines and Their Ribonucleosides", *Chem. Pharm. Bull.*, 1967, 15(7), 909–914.

Scott et al., "Interfacial Catalysis: The Mechanism of Phospholipase $A_2$", *Science*, 1990, 250, 1541–1546.

Service, "Combinatorial Chemistry Hits the Drug Market", *Science*, 1996, 272, 1266–1268.

Shepherd et al., "Sulfanilamidopyrimidines. I. 4–Sulfanilamidopyrimidines by Heterocyclic Nucleophilic Displacements", *J. Org. Chem.*, 1961, 26, 2764–2769.

Shipps et al., "Solution–Phae Generation of Tetraurea Libraries", *Bioorg. Med. Chem.*, 1996, 4(5), 655–657.

Sieber, "77. Selektive acidolytische Spaltung von Aralkyloxycarbonyl–Aminoschutzgruppen", *Helv. Chem. Acta.*, 1968, 51(4), 614–622 (English summary included).

Spiteller et al., "Darstellung verschiedener 2,6–disubstituierter 4–Sulfanil–amidopyrimidine", *Montash. Chem.*, 1961, 92, 183–192.

Stuart et al., "Pteridine Derivatives. Part IX. 2,6–Diamino–4–hydroxy–pteridine and Related Dihydropteridines", *J. Chem. Soc.*, 1964, 4769–4774.

Sutcliffe et al., "Electron Density and Orientation of Nucleophilic Substitution in the Purine Ring", *J. Org. Chem.*, 1963, 28, 1662–1666.

Tanaka et al., "A Novel Type of Phospholipase $A_2$ Inhibitor, Theilocin A1β, and Mechanism of Action", *J. Antibiotics*, 1992, 45(7), 1071–1078.

Villani et al., "The Chemistry of the Benzyl Pyridines. IV. p–(α–and β–Dimethylaminoethyl)–2–benzylpyridines and p–(β–Dimethylaminoethyl–diphenylmethane", *J. Am. Chem. Soc.*, 1954, 76, 5623–5625.

Vishwanath et al., "Edema–Inducing Activity of Phospholipase A2 Purified from Human Synovial Fluid and Inhibition by Aristolochic Acid", *Inflammation*, 1988, 12(6), 549–561.

Vloon et al., "Synthesis and Biological Properties of Side–Chain–Modified Bleomycins", *J. Med. Chem.*, 1987, 30, 20–24.

Washburn et al., "Suicide–inhibitory Bifunctionally Linked Substrates (SIBLINKS) as Phospholipase A2 Inhibitors", *J. Biol. Chem.*, 1991, 266(8), 5042–5048.

Wery et al., "Structure of recombinant human rheumatoid arthritic synovial fluid phospholipase $A_2$ at 2.2 Å resolution", *Nature*, 1991, 352, 79–82.

Yamamoto et al., "One–step Synthesis of 5'–Azido–nucleosides", *J. Chem. Soc. Perkin I*, 1980, 306–310.

Yamane et al., "Reaction of 6–Methylsulfonylpurine Riboside with Carbon Nucleophiles and the Synthesis of 6–Alkylpurine Nucleosides (Nucleosides and Nucleotides. XXIX)", *Chem. Pharm. Bull.*, 1980, 28(1), 150–156.

Yamane et al., "Introduction of Carbon Substituents into Pyrimidine and Purine Nucleosides by Sulfur Extrusion (Nucleosides and Nucleotides. XXX)", *Chem. Pharm. Bull.*, 1980, 28, 157.

Yang et al., "Studies on the status of lysine residues in phospholipase $A_2$ from *Naja naja atra* (Taiwan cobra) snake venom", *Biochem. J.*, 1989, 262, 855–860.

Yuan et al., "Synthesis and Evaluation of Phospholipid Analogues as Inhibitors of Cobra Venom Phospholipase $A_2$", *J. Am. Chem. Soc.*, 1987, 109, 8071–8081.

Yuan, J. et al., "Syntheses of Some 2–Substituted Aminobenzothiazoles", *Acta Scientiarum Naturalium*, (Beijing Daxue Zuebao, Ziran Kexueban), 1988, 24(4), 504–506 (English abstract included).

Zervas et al., "New Method in Peptide Synthesis. I. Tritylsulfenyl and *o*–Nitrophenylsulfenyl Groups as N–Protecting Groups", *J. Am. Chem. Soc.*, 1963, 85, 3660–3671.

* cited by examiner

NUCLEOBASE HETEROCYCLIC COMBINATORIALIZATION

CROSS-REFERENCE TO RELATED APPLICATIONS

This application is a continuation of application Ser. No. 09/076,983 filed May 13, 1998, now abandoned, which is a divisional of application Ser. No. 08/884,873 filed Jun. 30, 1997, each of which is incorporated herein by reference in its entirety.

FIELD OF THE INVENTION

This invention relates to the provision of nucleobase heterocyclic combinatorials comprising certain heterocyclic "scaffolds" or backbone structures for the elaboration of pluralities of different, although related compounds. Such combinatorial mixtures are particularly suited to pharmaceutical, pesticidal, industrial, chemical and other uses relating to the modulation detection or use of biological molecules or systems.

BACKGROUND OF THE INVENTION

Chemical libraries such as those provided by the present invention are useful per se and are appreciated to be valuable in and of themselves. Indeed, such libraries can be sold or leased in unaltered form. Moreover, such libraries generally possess biological activity themselves, e.g. antibacterial effect, or can be screened to provide useful compounds such as lead or ultimate drugs, pesticides, industrial chemical species and other useful materials.

The area of combinatorial chemistry has burgeoned recently to the point where it has begun to influence the course of drug discovery (Service, R. F., *Science*, 1996, 272, 1266–1268). Most of the combinatorial organic synthesis to date has involved the use of solid phase methods with a very few instances of solution phase chemistry reported. Cheng, S., et al., *J. Am. Chem. Soc.*, 1996, 118, 2567–73. In most cases, solid-phase, parallel synthesis is applied to provide pooled mixtures or discrete compounds in volumes which accommodate high-throughput bioassays. Thus far, there has been scant interest in "one-pot", essentially simultaneous functionalization of multiple sites. Ostresh, J. M., et al., *J. Biopolymers*, 1994, 34, 1681–1689; Carell, T., et al., *Chem. Biol.* 1995, 2, 171–83; and Shipps, G. W. Jr., et al., *Bioorg. Med. Chem.*, 1996, 4, 655–657.

There would be great benefit attained from the provision of combinatorial libraries which can be formed in solution phase, especially in essentially single reaction vessel reactions. Similar benefit would attend solution phase synthesis of such libraries under conditions which ensure representation in the product library of all possible reaction products formable under the reaction condition extant from the reactants selected for use. A further benefit would attend the preparation of such libraries from scaffold or backbone molecules possessing a relatively large number of derivatizable reaction sites. The present invention provides for the achievement of the foregoing goals.

SUMMARY OF THE INVENTION

It is an object of the present invention to provide predictably diverse libraries of compounds based upon certain heterocyclic scaffolds functionalized with pluralities of chemical species. The chemical species may either be bonded directly to a functionalizable atom on the heterocyclic scaffold or may be so bonded through the intermediation of a tether moiety. It is preferred that the mixtures of the present invention comprise at least six chemical compounds. It is more preferred that ten, fifteen and even more chemical compounds be so provided.

It is also preferred that such chemical compounds be provided in effective equimolarity that is, in relatively equal molar amounts. This can be accomplished in a number of ways, preferably through the techniques set forth in U.S. application Ser. No. 702,018 filed Aug. 23, 1996 and assigned to the assignee of the present application.

The heterocyclic scaffolds have at least two, and preferably three or more functionalizable atoms which can be reacted to form the compounds of the present invention. It is convenient to provide that the functionalizable atoms on the heterocyclic scaffolds be nucleophilic, so as to react with sets of electrophilic chemical compounds to form mixtures of the invention. It is also possible to provide electrophilic reaction sites on said heterocycles, especially when the same are provided on side chains and the like.

Similarly, it is preferred that the chemical substituents for reaction with the heterocyclic scaffolds be electrophilic and that the same be provided in sets of similar or related molecules so as to give rise to predictable diversity in the resulting products. Of course, when the scaffolds possess electophilic reaction sites at functionalizable atoms (or in appended tethers) the chemical subsituents may be nucleophilic. Other reaction species, e.g. species reactive via radical reactions, oxidation—reduction reactions and the like may also be so employed.

The tether moieties which may be employed in connection with the present invention are optional. That is, they may, but need not, be caused to be inserted between the chemical substituents and the heterocyclic scaffold molecules in order to provide further diversity in the resulting mixtures of compounds. It is generally preferred to provide such tethers which have one or more functionalizable atoms or sites of further reaction (in addition to means for attaching the tether to the scaffolds) so as to permit the convenient, further reaction with sets of chemical substituents. Again, it is convenient to provide the tether moieties with nucleophilic substituents so that they may react with sets of electrophilic species. Other reaction schemes are also useful.

In accordance with preferred embodiments, the heterocyclic scaffolds are possessed of pluralities of functionalizable atoms and at least some of such atoms are chemically blocked. As will be appreciated, chemical blocking groups are well known per se and the blocking and deblocking of such locations on heterocyclic scaffolds is a matter of routine. By the judicious selection of blocking species, individual, functionalizable atoms can be exposed for a specific reaction. In this way, reactions with sets of chemical substituents or with tethers, followed by reaction with chemical substituents may be easily effected. Moreover, the heterocyclic scaffolds can be reacted seriatim or on an iterative basis to give rise to predictably complex mixtures of product chemical compounds.

It is preferred that the mixtures of chemical compounds of the present invention be prepared in solution phase and, essentially, simultaneously. It is thus preferred to undertake either a single reaction or an iterative reaction series in a single reaction vessel to give rise to a complex set of reaction mixtures comprising chemical compounds of the invention. The iterative synthetic processes of the invention, which usually involve blocking and deblocking of functionalizable atoms on the heterocyclic scaffold, can take place in a single reaction vessel, in an automated system such as any of the existing types known to persons skilled in the art, or otherwise.

Other preferred embodiments of the present invention modify the heterocyclic scaffolding in one or more ways subsequent to its reaction with chemical substituent sets. Thus, such heterocycles may be either further cyclized, ring-expanded, ring-contracted, bicyclized or otherwise reacted to alter their structure, chemical properties, physical properties, or other characteristics. It will be appreciated that such further reactions will give rise to mixtures of chemical compounds having different properties from the unreacted mixtures.

A large number of heterocyclic species may be employed as scaffold molecules in the present invention. Such heterocycles will contain nitrogen, sulfur, oxygen, and potentially other elements, other than carbon and hydrogen, within a ring structure. Such scaffolds will also include at least two, preferably three, and even four, five or more functionalizable atoms such as nitrogen, hydroxyl, sulfhydryl, other nucleophiles, leaving groups and many other reactive species known to persons of ordinary skill in the art. It is preferred that such functionalizable atoms be capable of being blocked and deblocked in accordance with standard procedures so that iterative or seriatim approaches to engendering chemical diversity in the resulting product mixtures can be easily attained. The chemical substituents which are useful in the practice of the present invention are those substituents which are capable of reacting with the functionalizable atoms of the heterocyclic scaffolds or with functionalizable atoms of one or more tethers to be connected to such scaffolds. Such chemical substituents are conveniently electrophilic to react with nucleophilic species on the scaffolds or tethers, but can be nucleophilic as well or have mixed modalities.

The tether moieties as used in the present invention are viewed as optional but are frequently preferred. Such tethers are capable of reacting with one or more functionalizable atoms on the heterocyclic scaffolds and also with the chemical substituents or sets thereof. As such, the tethers will conveniently have both nucleophilic and electrophilic substituents such that they can react with both a functionalizable atom on the heterocyclic scaffold and also with sets of chemical substituents. The tethers may be straight chain, branched, cyclic, heterocyclic, or in a number of other forms, so long as they are capable of joining chemical substituents to heterocyclic scaffolds in predictable and efficient ways. These tether moieties may also be viewed in some contexts as extensions of the heterocyclic scaffolds.

In accordance with preferred embodiments of the present invention, the heterocycles used in connection with the preparation of mixtures of chemical compounds are either nucleobases, purines or pyrimidines; or are piperazines or similar nitrogenous, heterocyclic structures. It will be apparent to persons of ordinary skill in the art that the foregoing heterocycles possess a plurality of functionalizable atoms on the heterocyclic scaffolds and that they are easily modified with functional groups to provide more functionalizable atoms for reaction. It has been found that these preferred heterocyclic scaffolds are particularly useful in the practice of the invention, especially the families of purines and pyramidines.

Preferred chemical substituents for reaction with the heterocyclic scaffolds are alkyl, acyl, aryl, alkaryl, heterocyclic, carbocyclic and other species which can undergo substitution reactions with nucleophiles or other reactive species on the heterocyclic scaffolds or on tethers connected thereto. Persons of ordinary skill in the art appreciate that a wide variety of leaving groups exists, e.g. halogen, especially bromo, tosyl, mesyl and many others, which is well known for use with the chemical substituents to render them electrophilic for use in this context. All such leaving groups are contemplated hereby.

The present invention provides mixtures of at least six chemical compounds, each of which has a common heterocyclic scaffold. Each of the scaffolds has (or had, prior to reaction) at least two functionalizable atoms thereupon and is functionalized at at least one of the functionalizable atoms with a set of at least six different chemical substituents, (giving rise to the set of at least six chemical compounds.) The chemical substituents may be connected to the heterocyclic scaffolds either directly, or through the intermediation of one or more tether moieties.

In accordance with preferred embodiments, it is desired to employ as a heterocyclic scaffolds, either a purine, a pyrimidine, or a piperazine. The necleobases, purines and pyrimidines are more preferred. It is also preferred that such scaffold molecules be substituted to provide an increased number of functionalizable atoms thereupon.

While libraries in accordance with this invention can be prepared on a solid support, in microwell plates, via automation or roboties or otherwise, solution phase chemistry is greatly preferred. Indeed, the ability to accomplish the preparation of diverse libraries in solution phase is an important aspect of the invention.

It is preferred that the mixtures of the present invention contain at least about 10 chemical compounds and, more preferably, at least 15. Greater numbers of chemical compounds such as 20, 30 and even more, can also be useful for the performance of certain embodiments of this invention.

It is an embodiment of the invention to modify a mixture—a library—post preparation such as by modifying the scaffold, modifying a tether or otherwise. Such modification gives rise to a still further library. Increased diversity results. Blocking or deblocking followed by further reaction is one such modification as is alteration of the scaffold or of a tether. It is also possible to modify al or part of the sets of chemical substituents to this end.

The heterocyclic scaffold, purine, pyrimidine or piperazine in preferred embodiments, has at least two functionalizable atoms, atoms which are capable of being reacted with a set of chemical substituents to give rise to a plurality of reactions at that atom with the members of set and so to accord a mixture of chemical compounds as a product mixture. Such functionalizable atoms may be widely varied to include nitrogen, oxygen, sulfur, and other species. Such functionalizable atoms may also be alpha, to a carbonyl or in other situations where functionalization may occur in accordance with organic chemical reaction rules.

The chemical substituents which can be reacted with the functionalizable atoms of the heterocyclic scaffold can comprise any material which is capable of reacting with the chosen functionalizable atoms. For example, if the functionalizable atom on the heterocycle is a nucleophile, then it is convenient and preferred to provide the chemical substituents, in a set of differing molecules, in a form where electrophilic displacement can occur to give rise to the mixture of chemical compounds which forms the library.

Tether molecules, which are optional in the context of this invention, are molecule which are capable of reacting with a functionalizable atom on the heterocycle and which, in turn, can provide a functionalizable atom, in a different form or identity from the atom on the heterocycle. Such can react with chemical substituents in a set to give rise to chemical libraries. Again, it is convenient to provide the tether with functionalizable atoms which are nucleophilic in nature and to react the same with a set of chemical substituents which are electrophilic. As will be apparent to persons of ordinary skill in the art, it is desirable to provide the heterocyclic scaffold with more than two functionalizable atoms, such as three, four, and more. It is also preferred that such functionalizable atoms have different reaction characteristics such that they may be blocked and deblocked selectively so as to give rise to the ability to functionalize the functionalizable atoms with different reactive chemical substituents in a predicable and selectable way. The blocking or protecting groups apply to the functionalizable atoms on the heterocycle are those which can be reacted individually under predetermined reaction conditions to "free-up" the functionalizable atoms as desired for reaction with sets of chemical substituents. In this way, seriatim or iterative reaction schemes may be employed to obtain high diversity and functionality about the heterocycle. Of course, some of the functionalizable atoms on the heterocycle may be reacted with tether moieties and others not so as to improve this diversity.

While it is possible to employ the methods of the present invention and to give rise to chemical libraries in accordance with this invention with solid phase synthesis, it is greatly preferred to employ solution phase synthesis for this purpose. Solution phase synthesis is much more convenient than is solid phase synthesis, is considerably more flexible in many respects, is inexpensive, and gives rise to large quantities of product. Moreover, it is reproducible and is amenable to a wide variety of reactions. Solid phase synthetic schemes are much less flexible, efficient, convenient, and effective in this regard and it is a considerable advantage of the present methods that solution phase synthesis can be used therewith. It is also preferred that the solution phase syntheses take place essentially simultaneously such that the libraries of the invention are formed through the reaction of a set of differing, although usually related, chemical substituents with a scaffold moiety in one "pot" or set of reaction vessels.

It is preferred that the products be "normalized" in the present reactions. Thus, the different reaction rates between a particular functionalizable atom on a heterocycle and a particular member of a set of, e.g. electrophiles, can be and frequently is different from the reaction rate of other members of the set. Reacting a set of such chemical substituents with the functionalizable atom on the heterocycle would be expected to give rise to disparate molar proportions of reaction products. This disproportion can be avoided through the use of normalization procedures as disclosed in U.S. application Ser. No. 07/702,018, assigned to the assignee of the present application and incorporated herein by reference. In this regard, the relative reactivities of chemical substituents are measured versus one or more standard co-reactants, e.g. common nucleophiles, and a relative mole percentage of the chemical substituents altered to reflect, in negative proportion, the relative reactivity. The resulting product mixture will approach equimolarity which, for purposes of this invention, is defined to be within 20% of absolute equimolarity. It is still more preferred that equimolarity be achieved to within plus or minus ten mole percent of actual molarity.

It will be appreciated that one of the more significant aspects of the present invention is the ability to proceed iteratively. In this regard, all but one functionalizable atom on the heterocycle, e.g. the preferred purine, pyrimidine or piperazine, is chemically blocked and the remaining functionalizable atom reacted with a set of chemical substituents (or with a tether) to give rise to a mixture of chemical compounds or a tethered scaffold. Another functionalizable atom on the heterocycle (or tether) is then deblocked and reacted with a further set of chemical substituents, which set may be the same or different from the original set, to give rise to an increasingly complex library of chemical compounds. It is important to note that while the libraries thus provided can become quite complex, such complexity is predictable. Thus, by judicious choice of the set of chemical substituents to be reacted with any particular functionalizable atom on a heterocycle, sets of products may be prepared in which every possible reaction product is represented. This is especially true when normalization of the reaction mixtures is practiced as described herein.

The actual blocking and deblocking of various functionalizable atoms is well known to persons of ordinary skill in the art. It is assumed that such artisans will readily appreciate how to accomplish blocking and deblocking reactions under particular conditions obtaining in any given reaction scheme.

The chemical libraries prepared in accordance with the present invention, which are the mixtures of chemical compounds made available hereby, have a variety of uses. Such libraries are useful per se and, indeed, are recognized as being articles of commence. There is a market for such libraries in addition to other uses.

The libraries have pharmaceutical uses per se as well. Thus, the libraries of the present invention generally possess antibiotic effect such that either gram positive or gram negative bacteria are killed upon the application of libraries of chemical compounds in accordance with this invention. Exemplary other uses of chemical libraries prepared in accordance with the present invention include function as a laboratory reagent, as a screening reagent for the identification of pharmaceuticals, pesticides, bioactive, and other chemical species, for the identification of lead compounds for the foregoing and other uses, in diagnostics and many other commercial uses. A wide variety of other uses will be apparent to persons of ordinary skill in the art.

The field of combinatorial chemical libraries is now reasonably well advanced such that persons or ordinary skill in the art now know how to identify or otherwise screen for useful individual molecules from the libraries.

The chemical substituents that are covalently bound to the heterocyclic scaffolds of the invention can also be referred to as functional groups or as "letters." The use of such terminology reflects the fact that the different functional groups of the compounds of the invention are positioned much like letters of the alphabet, hence the term "letter." These letters can be "reactive" or "non-reactive." By "reactive," it is meant that they will interact with a target molecule in some manner, that need not but can often be predefined. By non-reactive," it is meant that they are not designed to primarily interact with a target molecule, and in fact while they may interact with the target molecule, the primary purpose of the non-reactive moieties is to impart other properties to the molecule such as, but not limited to, effecting up-take, biodistribution, metabolism or identification.

Preferred chemical substituents useful in the practice of the invention include $C_1$–$C_{10}$ alkyl and substituted alkyl; $C_2$–$C_{10}$ alkenyl and substituted alkenyl; $C_2$–$C_{10}$ alkynyl and substituted alkynyl; $C_4$–$C_7$ carbocycloalkyl and substituted carbocycloalkyl; cycloalkenyl, substituted cycloalkenyl, substituted cycloalkenyl; $C_6$–$C_{14}$ aryl and substituted aryl; heteroaryl and substituted heteroaryl; nitrogen-, oxygen-, or sulfur-containing heterocycle; substituted nitrogen-, oxygen-, or sulfur-containing heterocycle; mixed heterocycles; and substituted mixed heterocycle; where said groups for substitution are selected from alkyl, alkenyl, alkynyl, aryl, hydroxyl, alkoxy, alcohol, benzyl, nitro, thiol, thioalkyl, thioalkoxy, or halogen groups.

Other chemical substituents can be phthalimido, ether having 2 to 10 carbon atoms and 1 to 4 oxygen or sulfur atoms, metal coordination groups, conjugate groups, halogen, hydroxyl, thiol, keto, carboxyl, $NR^1R^2$, $CONR^1$, amidine $(C(=NH)NR^2R^3)$, guanidine $(NHC(=NH)NR^2R^3)$, glutamyl $(R^1OOCCH(NR^2R^3)(CH_2)_2C(=O))$, nitrate, nitro, nitrile, trifluoromethyl, trifluoromethoxy, NH-alkyl, N-dialkyl, O-aralkyl, S-aralkyl, NH-aralkyl, azido $(N_3)$, hydrazino $(NHNH_2)$, hydroxylamino $(ONH_2)$, sulfoxide (SO), sulfone $(SO_2)$, sulfide (S—), disulfide (S—S), silyl, a nucleosidic base, an amino acid side chain, a carbohydrate, a drug, or a group capable of hydrogen bonding.

In the foregoing, each $R^1$ and $R^2$ is, independently, H, alkyl or haloalkyl having 1 to about 10 carbon atoms, alkenyl having 2 to about 10 carbon atoms, alkynyl having 2 to about 10 carbon atoms, or aryl having 6 to about 14 carbon atoms; and each $R^3$ is, independently, a single bond; CH=CH; C≡C; O; S; $NR^6$; $SO_2$; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from hydroxyl (OH), alkoxy, alcohol, benzyl, phenyl, nitro $(NO_2)$, thiol (SH), thioalkoxy, halogen, alkyl, aryl, alkenyl, and alkynyl groups.

As will be appreciated, the chemical substituents are reacted with a functionalizable atom of the scaffold in sets of at least six species, preferably ten and even larger numbers. It is greatly preferred that the sets comprise species which are chemically related in some way so as to give rise to predictable diversity in the resulting products.

One illustration of this preference serves to demonstrate the principal. A series of electrophiles having primary bromine functions, a classical leaving group, can easily be prepared. For example, all of the following have been obtained or prepared using standard chemistry: N-(α-bromoacetyl)-1-aminocycloheptane(Br-$L_1$); N-(α-bromoacetyl)-m-nitroaniline(Br-$L_2$); N-(α-bromoacetyl)-p-methoxyaniline(Br-$L_3$); N-(α-Bromoacetyl)-2-aminobenzothiazole(Br-$L_4$); N-(α-Bromoacetyl)-2-aminomethylfuran(Br-$L_5$); m-chloro benzyl bromide(Br-$L_6$); m-cyanobenzylbromide(Br-$L_7$); m-nitro benzyl bromide(Br-$L_8$); m-methylesterbenzylbromide(Br-$L_9$); m-triflouromethylbenzylbromide(Br-$L_{10}$); N-(α-bromoacetyl)-3-amino-5-methylisoxazole(Br-$L_{11}$); N-(α-bromoacetyl)tetrahydroisoquinoline(Br-$L_{12}$); adamantane-1-carborbonyl chloride(Br-$L_{13}$); bromoacetonitrile(Br-$L_{14}$); propargyl bromide(Br-$L_{15}$); N-(α-bromoacetyl)-4-methyl-2-aminothiazole(Br-$L_{16}$); 2-bromoacetamide(Br-$L_{17}$); 1-bromo-2-butanone(Br-$L_{18}$); 6-(bromoacetyl)-1,2,3,4-tetrahydro-1,1,4,4-tetramethyl naphthalene(Br-$L_{19}$); 6-(Bromoacetyl)-2-oxo-1,2,3,4-tetrahydroquinoline(Br-$L_{20}$); 2-(bromoacetyl)-5-chloro-3-methylbenzo[b]thiophene (Br-$L_{21}$); 5-(bromomethyl)benzofurazan(Br-$L_{22}$); 3-(bromomethyl)-5-chlorobenzo[b]thiophene (Br-$L_{23}$); 6-(bromomethyl)-4-chloro-2-trifluoromethyl)quinoline(Br-$L_{24}$); 4-(4-bromomethylphenyl)-1,2,3-thiadiazole(Br-$L_{25}$); N-(α-bromoacetyl)-4-methyl-2-aminothiazole(Br-$L_{26}$); α-Bromo-m-xylene(Br-$L_{27}$); m-Fluoro-benzylbromide(Br-$L_{28}$); 3-(bromomethyl)-benzonitrile(Br-$L_{29}$); m-bromobenzyl bromide(Br-$L_{30}$); 2-bromo-N'-(2'-ethyl-bis-N-tert-butoxycarbonylguanidino)-acetamide(Br-$L_{31}$); N'-4'-(bromo-acetyl)-piperazino-N'-1'-(bis-N-tert-butoxy carbonyl-1-carboxamidine(Br-$L_{32}$); 2-bromo-N-(2'-ethyl-N'-tert-butoxycarbonylamino)-acetamide(Br-$L_{33}$); N-4-(bromoacetyl)-N-1-(tert-butoxycarbonyl)-piperazine(Br-$L_{34}$); benzyl bromide(Br-$L_{35}$); and cinnamyl bromide(Br-$L_{36}$). These are each referred to hereinafter by the "L" (for "Letter") number, e.g. $L_1$, $L_2$, etc. Their relative reactivity to heterocyclic (non-aromatic) nitrogen such as 1-phenyl-piperazine can be determined and sets of bromides selected and normalized for reaction with scaffold nitrogen atoms to provide effectively equimolar mixtures of products.

In the context of this invention, a heterocycle is a cyclic compound containing at least one heteroatom such as N, O, or S. A mixed heterocycle is a cyclic compound containing at least two heteroatoms such as N, O, or S. A heteroaryl compound is a heterocycle containing at least one hetero atom such as N, O, or S and is not fully saturated e.g. is in a state of partial or complete unsaturation especially if the same is aromatic. Heteroaryl is also meant to include fused systems including systems where one or more of the fused rings contain no heteroatoms.

Heterocycles, including nitrogen heterocycles, which can be used as scaffolds or as functional groups or scaffolds or as tethers include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, and carbazole groups. Piperazines and imidazole groups are especially useful.

Purines and pyrimidines suitable for use as preferred heterocycle scaffolds include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch et al., *Angewandte Chemie, International Edition* 1991, 30, 613, and in the examples hereof.

In the context of this specification, alkyl (generally $C_1$–$C_{20}$), alkenyl (generally $C_2$–$C_{20}$), and alkynyl (generally $C_2$–$C_{20}$) groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methyl-propyl, 2-methyl-4-ethylbutyl, 2,4-diethylbutyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups containing a pi bond, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Further, in the context of this invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds from about 1 to about 6 carbon atoms. A branched compound, as used herein, comprises a straight chain compound, such as an alkyl, alkenyl, alkynyl compound, which has further straight or branched chains attached to the carbon atoms of the straight chain. A cyclic compound, as used herein, refers to closed chain compounds, i.e. a ring of carbon atoms, such as an alicyclic or aromatic compound. The straight, branched, or cyclic compounds may be internally interrupted, as in alkoxy or heterocyclic compounds. In the context of this invention, internally interrupted means that the carbon chains may be interrupted with heteroatoms such as O, N, or S. However, if desired, the carbon chain may have no heteroatoms.

Useful aryl groups, generally $C_6$–$C_{20}$, include, but are not limited to substituted and unsubstituted aromatic hydrocarbyl groups. Aralkyl groups (generally $C_7$–$C_{20}$) include, but are not limited to groups having both aryl and alkyl functionalities, such as benzyl and xylyl groups. Preferred aryl and aralkyl groups include, but are not limited to phenyl, benzyl, xylyl, naphthyl, tolyl, pyrenyl, anthracyl, azulyl, phenethyl, cinnamyl, benzhydryl, and mesityl. These can be substituted or unsubstituted. It is particularly preferred that if substituted, the substitution be meta to the point of attachment of the substitution aryl or aralkyl compound to the nitrogenous moieties or to tethers connecting to the nitrogenous moieties since such meta substitution isolates electronic effects of the substituent from the reactive functionality used to attach the aromatic moiety to the nitrogenous moiety or a tether.

The aliphatic and aromatic groups as noted above may be substituted or unsubstituted. In the context of this invention, substituted or unsubstituted, means that the compounds may have any one of a variety of substituents, in replacement, for example, of one or more hydrogen atoms in the compound, or may have no substituents. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

Metal coordination groups according to the invention include, but are not limited to, carbonyl moieties, hyroxyl moieties, amine moieties, acid moieties and other more complex moieties such as hydroxamic acids, catecholamide, acetylacetone, 2,2'-bipyridine, 1,10-phenanthroline, diacetic acid, pyridine-2-carboxamide, isoalkyldiamine, thiocarbamate, oxalate, glycyl, histidyl and terpyridyl. Other metal coordination groups are also known (Mellor, D. P., *Chemistry of Chelation and Chelating Agents in International Encyclopedia of Pharmacology and Therapeutics*, Section 70, The Chelation of Heavy Metals, Levine, W. G. Ed., Pergamon Press, Elmford, N.Y., 1979).

Non-reactive functionalities used as chemical functional groups, such as groups that enhance pharmaco-dynamic properties, include groups that improve uptake and enhance resistance to enzymatic or chemical degradation. Non-reactive functionalities may also enhance pharmacokinetic properties. In the context of this invention, such groups improve uptake, distribution, metabolism or excretion. Non-reactive functionalities include, but are not limited to, alkyl chains, polyamines, ethylene glycols, steroids, polyamides, aminoalkyl chains, amphipathic moieties, and conjugate groups attached to any of the nitrogenous sites for attachment, as described above.

Conjugate groups of the invention include inter-calators, reporter molecules, polyamines, polyamides, poly ethers including polyethylene glycols, and other moieties known in the art for enhancing the pharmacodynamic properties or the pharmacokinetic properties. Typical conjugate groups include PEG groups, cholesterols, phospho-lipids, biotin, phenanthroline, phenazine, phenanthridine, anthraquinone, acridine, fluoresceins, rhodamines, coumarins, and dyes.

A number of chemical functional groups can be introduced into compounds of the invention in a blocked form and subsequently deblocked to form a final, desired compound. In general, a blocking group renders a chemical functionality of a molecule inert to specific reaction conditions and can later be removed from such functionality in a molecule without substantially damaging the remainder of the molecule (Green and Wuts, Protective Groups in Organic Synthesis, 2d edition, John Wiley & Sons, New York, 1991). Carboxyl groups can be protected as acetyl groups. Representative hydroxyl protecting groups are described by Beaucage et al., *Tetrahedron* 1992, 48, 2223. Acid-labile hydroxyl protecting groups include trityl, monomethoxy trityl, dimethoxytrityl, trimethoxytrityl, 9-phenylxanthine-9-yl (Pixyl) and 9-(p-methoxyphenyl)xanthine-9-yl (MOX). Chemical functional groups can also be "blocked" by including them in a precursor form. Thus, an azido group can be used considered as a "blocked" form of an amine since the azido group is easily converted to the amine.

Exemplary N-protecting groups are tert-butyloxycarbonyl (BOC) (Carpino, *J. Am. Chem. Soc.*, 1957, 79, 4427; McKay, et al., *J. Am. Chem. Soc.*, 1957, 79, 4686; Anderson et al., *J. Am. Chem. Soc.*, 1957, 79, 6180) and the 9-fluorenylmethyloxycarbonyl (FMOC) (Carpino et al., *J. Am. Chem. Soc.*, 1970, 92, 5748 and *J. Org. Chem.*, 1972, 37, 3404), Adoc (Hass et al., *J. Am. Chem. Soc.*, 1966, 88, 1988), Bpoc (Sieber *Helv. Chem. Acta.*, 1968, 51, 614), Mcb (Brady et al., *J. Org. Chem.*, 1977, 42, 143), Bic (Kemp et al., *Tetrahedron*, 1975, 4624), o-nitrophenylsulfenyl (Nps) (Zervas et al., *J. Am. Chem. Soc.*, 1963, 85, 3660) and dithiasuccinoyl (Dts) (Barany et al., *J. Am. Chem. Soc.*, 1977, 99, 7363) as well as other groups which are known to those skilled in the art.

In certain embodiments, compositions of the invention are prepared by intermolecular reductive coupling. In other embodiments, compounds of the invention can be prepared by intermolecular radical addition reactions. In further embodiments, compounds can be prepared by nucleophilic displacement.

In certain preferred embodiments of the invention, scaffolds are reacted with tether groups that have a further nitrogen or other heteroatom moiety thereon. The nitrogen moiety can be further reacted with a "letter" or a mixture of letters. For example nitrogenous moieties can be reacted with a group having structure $R_L$–$L_n$, thereby displacing the $R_L$ leaving group and forming a covalent -N-T-$L_n$ linkage where T-represents an optional tether and $L_m$ represents a letter or mixture of letters.

Amino nitrogenous compounds, if not directly available, can be synthesized by treating the corresponding hydroxyl-terminated compound with $Ph_3P$, $CBr_4$ and $LiN_3$ according to the procedure of Hata et al. (*J. Chem. Soc. Perkin* 1 1980, 306) to furnish a terminal azide. Reduction of the azido group with tributyltin hydride provides the desired amino functionality.

Hydroxylamino nitrogenous groups can be prepared by treating the corresponding hydroxyl compound with N-hydroxyphthalimide, triphenylphosphine and diethylazodi-carboxylate under Mitsunobu conditions to provide an O-phthalimido derivative. The free hydroxylamino compound can be generated in quantitative yield by hydrazinolysis of the O-phthalimido derivative.

Hydrazino nitrogenous compounds can be prepared by treating hydroxyl-terminated compounds with tosyl chloride in pyridine to give an O-tosylate derivative. Treatment of benzylcabazide with O-tosylate will furnish a benzylcarbazide derivative, which on hydrogenation provides the free hydrazino moiety for reductive coupling.

The hydrazino nitrogenous compound (hydrazine) synthesized as described above can be further converted to a hydrazide by reacting it with a carboxylic ester, or an acid halide in the presence of a base such as pyridine or DIEA.

Amino nitrogenous compounds (amines) may be further functionalized to form amides, hydrazides, carbamates, ureas, sulfonamides, sulfinamides and sulfanamides. An amide nitrogenous compound can be prepared by treating the amine with an acid halide, such as an acid chloride, in the presence of a base such as pyridine. Alternatively, amides can also be prepared by the action of an amine on a carboxylic ester.

Carbamates can also be synthesized from amines. The procedure involves reaction of the amine with an alkyl halide and potassium carbonate in the presence of a phase transfer catalyst such as $Bu_4NH^+$ $HSO_4^-$. Carbamates can also be obtained by the treatment of an amine with an appropriate alkyl or aryl chloroformate, or by reacting an amine with carbon monoxide, oxygen and an alcohol, in the presence of a catalyst such as pyridine.

Further, amines can be converted to ureas by reacting the amine with carbon monoxide in the presence of selenium or sulfur, or $Pd(OAc)_2$—$I_2$—$K_2CO_3$ (only for secondary amines). Also, amines can be added to isocyanates to form ureas. Symmetrically substituted ureas can be obtained by the reaction of an amine with phosgene or ethyl carbonate.

Sulfonamides can be prepared from amines by the reaction of an amine with a sulfonyl chloride in the presence of a base. Sulfinamides can be prepared by the reaction of an amine with a sulfinyl chloride in the presence of a base. The sulfonamide or sulfinamide thus formed can further be reduced to a sulfanamide by $LiAlH_4$, zinc and acetic acid or triphenylphosphine and iodine.

The nitrogen atoms of nitrogenous compounds such as amines, hydroxylamines, hydrazines, amides, carbamates, ureas, sulfonamides, sulfinamides and sulfanamides can be alkylated by treating the nitrogenous compound with a base such as sodium hydroxide or sodium hydride, and then reacting the resulting sodium salt with a halide such as the illustrative halides (benzyl bromide, 3-methylbenzyl bromide, 3-methoxybenzyl bromide or 3-nitrobenzyl bromide) used in the examples below. A wide spectrum of halides can be used for this purpose.

The above-mentioned nitrogenous compounds can also be acylated at the nitrogen atom by treating them with a base such as sodium hydroxide or sodium hydride, and then reacting the resultant sodium salt of the nitrogenous compound with an acid halide. Illustrative acid halides include, but are not limited to, benzoyl chloride, 3-methylbenzoyl chloride, 3-methoxybenzoyl chloride or 3-nitrobenzoyl chloride.

Additionally, the nitrogenous compounds can be functionalized at the nitrogen atom by reaction of the nitrogenous compound with an aldehyde or ketone forming a Schiff base. The Schiff base is then reduced in the presence of a reducing agent such as $NaCNBH_3$, sodium metal in ethanol, or organometallic compounds such as allylic boranes and allylic stannanes.

The "letters" (chemical substituents) can be selected based on chain length, i.e. short versus long, based on the use of a ring versus a linear group, use of an aromatic versus aliphatic group, use of a functionalized group versus a non-functionalized group, to mention only a few of the wide variety of letters available. Indeed simply varying functional moieties present on letters, e.g. acid, alcohol, aldehyde, amide, amine, amidine, azo, azoxy, double bond, ether, ethylene oxide, guanidine, halide, haloalkyl, hydrazine, hydroxylamine, ketone, mercaptan, nitrate, nitrile, nitro, nitroso, quaternary nitrogen, sulfide, sulfone, sulfoxide, triple bond, urea, etc. on a single backbone, e.g. a simple alkyl group, yields a vast array of diversity functions. When this is expanded to include placement of such varied functional moieties on a broad platform of backbones, e.g. a series of alkyl compounds, a series of aryl compounds, a series of alicyclic compounds, etc., the potential for a vast array of letters is apparent.

Chemical substituents, e.g. reactive "letters", for attachment to a scaffold can be are normalized. These normalized mixtures are conveniently used in simultaneous addition reactions with the scaffolds. Preferred simultaneous addition reactions are run in solution phase and are referred to as "solution phase simultaneous addition of functionality (SPSAF)" reactions. The normalization process for various sets of reactive letters is illustrated in examples 56–97. These examples employ a model system with 1-phenylpiperazine as the nucleophilic scaffold in reaction with various activated functional groups e.g. alkylating agents.

The exemplary bromides listed above were divided into five sets of five with N-(α-bromoacetyl)-2-aminobenzothiazole (Br-$L_4$) (Yuan, J., Zang, M., *Beijing DaxueXuebao, Ziran Kexueban*, 1988, 24, 504–506) common to each set. N-(α-Bromoacetyl)-2-aminobenzothiazole (Br-$L_4$) was used as a reference in each of the sets of letters used in the preparation of libraries. The reactions were performed at ambient temperature, were not moisture-sensitive, and typically the products were obtained in high yields (>95%) after simple aqueous work-up.

As illustrated in Example 81, 5 reactions were performed in order to create calibration curves for each of 5 reagents/letters ($L_1$–$L_5$). The concentrations of the products 18–22 (FIG. 3) were known, and calibration curves followed as absorbance vs. concentration plots (FIGS. 5–9). The resolution of products was performed using capillary zone electrophoresis (CZE). A plot of known concentration vs compound vs experiment was made followed by a plot of absorbance vs unknown peak vs experiment (FIG. 4). Inspection of the profiles of the two plots allowed the determination of unknown peaks in the chromatogram. The value here is that the peak identification did not require the additional labor of coinjections with authentic samples. The identity of peaks may also be determined by visual inspection of the electropherogram profiles with respect to the known concentrations. Important to the success of this calibration method was the inclusion of an internal standard to correct for experimental errors, e.g., variance of injection amounts, etc. The absorbances of the products obtained from CZE were normalized to that of the internal standard. Initially, for set 1, an internal standard (24) was synthetically prepared, thereafter, a commercially available compound, (+−)-dropropizine, was used for sets 2–5 (for the final product mixtures, internal standard may be omitted or included). Typically the calibration curves exhibited high correlations (r2>=0.99) and provided extinction coefficients (ε, slopes) and intercepts (close to zero).

The pseudo-competitive experiments were initiated taking an empirical approach, assuming that the alkylation of amines follows second order rate law, first order with respect to amine and reactant (Challis, B. C., et al., *The Chemistry of the Amino Group*, Patai, S., 1968, 277–347, Interscience, J. Wiley). Initially, a pseudo-competitive reaction was performed in which 1.0 equivalent of each alkylating agent (5 eq total), e.g., 5 and 14–17 was reacted with 1.0 equivalent of the nucleophile, 1-phenylpiperazine, to form products 22 and 31–34 (Table 3, exp 1). CZE of the reaction mixture provides the relative concentrations of products after application of the calibration curves (equation takes form of y=mx+b, where y=absorbance, m=extinction coefficient (ε), x=concentration, and b=intercept). It is noted that although there are excess reagents present within the reaction mixture, they are transparent to the CZE method as they are not charged under the given conditions (pH 3) and migrate with the electroosmotic flow. To a first approximation the relative rates of product formation are taken to be proportional to the relative concentrations of products at equilibrium, with 22 serving as a standard.

The different sets of reactants may be mixed under competitive conditions if one is guided by the kapp values, and to a first approximation uniform relative rates could be attainable. Crossover of the different sets would also require that the ε values remain relatively constant irrespective of the set. This principle appears to hold on inspection of the ε values for the standard 22 in sets 2 ($L_{4,11,12,16\ and\ 17}$), 3 ($L_{4\ and\ 18\text{-}21}$) and 4 ($L_{4\ and\ 22\text{-}25}$), (<7% variation from mean). The ε value for 22 in set 1 is significantly different from those of sets 2–4 due to the use of an alternate internal standard. To enable the crossover of different sets, reactant $L_{21}$ of set 3 was replaced with $L_{11}$ of set 2 to create set 5. The pseudo-competitive studies were carried out as mentioned for set 5, and after 3 experiments uniform relative rates were afforded based on calibration curves for set 2 (25/8) and set 3. The scheme is shown below:

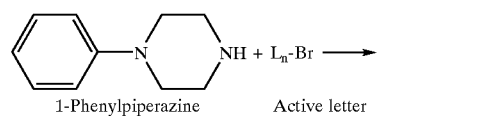

| Ex. # | Cmpd # | L# | $k_{app}$ | Ex. # | Lib. # | $L_n$ |
|---|---|---|---|---|---|---|
| 64 | 18 | 1 | 0.305 | 81 | 40 | $L_1$–$L_5$ |
| 65 | 19 | 5 | 0.347 | 81 | 41 | $L_1$–$L_5$ |
| 66 | 20 | 3 | 0.547 | 81 | 42 | $L_1$–$L_5$ |
| 67 | 21 | 2 | 0.882 | 81 | 43 | $L_1$–$L_5$ |
| 68 | 22 | 4 | 1.000 | 81 | 44 | $L_1$–$L_5$ |
| 69 | 23 | 12 | 0.312 | 82 | 45 | $L_4$, $L_{22}$–$L_{25}$ |
| 70 | 24 | 17 | 0.235 | 83 | 46 | $L_1$–$L_5$ |
| 71 | 25 | 11 | 0.831 | 84 | 47 | $L_1$–$L_5$ |
| 72 | 26 | 16 | 0.927 | 85 | 48 | $L_4$, $L_{11}$, $L_{12}$, $L_{16}$ and $L_1$ |
| 73 | 27 | 18 | 1.099 | 86 | 49 | $L_4$, $L_{22}$–$L_{25}$ |
| 74 | 28 | 19 | 1.204 | 87 | 50 | $L_2$, $L_4$, $L_{10}$, $L_{11}$ and $L_{19}$ |

-continued

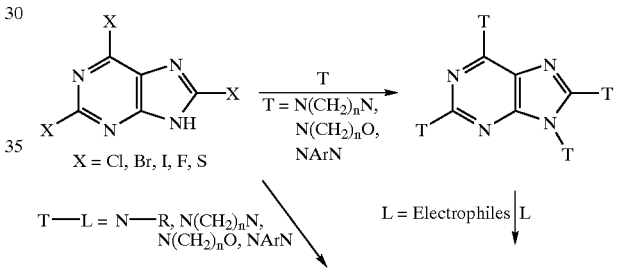

| Ex. # | Cmpd # | L# | $k_{app}$ | Ex. # | Lib. # | $L_n$ |
|---|---|---|---|---|---|---|
| 75 | 29 | 20 | 1.232 | | | |
| 76 | 30 | 21 | | | | |
| 77 | 31 | 22 | 0.425 | | | |
| 78 | 32 | 23 | 0.387 | | | |
| 79 | 33 | 24 | 0.446 | | | |
| 80 | 34 | 25 | 0.364 | | | |

In one aspect of the present invention, purines having halogen or thio substituents are treated with sets of chemical substituents under conditions effective to displace halogen with letters having optional tethers. The general reaction scheme followed by representative reactions are shown below:

A tabular example of this, using pheylpiperazine

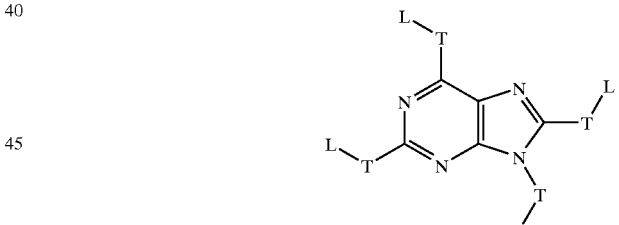

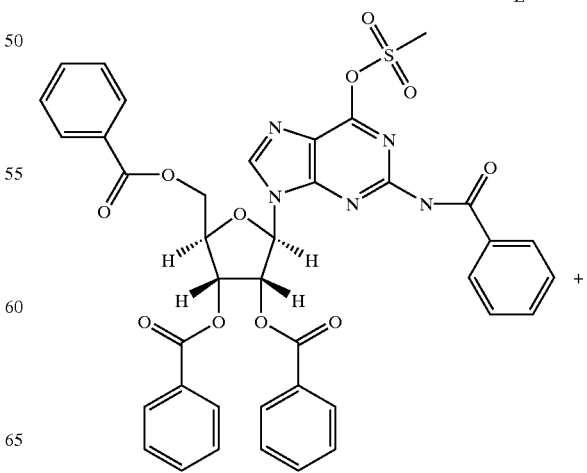

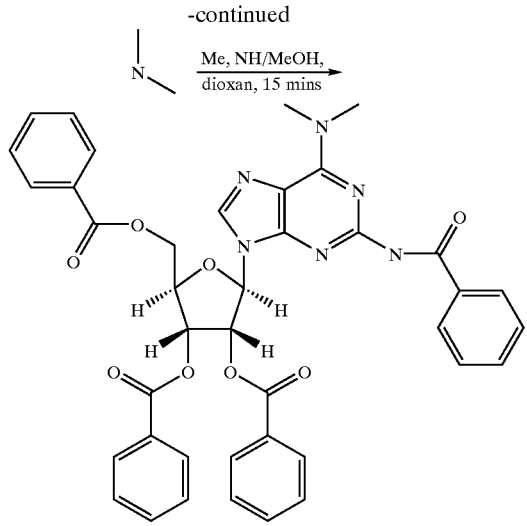
Bridson, P. K., Markiewicz, W., Reese, C. B., *J. Chem. Soc, Chem. Commun.*, 1977, 444.
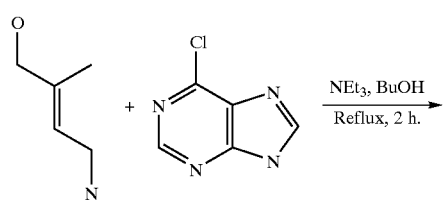
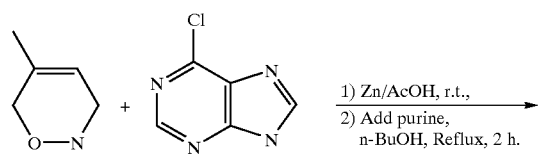
Corse, J., Kuhnle, J., *Synthesis*, 1972, 618.
Leonard, N. J., Plattis, A. J., Skoog, F., Schmitz, R. Y., *J. Am. Chem. Soc.*, 1971, 93, 3056-.
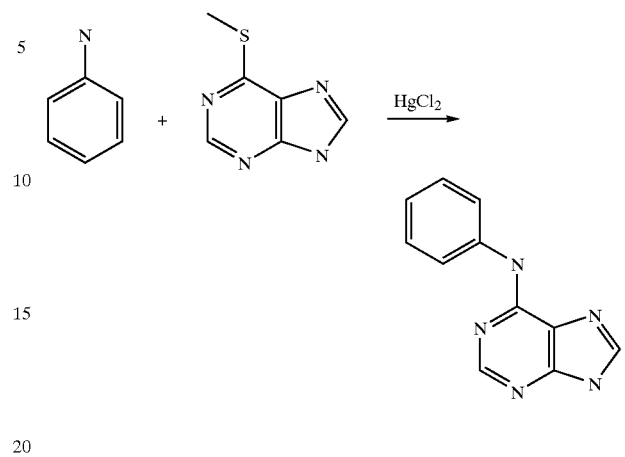
Gracheva, E. P., et al., *Izv Akad Nauk SSSR, Ser Khim*, 1970, 420.
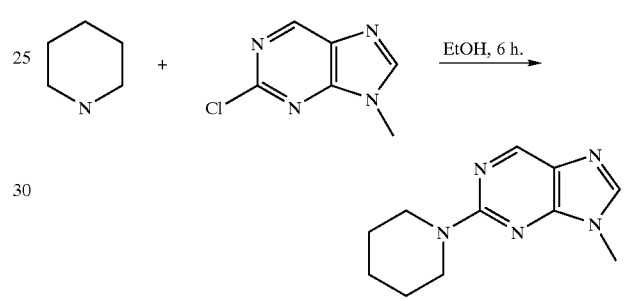
Barlin, G. B., *J. Chem. Soc. B.*, 1967, 954.
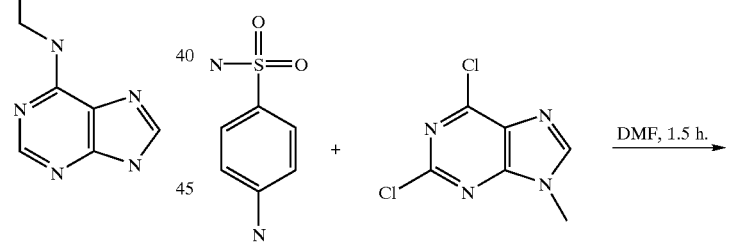
Beaman, A. G., et al., *J. Med Chem.*, 1966, 9, 373.
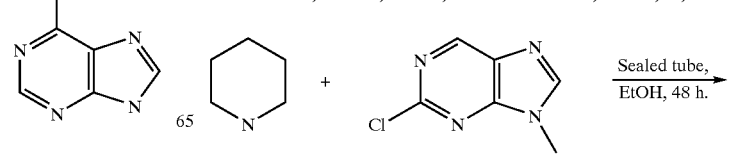

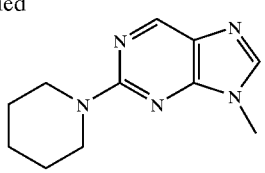

Barlin, G. B., Chapman, N. B., *J. Chem. Soc.*, 1965, 3017.

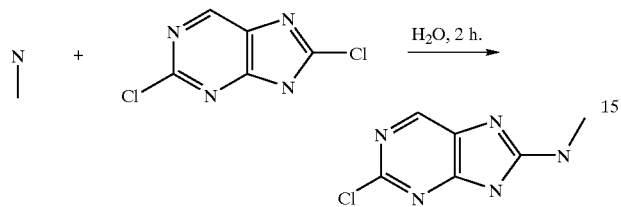

Lewis, A. F., Robins, R. K., *Can. J. Chem.*, 1963, 41, 1807.

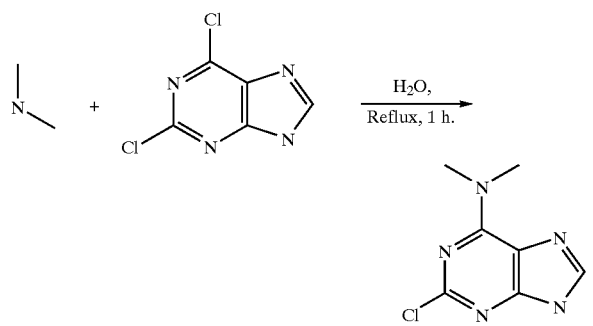

Montgomery, J. A., Holum, L. B., *J. Am. Chem. Soc.*, 1959, 80, 404.

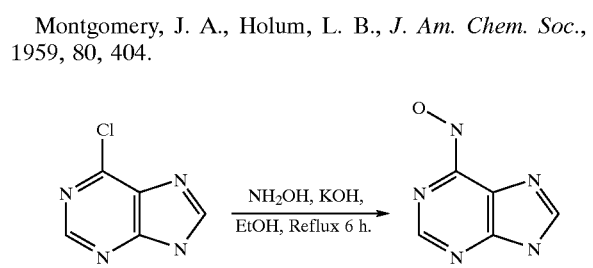

Giner-Sorolla, A., Bendich, A., *J. Am. Chem. Soc.*, 1959, 80, 3932.

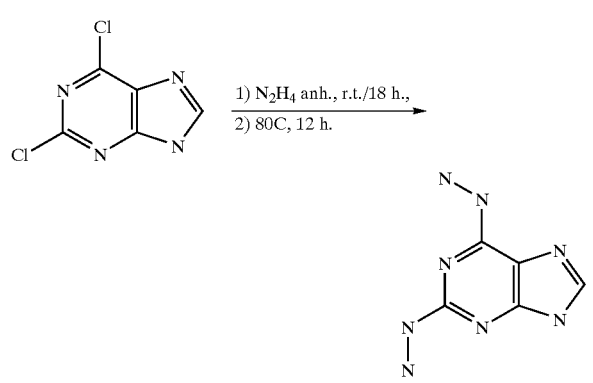

Montgomery, J. A., Holum, L. B., *J. Am. Chem. Soc.*, 1957, 79, 2185.

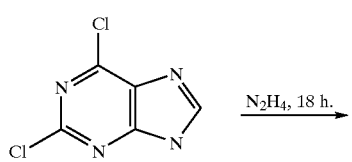

Montgomery, J. A., Holum, L. B., *J. Am. Chem. Soc.*, 1957, 79, 2185.

Albert, A., Brown, D., *J. Chem. Soc.*, 1954, 2060.

In a further aspect of the present invention, purines having halogen substituents are treated with reagents under conditions effective to displace the halogens with a letter that is covalently bound via a thio tether. The general reaction scheme followed by representative reactions is shown below:

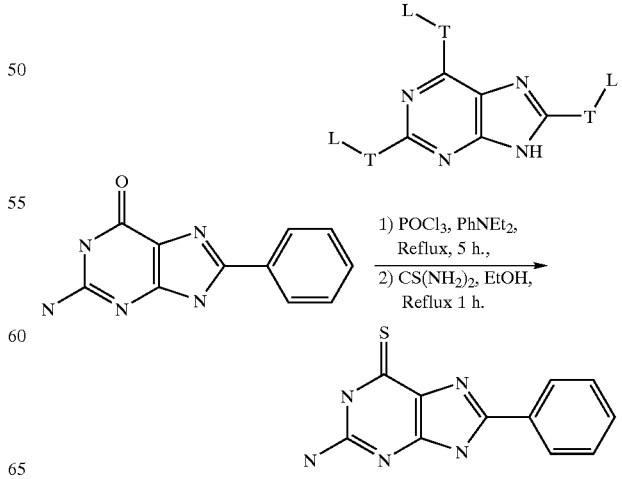

Fu, S. C. J., et al., *J. Med. Chem.*, 1967, 10, 109.

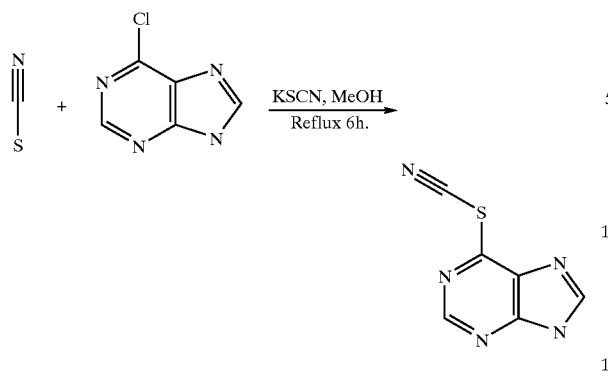
Elion, G. B., et al., *J. Am. Chem. Soc.*, 1959, 81, 1898.
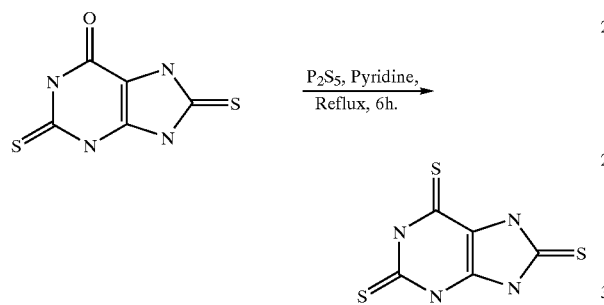
Noell, C. W., Robins, R. K., *J. Am. Chem. Soc.*, 1959, 81, 5997.
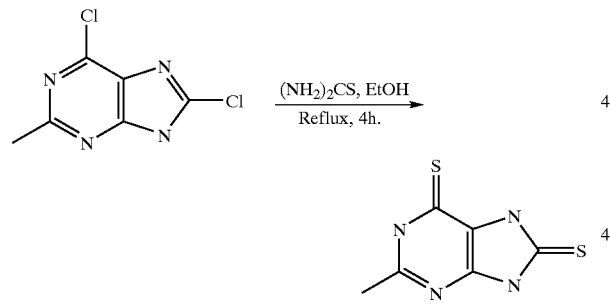
Noell, C. W., Robins, R. K., *J. Org. Chem.*, 1959, 24, 320.
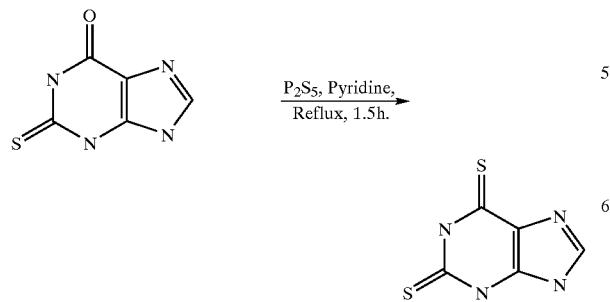
Beaman, A. G., *J. Am. Chem. Soc.*, 1954, 76, 5623.
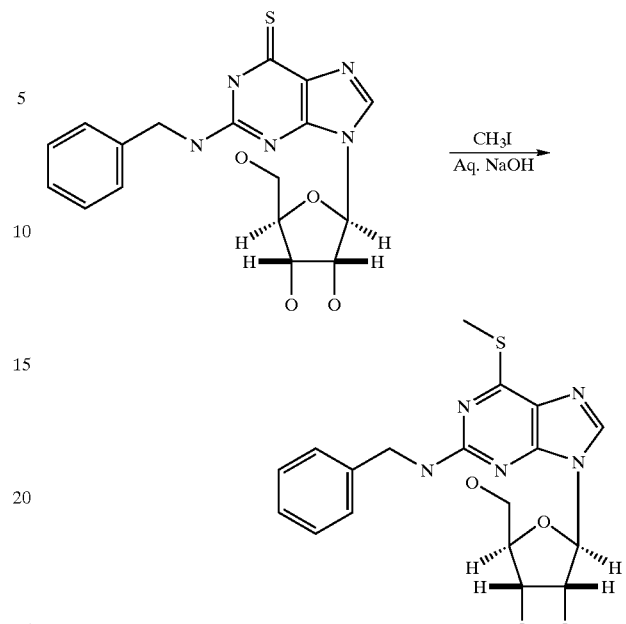
Omura, K., et al., *Chem. Pharm. Bull.*, 1981, 29, 1870.
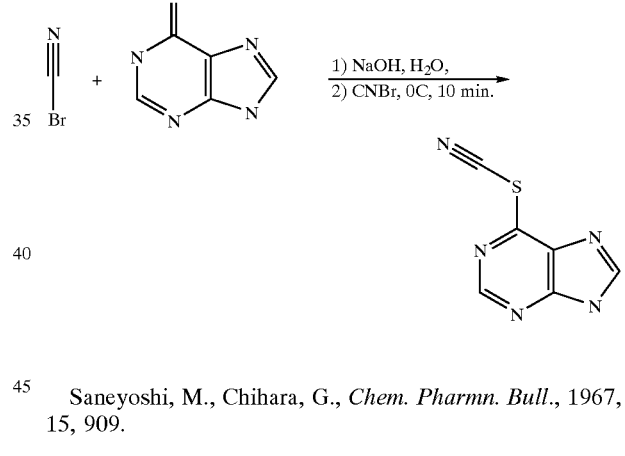
Saneyoshi, M., Chihara, G., *Chem. Pharmn. Bull.*, 1967, 15, 909.
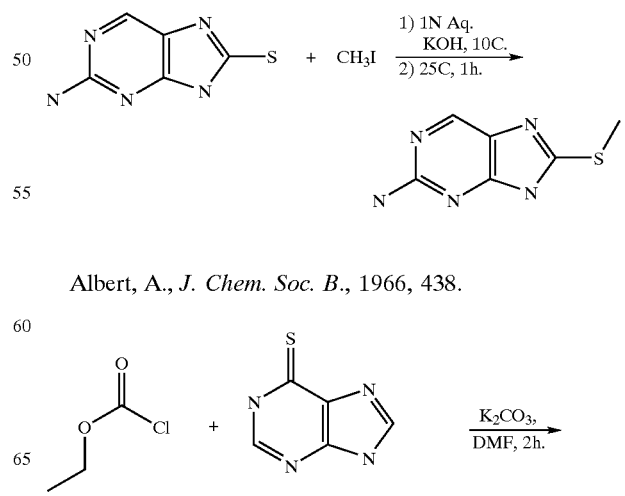
Albert, A., *J. Chem. Soc. B.*, 1966, 438.

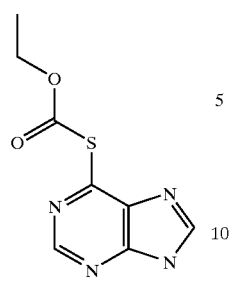

Dyer E., Bender, H. S., *J. Med. Chem.*, 1964, 7, 10.

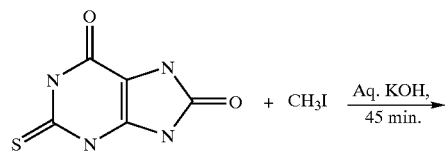

Noell, C. W., Robins, R. K., *J. Org. Chem.*, 1959, 24, 320.

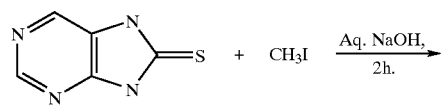

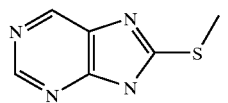

Albert, A., Brown, D. J., *J. Chem. Soc.*, 1954, 2060.

In another aspect of the present invention halogen or thio substituents on purines are displaced giving alkoxy or aryloxy substituents. The alkoxy group functions as a tether to attach letters to the purines. The general reaction scheme followed by representative reactions is shown below:

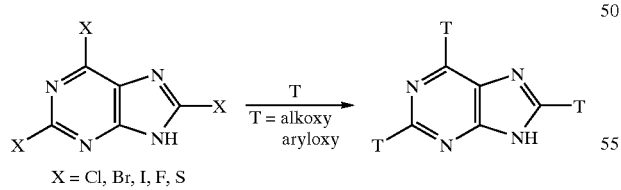

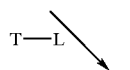

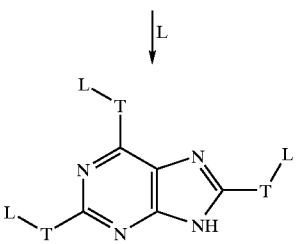

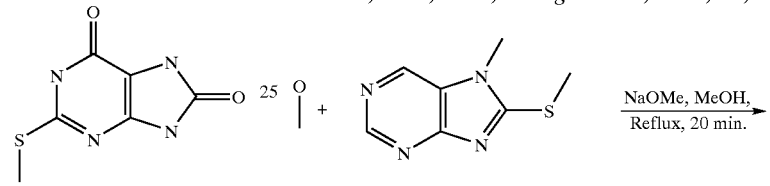

Keck, J. H., et al., *J. Org. Chem.*, 1978, 43, 2587.

Badger, R. J., Barlin, G. B., *J. Chem. Soc., Perkin Trans 2*, 1976, 1176.

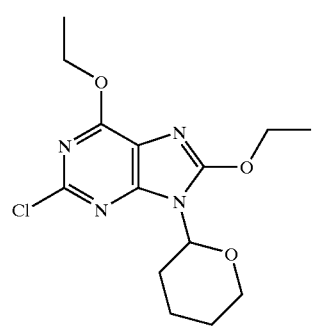

Sutcliffe, E. Y., Robins, R. K., *J. Org. Chem.*, 1963, 28, 1662.

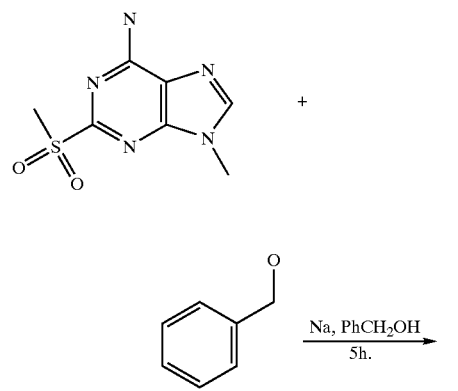

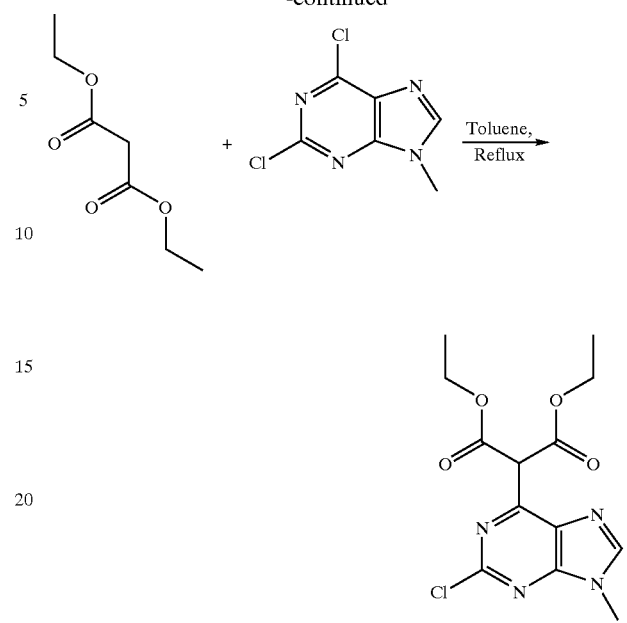

Chaman, E. S., et al., *Zh. Obshch. Khim.*, 1963, 33, 3342.

Andrews, K. J. M., et al., *J. Chem. Soc.*, 1949, 2490.

In another aspect of the present invention halogen substituents on purines are displaced in a one or two step process to give malonate substituted purines. The malonate group functions as a tether to attach letters to the purines. The general reaction scheme followed by specific reactions is shown below:

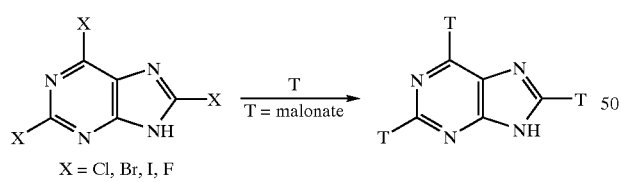

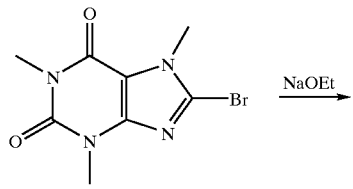

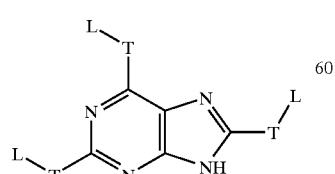

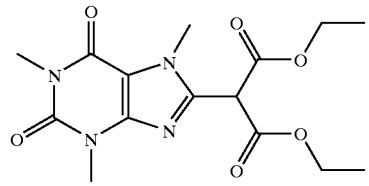

Bargioni, G., *Boll. Chin. Farm.*, 1935, 64, 869.

In a further aspect of the present invention purines are hydrogenated in the presence of selected compounds to give substituted purines. The general reaction scheme followed by specific reactions is shown below:

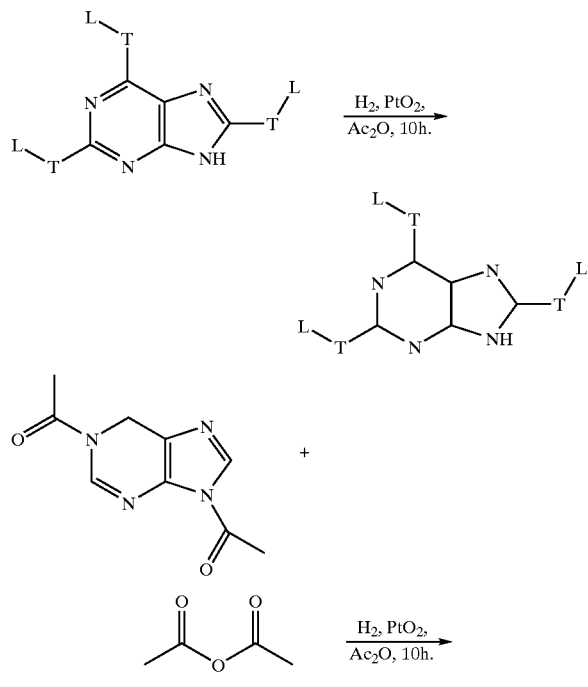

Butula, I., *Justus Liebigs Ann. Chem.*, 1969, 73, 1969.

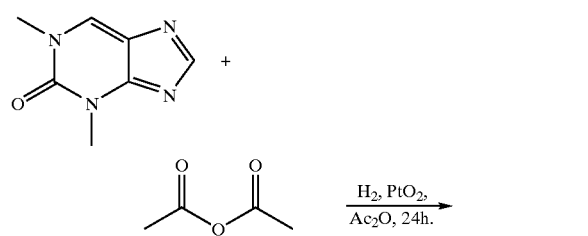

Butula, I., *Justus Liebigs Ann. Chem.*, 1969, 73, 1969.

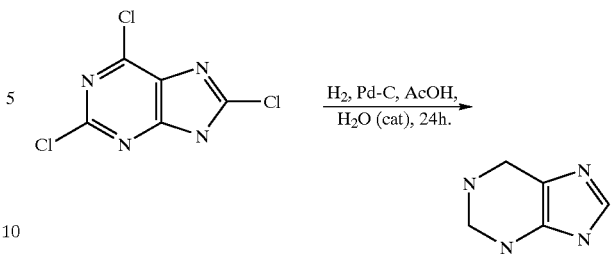

Breshears, S. R., et al., *J. Am. Chem.*, 1959, 81, 3789.

In yet another aspect of the present invention halogen or thio atoms on pyrimidines are displaced in a one or two step process to give tethered or untethered letters (chemical substituents) attached to the ring. The general reaction scheme followed by representative reactions is shown below:

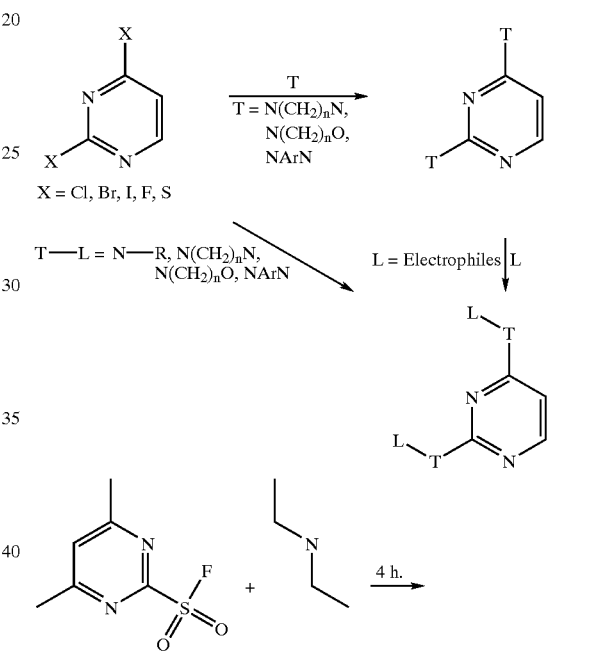

Brown, K. J., Hoskins, J. A., *J. Chem. Soc.*, 1972, 522.

Arantz, B. W., Brown, D. J., *J. Chem. Soc.*, 1971, 1889.

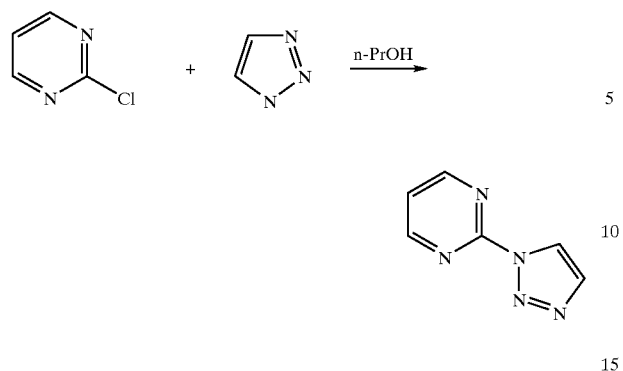
Huber, A. J., Reimlinger, H., *Chem. Ber.*, 1970, 103, 3811.
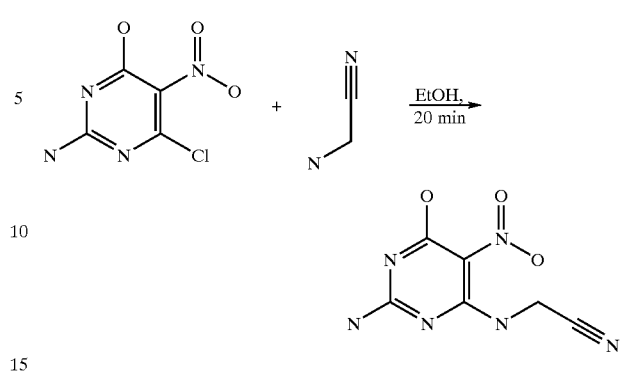
Stuart, A., et al., *J. Chem. Soc.*, 1964, 4769.
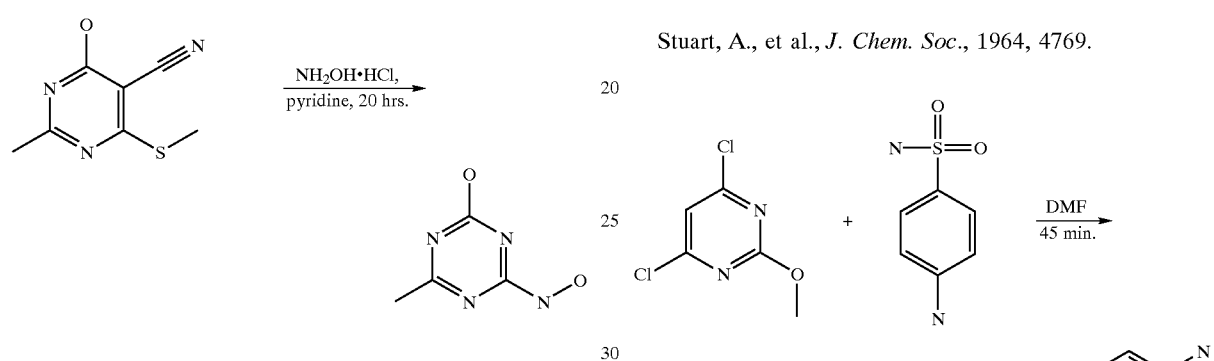
Dornow, A., Dehmer, K., *Chem. Ber.*, 1967, 100, 2577.
Brown, D. J., Ford, P. W., *J. Chem. Soc. C.*, 1967, 568.
Bretschneider, H., et al., *Monatsh. Chem.*, 1964, 95, 207.
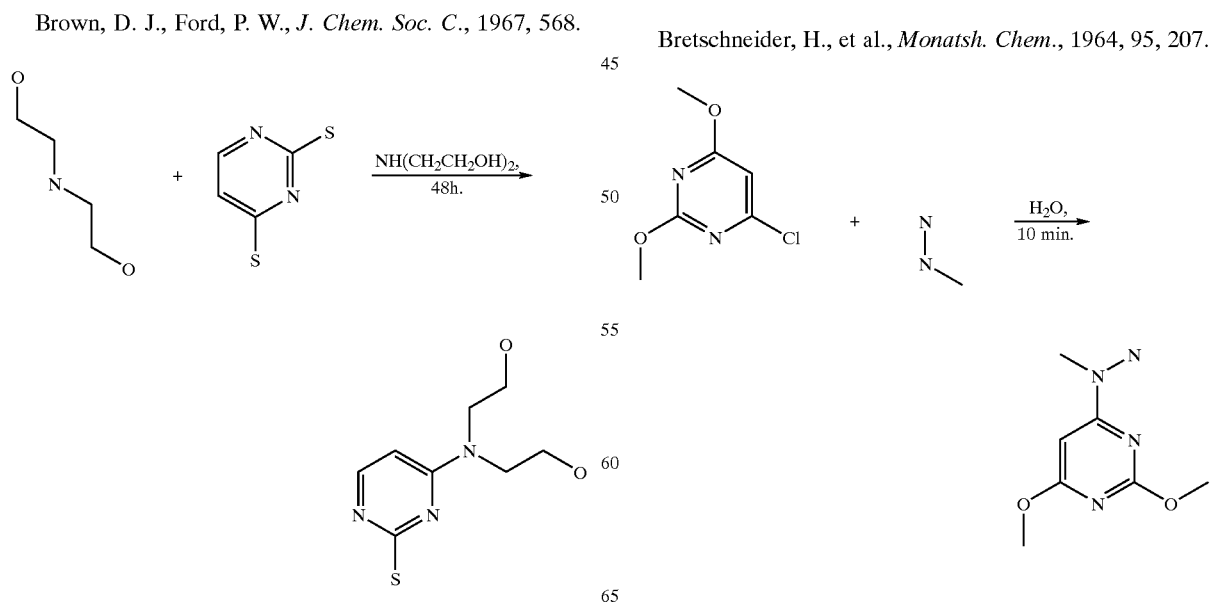
Nagpal, K. L., Dhar, M. M., *Tetrahedron*, 1967, 23, 1297.
Nagase, O., et al., *Yakugaku Zasshi*, 1962, 82, 528.

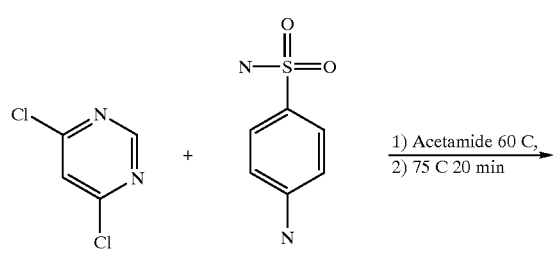

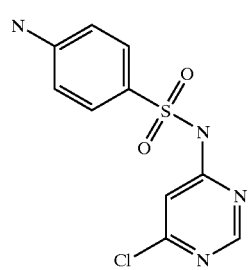

Shepherd, R. G., et al., *J. Org. Chem.*, 1961, 26, 2764.

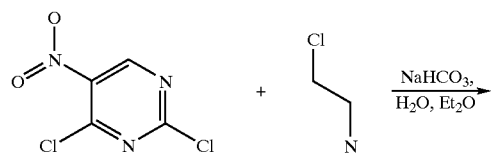

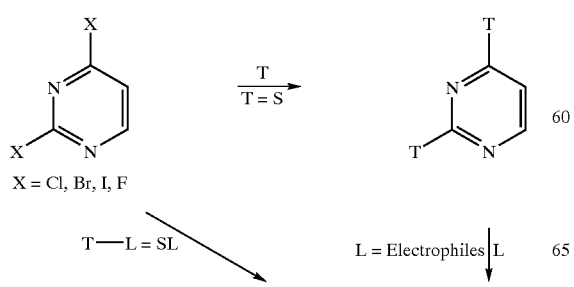

Martin, R. J., Mathieu, J., *Tetrahedron*, 1957, 1, 75.

In another aspect of the present invention halogen substituents on pyrimidines are displaced in a one or two step process to give tethered or untethered letters attached to the ring through a sulfur atom. The general reaction scheme followed by representative reactions is shown below:

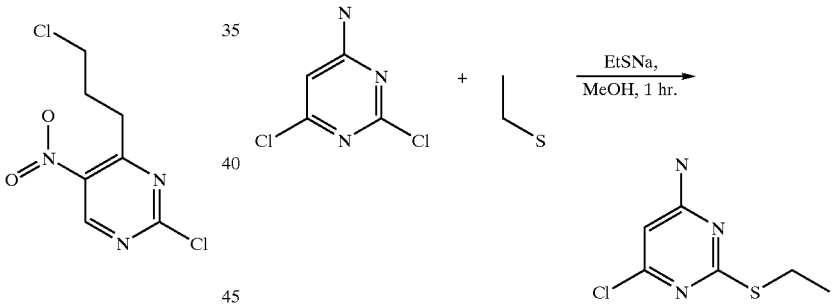

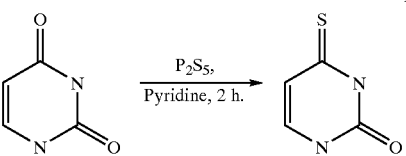

Brown, D. J., Shinozuka, K., *Aust. J. Chem.*, 1980, 33, 1147.

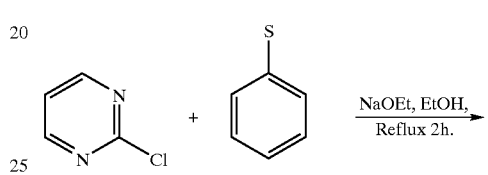

Brown, D. J., Ford, P. W., *J. Chem. Soc.*, 1967, 568.

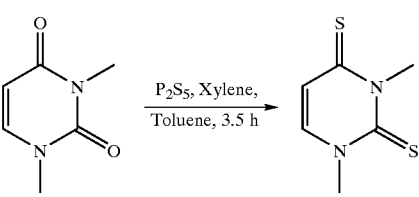

Spiteller, G., Bretschneider, H., *Montash. Chem.*, 1961, 92, 103.

Elion, G. B., Hitchings, G. H., *J. Am. Chem. Soc.*, 1947, 69, 2138.

In still further aspect of the present invention halogen substituents on pyrimidines are displaced in a one or two step process to give tethered or untethered letters attached to the ring through an oxygen atom. The general reaction scheme followed by representative reactions is shown below:

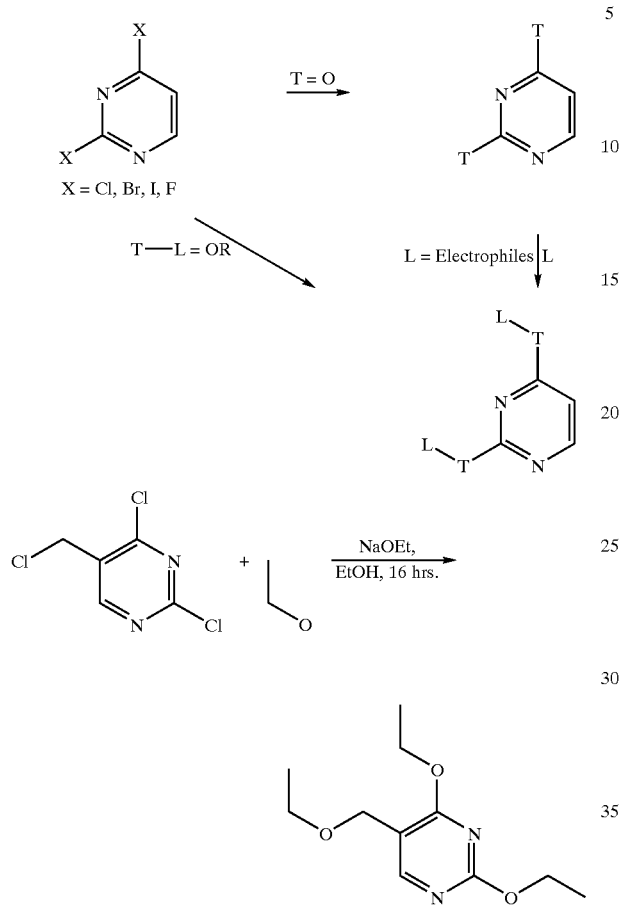

Brossmer, R., Rohm, E., *Justus Liebigs Ann. Chem.*, 1966, 692, 119.

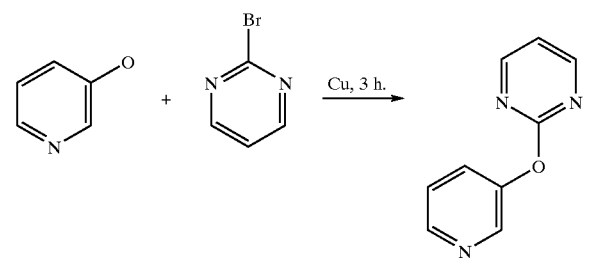

Kajihara, S., et al., *Nippon Kagaku Zasshi*, 1966, 87, 884.

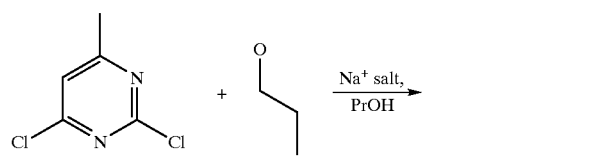

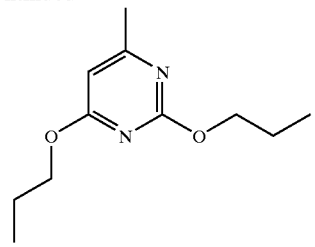

Profft, E., Raddatz, H., *Arch. Pharm. Ber. Dtsch. Pharm.*, 1962, 295, 649.

In another aspect of the present invention halogen substituents on pyrimidines are displaced in a one or two step process to give Se tethered letters attached to the ring. The general reaction scheme followed by representative reactions is shown below:

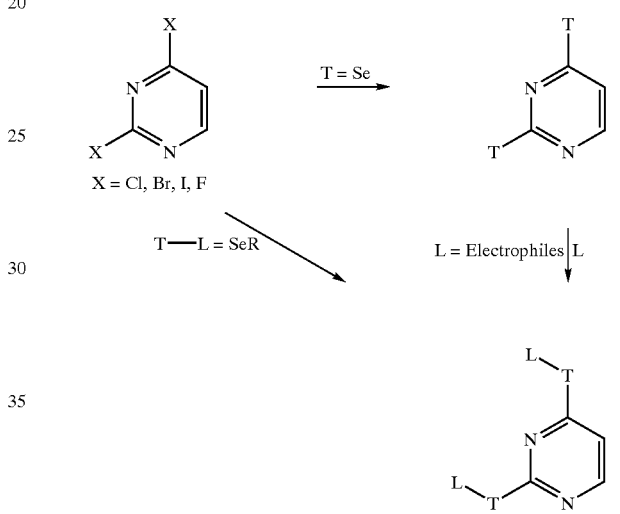

Mautner, H. G., et al., *J. Med. Chem.*, 1963, 6, 36.

In another aspect of the present invention halogen substituents on pyrimidines are displaced in a one or two step process to give phosphorus tethered letters attached to the pyrimidine ring. The general reaction scheme followed by specific reactions is shown below:

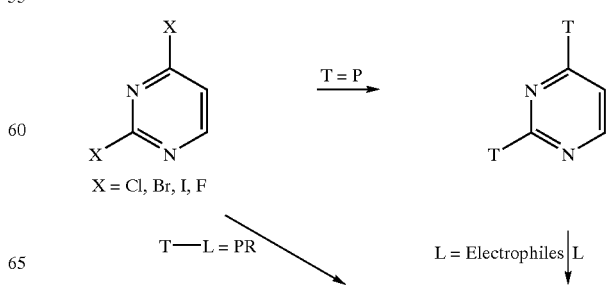

33
-continued
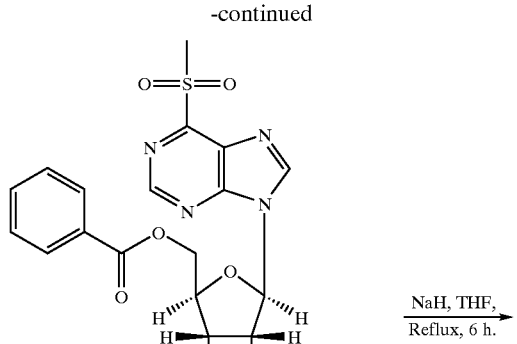
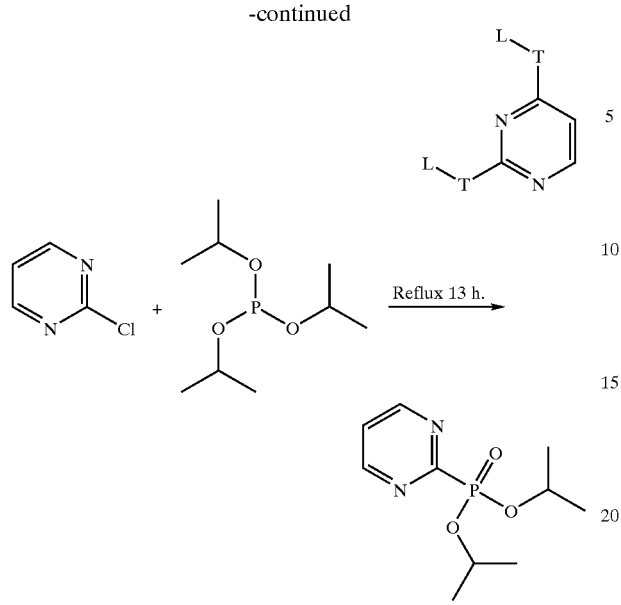
Kosolapoff, G. M., Roy, C. H., *J. Org. Chem.*, 1961, 26, 1895.
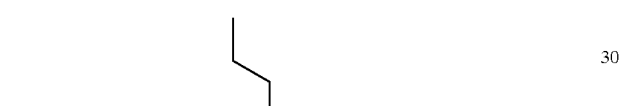
Kosolapoff, G. M., Roy, C. H., *J. Org. Chem.*, 1961, 26, 1895.
Yamane, A., et al., *Chem. Pharm. Bull.*, 1980, 28, 150.
34
-continued
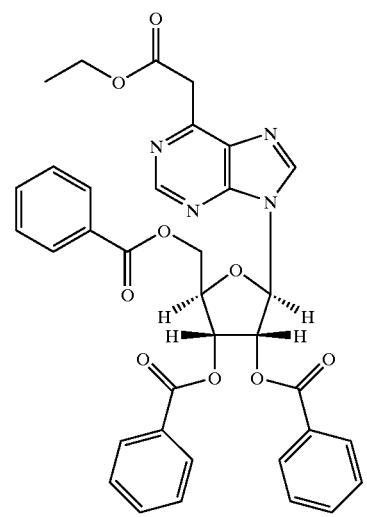
Yamane, A., et al., *Chem. Pharm. Bull.*, 1980, 28, 150.
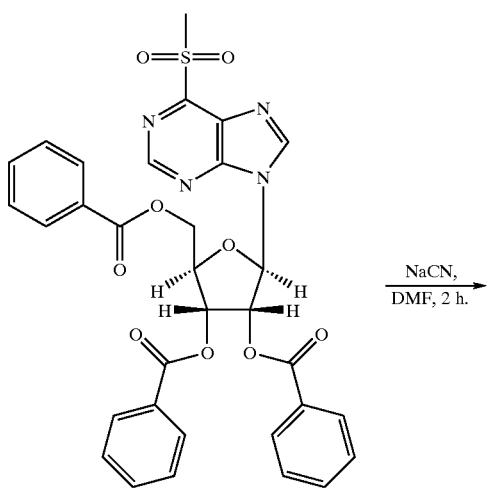
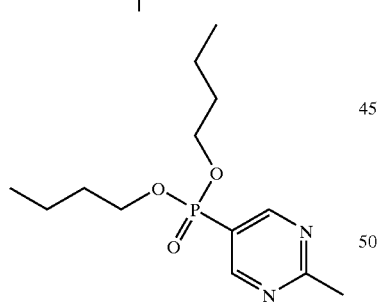

-continued
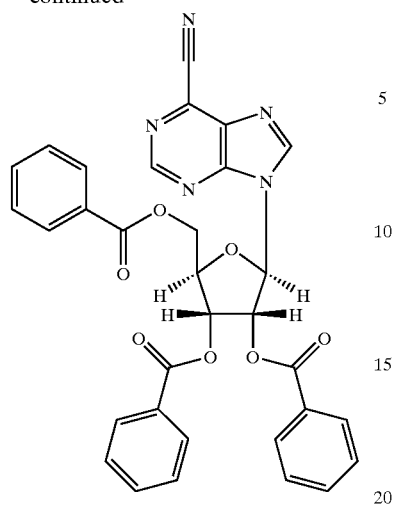
Yamane, A., et al., *Chem. Pharm. Bull.*, 1980, 28, 150.
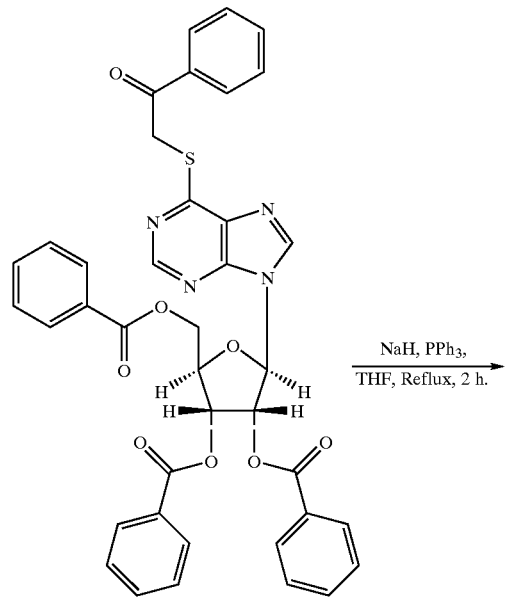
Yamane, A., et al., *Chem. Pharm. Bull.*, 1980, 28, 157.
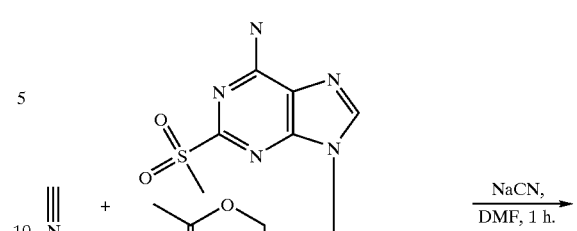
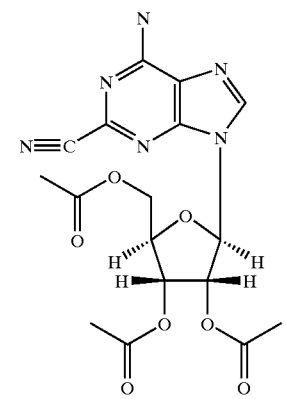
Matsuda, A., et al., *Chem. Pharm. Bull.*, 1979, 27, 183.
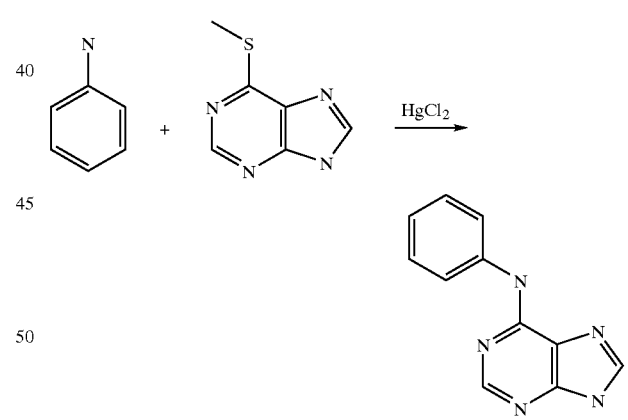
Gracheva, E. P., et al., *Izv. Akad. Nauk. SSSR, Ser. Khim.*, 1970, 420.
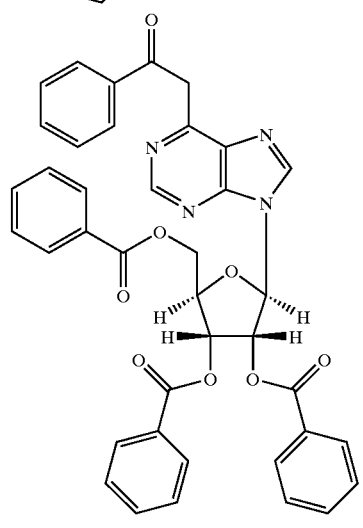

-continued

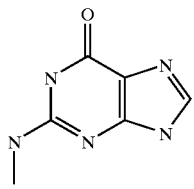

Elion, G. B., et al., *J. Am. Chem. Soc.*, 1956, 78, 217.

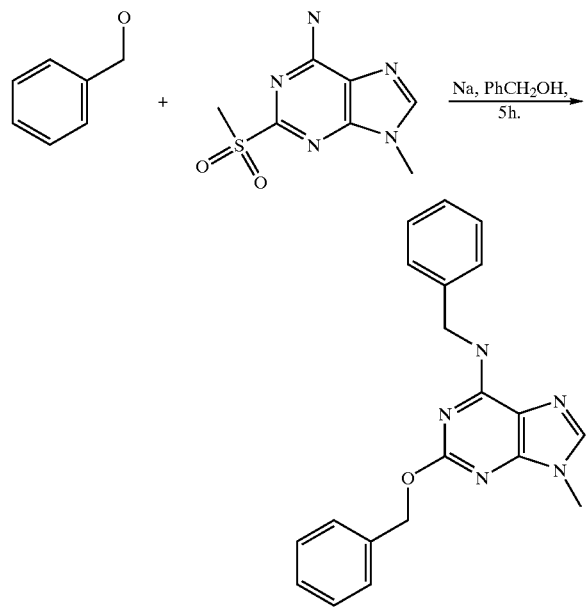

Andrews, K. J. M., et al., *J. Chem. Soc.*, 1949, 2490.

EXAMPLES

"Letters" as used in these examples are chemical substituents for attachment to scaffolds or tethers. They are exemplary only and are listed here for reference: N-(α-bromoacetyl)-1-aminocycloheptane(Br-$L_1$); N-(α-bromoacetyl)-m-nitroaniline(Br-$L_2$); N-(α-bromoacetyl)-p-methoxyaniline(Br-$L_3$); N-(α-Bromoacetyl)-2-aminobenzothiazole(Br-$L_4$); N-(α-Bromoacetyl)-2-aminomethylfuran(Br-$L_5$); m-chloro-benzylbromide(Br-$L_6$); m-cyanlobenzylbromide(Br-$L_7$); m-nitrobenzylbromide(Br-$L_8$); m-methylesterbenzylbromide(Br-$L_9$); m-triflouromethylbenzylbromide(Br-$L_{10}$); N-(α-bromoacetyl)-3-amino-5-methylisoxazole(Br-$L_{11}$); N-(α-bromoacetyl)tetrahydro-isoquinoline(Br-$L_{12}$); adamantane-1-carborbonylchloride(Br-$L_{13}$); bromoacetonitrile(Br-$L_{14}$); propargyl bromide(Br-$L_{15}$); 2-bromoacetamide(Br-$L_{17}$); 1-bromo-2-butanone(Br-$L_{18}$); 6-(bromoacetyl)-1,2,3,4-tetrahydro-1,1,4,4-tetramethyl-naphthalene(Br-$L_{19}$); 6-(Bromoacetyl)-2-oxo-1,2,3,4-tetrahydroquinoline(Br-$L_{20}$); 2-(bromoacetyl)-5-chloro-3-methylbenzo[b]thiophene (Br-$L_{21}$); 5-(bromomethyl)benzo-furazan(Br-$L_{22}$); 3-(bromomethyl)-5-chlorobenzo[b]thiophene(Br-$L_{23}$); 6-(bromomethyl)-4-chloro-2-trifluoromethyl)quinoline(Br-$L_{24}$); 4-(4-bromomethylphenyl)-1,2,3-thiadiazole(Br-$L_{25}$); N-(α-bromoacetyl)-4-methyl-2-amino-thiazole(Br-$L_{26}$); α-Bromo-m-xylene(Br-$L_{27}$); m-Fluoro-benzylbromide(Br-$L_{28}$); 3-(bromomethyl)-benzonitrile(Br-$L_{29}$); m-bromobenzyl bromide(Br-$L_{30}$); 2-bromo-N'-(2'-ethyl-bis-N-tert-butoxycarbonyl-guanidino)-acetamide(Br-$L_{31}$); N'-4'-(bromoacetyl)-piperazino-N'-1'-(bis-N-tert-butoxycarbonyl-1-carboxamidine(Br-$L_{32}$); 2-bromo-N-(2'-ethyl-N'-tert-butoxycarbonylamino)-acetamide(Br-$L_{33}$); N-4-(bromoacetyl)-N-1-(tert-butoxycarbonyl)-piperazine (Br-$L_{34}$); benzyl bromide(Br-$L_{35}$); and cinnamyl bromide (Br-$L_{36}$)

Example 1 tert-Butyl-1-piperazinecarbozylate

Piperazine (236 g, 2.75 mmol, 6 eq.) was suspended in acetonitrile (1.8 L) in a three neck round bottom flask fitted with a mechanical stirrer and diisopropylethylamine (87.96 mL, 504 mmol) was added. Di-tert-butyldicarbonate was dissolved in acetonitrile (200 mL) and added to the reaction mixture via dropping funnel. A white precipitate formed overnight which was filtered, washed twice with acetonitrile (50 mL) and dried in vacuo. The filtrate was concentrated in vacuo and additional white precipitate (piperazine) was filtered from the reaction mixture. The filtrate was reduced in volume in vacuo and partitioned between water and hexane (100 mL/100 mL). The water was extracted twice with hexane (100 mL). The hexane layers were pooled, washed with brine (100 mL), dried ($MgSO_4$) and concentrated in vacuo to give 66.32 g (79%) of the title compound. $^1$H NMR ($CDCl_3$): δ 1.45 (s, 9H), 2.79 (t, 4H), 3.38 (t, 4H).

Example 2

N1-t-Boc-N2-α-bromoacetylpiperazine tert-Butyl-1-piperazinecarboxylate (10 g, 53.69 mmol) was dissolved in tetrahydrofuran (250 mL) and diisopropylethylamine (10.29 mL, 59.06 mmol) was added. The reaction mixture was cooled in an ice bath for 20 minutes and bromoacetyl bromide (5.13 mL, 59.06 mmol) was added. The reaction progress was monitored by thin layer chromatography using MeOH:$CH_2Cl_2$ (5/95, v/v) which showed disappearance of starting material and formation of a new UV active product spot after 20 hours. The reaction was partitioned between water and $CH_2Cl_2$ (100 mL/100 mL), separated, and the aqueous layer was extracted twice with $CH_2Cl_2$ (100 mL). The organic layers were pooled and washed with brine (100 mL), dried ($MgSO_4$), filtered and concentrated. The resulting residue was purified by silica gel flash column chromatography using MeOH:$CH_2Cl_2$ (5/95, v/v) as the eluent. The appropriate fractions were pooled and concentrated to give 10.63 g (66%) of the title compound. $^1$H NMR ($CDCl_3$): δ 1.48 (s, 9H), 3.39–3.63 (m, 8H), 3.97 (s, 2H).

Example 3

N1-(Trimethylsilylethozycarbonyl)piperazine

Piperazine (36.48 g, 423 mmol) was dissolved in acetonitrile (1 L) and 2-(trimethylsilyl)ethyl-p-nitrophenylcarbonate in acetonitrile (500 mL) was added via a dropping funnel. The reaction progress was monitored by thin layer chromatography using MeOH:$CH_2Cl_2$ (10/90, v/v) which showed disappearance of starting material and formation of a new product spot after 20 hours. The acetonitrile was evaporated to a yellowish residue. The residue was partitioned between water (600 mL) and hexane (100 mL). After separation the water layer was extracted twice with hexane (100 mL). The hexane layers were pooled, dried ($MgSO_4$), filtered, and evaporated to give 15.24 g (94%) of the title compound. $^1$H NMR (CDCl$_3$): δ 0.02 (s, 9H), 0.99 (t, 2H), 1.79 (bs, NH), 2.80 (t, 4H), 3.41 (t, 4H), 4.26 (t, 2H).

Example 4

2–Chloro-6-[N-(trimethylsilylethoxycarbonyl) piperazinyl]purine

To 2,6-dichloropurine (8.86 g, 57.73 mmol) dissolved in a mixture of CH$_2$Cl$_2$ (200 mL), MeOH (50 mL) and DPEA (7.71 mL, 63.50 mmol) was added N1-(trimethylsilylethoxycarbonyl) piperazine (13.30 g, 57.73 mmol) as a solid. The reaction progress was monitored by thin layer chromatography MeOH:EtOAc:hexane (1/49/50, v/v/v) which showed disappearance of starting material and formation of a new product spot after 15 hours. The solvent was removed in vacuo and the residue left behind was partitioned between water (100 mL) and CH$_2$Cl$_2$ (100 mL). The water layer was separated and extracted twice with CH$_2$Cl$_2$ (50 mL). The CH$_2$Cl$_2$ fractions were combined and washed with brine (100 mL), dried (MgSO$_4$), filtered and evaporated. The residue was purified by silica gel flash column chromatography using MeOH:EtOAc:CH$_2$Cl$_2$ (1/49/50, v/v/v) as the eluent. The appropriate fractions were pooled and evaporated to give 15.70 g (71%) of the title compound. $^1$H NMR (CDCl$_3$): δ 0.02 (s, 9H), 1.04 (t, 2H), 3.69 (t, 4H), 4.25 (t, 2H), 4.40 (bs, 4$_A$H), 7.99 (s, 1H), 13.5 (bs, NH).

Example 5

2-Piperazinyl-6-[N-(trimethylsilylethoxycarbonyl)-piperazinyl]purine

2–Chloro-6-[N-(trimethylsilylethoxycarbonyl)-piperazinyl]purine (17.10 g, 44.66 mmol) and piperazine (23.08 g, 268 mmol) were suspended in EtOH (200 mL) in a bomb reactor. The bomb reactor was heated to 145° C. for 24 hours. The reaction progress was monitored by thin layer chromatography NH$_4$OH:MeOH:EtOAc (5/5/90, v/v/v) which showed disappearance of starting material and formation of a new product spot after 24 hours. The EtOH was evaporated and water (700 mL) was added to the residue. The resulting precipitate was filtered and dried in a vacuum oven at 110° C. for 24 hours to give 18.5 g (96%) of the title compound. $^1$H NMR (CDCl$_3$): δ 0.02 (s, 9H), 1.01 (t, 2H), 2.99 (bs, 4H), 3.61 (bs, 4H), 3.74 (bs, 6H), 4.23 (bm, 6H), 7.59 (s, 1H).

Example 6

2-Piperazinyl-6-[N-(trimethylsilylethoxycarbonyl)-piperazinyl]-N9-[(N'-t-Boc-N"-acetyl)piperazinyl] purine 2-Piperazinyl-6-[N-(trimethylsilylethoxycarbonyl) pipera-zinyl]purine (8 g, 18.49 mmol) was dissolved in DMF (250 mL) and 1N NaOH (18.49 mL) was added. The reaction mixture was cooled in an ice bath for 20 minutes. With the reaction mixture at 0° C. N1-t-Boc-N2-α-bromoacetylpiperazine dissolved in DMF (250 mL) was added slowly via a dropping funnel. The reaction progress was monitored by thin layer chromatography using MeOH:EtOAc:CH$_2$Cl$_2$ (10/30/60, v/v/v) which showed completion of the reaction after 20 hours. The reaction mixture was partitioned between water (300 mL) and CH$_2$Cl$_2$ (200 mL) to give an emulsion. Brine (100 mL) was added to break up the emulsion. The aqueous phase was separated and extracted with CH$_2$Cl$_2$ (100 mL). The organic phases were combined, dried (MgSO$_4$), filtered and concentrated. The residue was purified by silica gel flash column chromatography using MeOH:EtOAc:CH$_2$Cl$_2$ (10/30/60, v/v/v) as the eluent. The appropriate fractions were pooled and evaporated to give 7.31 g (60%) of the title compound. $^1$H NMR (CDCl$_3$): δ 0.08 (s, 9H), 1.02 (t, 2H), 1.48 (s, 9H), 2.57 (bs, 4H), 2.98 (bs, 4H), 3.41 (bs, 4H), 3.58 (bs, 8H), 3.77 (bs, 4H), 4.20 (bm, 6H), 4.87 (bs, 2H), 7.60 (s, 1H).

Example 7

2,6-Dipiperazinylpurine 2,6-Dichloropurine (100 g, 529 mmol) and piperazine (228 g, 2.65 moles) was placed in a large stainless steel bomb. Ethyl alcohol (500 mL) was added and the bomb was sealed and heated in an oil bath to an external temperature of 140° C. The reaction was complete after 24 hours as indicated by TLC using NH$_4$OH:MeOH:THF (10/10/80, v/v/v). The reaction was concentrated in vacuo to a yellow powder. The powder was extracted with hexane via a soxhlet extractor for 10 hours to remove piperazine. The remaining solid was dissolved in MeOH (500 mL) and silica gel (100 g) was added. The MeOH was evaporated to afford the material loaded on the silica as a free moving silica solid. This material was purified by silica gel flash column chromatography using NH$_4$OH:MeOH:THF (10/10/80, v/v/v) as the eluent. The appropriate fractions were collected and concentrated to afford 67 g (94%) of the title compound. $^1$H NMR (DMSO): δ 2.63–2.81 (bm, 8H), 3.49–3.59 (bt, 4H), 3.99–4.23 (bs, 4H), 7.70 (s, 1H).

Example 8

2,6-Dipiperazinyl-N9-[(N'-t-Boc-N"-acetyl) piperazinyl]purine

Method A 2,6-Dipiperazinylpurine (5 g, 17.34 mmol) was dissolved in 100 mL DMF with heat. The solution was cooled to 0° C. and sodium hydride (832 mg, 20.81 mmol) was added. The reaction mixture was stirred until bubbling ceased, about 1 hour. N1-t-Boc-N4-α-bromoacetylpiperazine was dissolved in DMF (20 mL) and added to the reaction mixture dropwise with the temperature of the reaction mixture maintained at 0° C. The reaction was complete after 4 hours as indicated by TLC using NH$_4$OH:MeOH:EtOAc (5/5/90, v/v/v). The solvent was evaporated leaving a yellow residue. The residue was purified by silica gel flash column chromatography using MeOH:NH$_4$OH:THF (3/3/94–5/5/90, v/v/v) as the eluent. The appropriate fractions were pooled and evaporated to give 4.85 g (54%) of the title compound. $^1$H NMR (DMSO): δ 1.42 (s, 9H), 2.65–2.92 (bm, 8H), 3.32 (bs, 2H), 3.42 (bs, 4H), 3.57 (bs, 6H), 4.05 (bs, 4H), 4.99 (bs, 2H), 7.67 (s, 1H). Mass Spectrum (ES+) m/z 515 [M+H]$^+$.

Method B

2-Piperazinyl-6-[N-(trimethylsilylethoxycarbonyl)-piperazinyl]-N9-[(N'-t-Boc-N"-acetyl)piperazinyl]purine (10 mg, 15 mmol) was dissolved in THF (1 mL) and the resulting solution was treated with tetrabutylammonium fluoride (1M) in THF (50 mL). The progress of the reaction was monitored by TLC using NH$_4$OH:MeOH:THF (5/5/90, v/v/v). TLC after 45 minutes showed complete deprotection to the title compound.

Example 9

[2,6-Dipiperazinyl-N,N-bis-benzylcarbamate)]purine 2,6-Dipiperazinylpurine (1.0 g, 3.47 mmol) was dissolved in DMF (100 mL), MeOH (25 mL) and diisopropylethyl amine (1.33 mL, 7.63 mmol, 2 eq.). To this stirred solution was added a second solution of N-(benzyloxycarbonyl-oxy)succinimide (1.73 g, 6.49 mmol, 2 eq.) in DMF (20 mL) dropwise via addition funnel. The reaction was complete after 16 hours at ambient temperature as indicated by TLC. The reaction mixture was concentrated to a residue that was partitioned between ethyl acetate and water. The aqueous layer was separated and extracted twice with ethyl acetate. The combined ethyl acetate layers were washed with brine, dried ($MgSO_4$), filtered and concentrated to give a yellow oil. The oil was purified by silica gel flash column chromatography using $MeOH:EtOAc:CH_2Cl_2$ (2/48/50, v/v/v) as the eluent. Pooling, concentrating and drying of the appropriate fractions gave 1.19 g (62%) of the title compound. $^1H$ NMR ($CDCl_3$): δ 3.36 (bs, 4H, 2×$CH_2$), 3.51 (bs, 4H, 2×$CH_2$), 3.64 (bs, 4H, 2×$CH_2$), 4.19 (bs, 4H, 2×$CH_2$), 5.13 (d, 4H, 2×benzyl $CH_2$), 7.38 (m, 10H, 2×aryl H's), 7.80 (s, 1H, C8 H), 12.22 (bs, 1H, NH).

Example 10

[2,6-Dipiperazinyl-(N,N-bis-benzylcarbamate)]-N9-[(N'-t-Boc-N"-acetyl)piperazinyl]purine Dissolve [2,6-dipiperazinyl-N,N-bis-benzylcarbamate)] purine (260 g, 467 mmol) in DMF (4 L) and cool in an ice bath to 0° C. NaOH (607.34 mL, 1N, 1.3 eq.) was added dropwise over 20 minutes. To this mixture was added a solution of N1-t-Boc-N2-α-bromoacetylpiperazine (186.54 g, 607 mmol, 1.3 eq.) in DMF (200 mL) dropwise via addition funnel over 30 minutes. The reaction was completed after stirring for 16 hours as indicated by TLC. The mixture was transferred to a large reaction container and stirred with deionized water (7 gallons) for 24 hours. A yellow precipitate was separated from the mixture by filtration and washed twice with water (100 mL). The solid was purified by silica gel flash column chromatography using $CH_2Cl_2$:MeOH (100/0 to 98/2, v/v) as the eluent. Pooling, concentrating and drying of the appropriate fractions gave 240 g (66%) of the title compound. $^1H$ NMR ($CDCl_3$): δ 1.43 (s, 9H, t-butyl), 3.34 (bs, 4H, 2×$CH_2$), 3.40–3.75 (bm, 16H, 8×$CH_2$), 4.15–4.25 (bs, 4H, 2×$CH_2$), 5.01 (s, 2H, $CH_2$), 5.13 (d, 4H, 2×$CH_2$), 7.39 (m, 10H, aryl), 7.78 (s, 1H, C8H).

Example 11

2,6-Dipiperazinyl-N9-[(N'-t-Boc-N"-acetyl)piperazinyl]purine

[2,6-Dipiperazinyl-(N,N-bis-benzylcarbamate)]-N9-[(N'-t-Boc-N"-acetyl)piperazinyl]purine (2.86 g, 3.65 mmol) was dissolved in MeOH (50 mL) and $CH_2Cl_2$ (30 mL) and transferred to a Parr hydrogenation flask. Pd/C (1.5 g, 10%) was added and the flask was sealed and shaken under $H_2$ (55 psi) for 24 hours. The reaction was completed as indicated by TLC. The mixture was filtered through a bed of celite to remove the Pd/C and concentrated in vacuo to give 1.44 g (77%) of the title compound. $^1H$ NMR (DMSO): δ 1.41 (s, 9H, t-butyl), 2.61–2.83 (bm, 8H, 4×$CH_2$), 3.25–3.35 (bs, 2H, $CH_2$), 3.35–3.50(bs, 4H, 2×$CH_2$), 3.50–3.62(bs, 6H, 3×$CH_2$), 4.89 (s, 2H, $CH_2$), 7.65 (s, 1H, C8H). Mass Spectrum ($ES^+$) m/z 515 [M+H].

Example 12

Library 1, (α-bromoacetamides)

N-(α-Bromoacetyl)-1-aminocycloheptane (541 mg, 2.31 mmol, $L_1$), 2-bromo-N-(3-nitrophenyl)acetamide (236 mg, 0.909 mmol, $L_2$), 2-bromo-N-(4-methoxyphenyl)acetamide (261 mg, 1.07 mmol, $L_3$), 2-bromo-N-(2-benzothiazolyl)acetamide (232 mg, 0.855 mmol, $L_4$), and 2-bromo-N-(furfuryl)acetamide (589 mg, 2.70 mmol, $L_5$) were dissolved in a mixture of DMF and THF (1 mL/0.3 mL). 2,6-Dipiperazinyl-N9-[(N'-t-Boc-N"-acetyl)piperazinyl]purine (1 g, 1.94 mmol) was dissolved in a mixture of DMF and THF (2 mL/3 mL) and diisopropyl-ethylamine (812 mL, 4.66 mmol). This mixture was added dropwise to the mixture of α-bromo compounds above. The vial containing the tri-piperazinyl substituted purine was washed with THF (2×1 mL) and added to the reaction mixture. The reaction was allowed to stir for 2 hours at which time a solution of 2-mercaptoethanesulfonic acid, sodium salt (1.28 g, 7.77 mmol), potassium carbonate (1.07 g, 7.77 mmol) in water (10 mL) was added to quench the excess electrophiles. The mixture was stirred for 1 hour. The reaction mixture was partitioned between water and $CH_2Cl_2$ (20 mL/50 mL). The water layer was extracted twice with $CH_2Cl_2$ (2×20 mL) and the $CH_2Cl_2$ layers were washed once with of brine (50 mL). The $CH_2Cl_2$ was dried ($MgSO_4$), filtered and concentrated in vacuo to leave behind a yellow amorphous solid. The solid was passed through a silica gel column using $MeOH:EtOAc:Cl_2Cl_2$ (5/30/65, v/v/v) as the eluent. The appropriate fractions were collected and concentrated in vacuo to afford 1.47 g (90% yield based on average mass of library) of Library 1. The title Library was also identified by ES/MS (m/z 789, 805, 815, 823, 831, 832, 841, 843, 847, 857, 859, 869, 872, 884, 896).

Example 13

Deprotection of Library 1, preparation of Library 2

Library 1 (1.47 g, 1.74 mmol) was dissolved in 1,4-dioxane (50 mL) and anhydrous HCl gas was bubbled through the solution while stirring at room temperature for 10 minutes. The resulting solution was concentrated in vacuo to leave behind a pink, white solid which was dried over $P_2O_5$ at 90° C. in an abderhalden drying apparatus for 15 hours. The titled deprotected Library was obtained in 71% yield (0.987 g, based on a mono HCl salt and average mass of library). Mass spectrum data were consistent with calculated masses.

Example 14

Preparation of Library 3

Library 2 (102 mg, 0.128 moles based on mono HCl salt) was dissolved in DMF (1.5 mL), THF (3 mL) and diisopropylethylamine (1.5 mL). 2-Bromo-N-(cycloheptyl)-acetamide (34.3 mg, 0.141 mmol, $L_1$) was added to the reaction mixture as a solid. The reaction had gone to completion after 2 hours as indicated by TLC using $NH_4OH:MeOH:EtOAc$ (10/10/80, v/v/v). A solution of 2-mercaptoethanesulfonic acid, sodium salt (49 mg, 0.3 mmol) and potassium carbonate (42 mg, 0.3 mmol) in water (5 mL) was added to quench any excess electrophile. The reaction mixture was partitioned between water (25 mL) and $CH_2Cl_2$ (25 mL). The squeous layer was extracted with $CH_2Cl_2$ (2×15 mL) and the $CH_2Cl_2$ layers were pooled and washed once with brine (25 mL). The $CH_2Cl_2$ layer was dried ($MgSO_4$), filtered and concentrated in vacuo to a yellow amorphous solid. The solid was purified further by silica gel chromatography using $MeOH:EtOAc:CH_2Cl_2$ (5/35/60–10/40/50, v/v/v) as the eluent. The appropriate fractions were collected and concentrated in vacuo to afford the title Library in a 90% yield (101 mg, based on average masses of starting material and product). The title Library was also identified by ES/MS (m/z 843, 860, 871, 876, 885, 886, 896, 897, 901, 911, 913, 923, 926, 938, 950).

Example 15

Preparation of Library 4

Library 2 (100 mg, 0.125 mmoles based on mono HCl salt) was dissolved in DMF (1.5 mL), THF (3 mL) and diisopropylethylamine (1.5). 2-Bromo-N-(3-nitrophenyl)acetamide (37 mg, 0.141 mmol, $L_2$) was added to the reaction mixture as a solid. The reaction was complete by TLC in 2 hours using $NH_4OH$:MeOH:EtOAc (10/10/80, v/v/v) as the eluent. A solution of 2-mercaptoethanesulfonic acid, sodium salt (49 mg, 0.3 mmol), potassium carbonate (42 mg, 0.3 mmol) in water (5 mL) was added to quench any excess electrophile. The reaction mixture was partitioned between water (25 mL) and $CH_2Cl_2$ (25 mL). The water was extracted with $CH_2Cl_2$ (2×15 mL) and the $CH_2Cl_2$ layers were pooled and washed with brine (25 mL). The $CH_2Cl_2$ layer was dried ($MgSO_4$), filtered and concentrated in vacuo to a yellow amorphous solid. The solid was purified further by silica gel chromatography using MeOH:EtOAc:$CH_2Cl_2$ (5/30/60–10/40/50, v/v/v) as the eluent. The appropriate fractions were collected and concentrated in vacuo to afford the title library in 76% yield (89 mg, based on average masses of starting material and product).

The title Library was further identified by EM/MS (m/z 869, 885, 895, 901, 910, 911, 921, 922, 926, 936, 938, 948, 950, 962, 974).

Example 16

Preparation of Library 5

Library 2 (100 mg, 0.125 mmoles based on mono HCl salt) was dissolved in DMF (1.5 mL), THF (3 mL) and diisopropylethylamine (1.5 mL). 2-Bromo-N-(4-methoxyphenyl)acetamide (35 mg, 0.141 mmol, $L_3$) was added to the reaction mixture as a solid. The reaction was complete by TLC $NH_4OH$:MeOH:EtOAc (10/10/80, v/v/v) in 2 hours. A solution of 2-mercaptoethanesulfonic acid, sodium salt (49 mg, 0.3 mmol), potassium carbonate (42 mg, 0.3 mmol) in water (5 mL) was added to quench any excess electrophile. The reaction mixture was partitioned between water (25 mL) and $CH_2Cl_2$ (25 mL). The water was extracted with $CH_2Cl_2$ (2×15 mL) and the $CH_2Cl_2$ layers were pooled and washed with brine (25 mL). The $CH_2Cl_2$ layer was dried ($MgSO_4$), filtered and concentrated in vacuo to a yellow amorphous solid. The solid was purified further by silica gel chromatography using MeOH:EtOAc:$CH_2Cl_2$ (5/35/60–10/40/50, v/v/v) as the eluent. The appropriate fractions were collected and concentrated in vacuo to afford the title library in an 86% yield (72 mg, based on average masses of starting material and product). The title Library was further identified by EM/MS (m/z 854, 870, 880, 886, 895, 896, 906, 907, 911, 921, 923, 933, 936, 948, 960).

Example 17

Preparation of Library 6

Library 2 (100 mg, 0.125 mmoles based on mono HCl salt) was dissolved in DMF (1.5 mL), THF (3 mL) and diisopropylethylamine (1.5 mL). 2-Bromo-N-(2-benzothiazolyl)acetamide (38 mg, 0.141 mmol, $L_4$) was added to the reaction mixture as a solid. The reaction was complete by TLC $NH_4OH$:MeOH:EtOAc (10/10/80, v/v/v) in 2 hours. A solution of 2-mercaptoethanesulfonic acid, sodium salt (49 mg, 0.3 mmol), potassium carbonate (42 mg, 0.3 mmol) in water (5 mL) was added to quench any excess electrophile. The reaction mixture was partitioned between water (25 mL) and $CH_2Cl_2$ (25 mL). The water was extracted with $CH_2Cl_2$ (2×15 mL) and the $CH_2Cl_2$ layers were pooled and washed once with brine (25 mL). The $CH_2Cl_2$ layer was dried ($MgSO_4$), filtered and concentrated in vacuo to a yellow amorphous solid. The solid was purified further by silica gel chromatography using MeOH:EtOAc:$CH_2Cl_2$ (5/35/60–10/40/50, v/v/v) as the eluent. The appropriate fractions were collected and concentrated in vacuo to afford the title Library in an 83% yield (99 mg, based on average masses of starting material and product). The title Library was further identified by EM/MS (m/z 881, 897, 907, 913, 922, 923, 933, 934, 938, 948, 950, 960, 962, 975).

Example 18

Preparation of Library 7

Library 2 (100 mg, 0.125 mmoles based on mono HCl salt) was dissolved in DMF (1.5 mL), THF (3 mL) and diisopropylethylamine (1.5 mL). 2-Bromo-N-(furfuryl)acetamide (31 mg, 0.141 mmol, $L_5$) was added to the reaction mixture as a solid. The reaction was complete by TLC $NH_4OH$:MeOH:EtOAc (10/10/80, v/v/v) in 2 hours. A solution of 2-mercaptoethanesulfonic acid, sodium salt (49 mg, 0.3 mmol), potassium carbonate (42 mg, 0.3 mmol) in water (5 mL) was added to quench any excess electrophile. The reaction mixture was partitioned between water (25 mL) and $CH_2Cl_2$ (25 mL). The water was extracted with $CH_2Cl_2$ (2×15 mL). The $CH_2Cl_2$ layers were pooled and washed with brine (25 mL). The $CH_2Cl_2$ layer was dried ($MgSO_4$), filtered and concentrated in vacuo to a yellow amorphous solid. The solid was purified further by silica gel chromatography using MeOH:EtOAc:$CH_2Cl_2$ (5/35/60–10/40/50, v/v/v) as the eluent. The appropriate fractions were collected and concentrated in vacuo to afford the title Library in a the sub library AMFU (i.e.: AMFU in the fixed position) in a 75% yield (84 mg, based on average masses of starting material and product). The title Library was further identified by EM/MS (m/z 828, 844, 854, 860, 868, 870, 880, 881, 885, 896, 897, 907, 910, 922, 934).

Example 19

Preparation of Library 8, 2-[N-($L_1$–$L_5$)]-Piperazinyl-6-[N-(Trimethylsilylethoxycarbonyl)piperazinyl]-N9-[(N'-t-Boc-N"-acetyl)piperazinyl] purine N-(α-Bromoacetyl)-1-aminocycloheptane (541 mg, 2.31 mmol, $L_1$), 2-bromo-N-(3-nitrophenyl)acetamide (236 mg, 0.909 mmol, $L_2$), 2-bromo-N-(4-methoxyphenyl)acetamide (261 mg, 1.07 mmol, $L_3$), 2-bromo-N-(2-benzothiazolyl)acetamide (232 mg, 0.855 mmol, $L_4$), and 2-bromo-N-(furfuryl)acetamide (589 mg, 2.70 mmol, $L_5$) are dissolved in a mixture of DMF and THF (1 mL/0.3 mL). 2-Piperazinyl-6-[N-(trimethylsilyl-ethoxycarbonyl)piperazinyl]-N9-[(N'-t-Boc-N"-acetyl)-piperazinyl]purine (1.94 mmol) is dissolved in a mixture of DMF and THF (2 mL/3 mL) and diisopropylethylamine (812 mL, 4.66 mmol). This mixture is added dropwise to the mixture of α-bromo compounds($L_1$–$L_5$) above. The vial containing the tri-piperazinyl substituted purine is washed with THF (2×1 mL) and added to the reaction mixture. The reaction is allowed to stir for 2 hours at which time a solution of 2-mercaptoethanesulfonic acid, sodium salt (1.28 g, 7.77 mmol), potassium carbonate (1.07 g, 7.77 mmol) in water (10 mL) water is added to quench the excess electrophiles. The mixture is stirred for 1 hour. The reaction mixture is partitioned between water and $CH_2Cl_2$ (20 mL/50 mL). The water layer is extracted twice with $CH_2Cl_2$ (2×20 mL) and the $CH_2Cl_2$ layers are washed once with of brine (50 mL). The $CH_2Cl_2$ layer is dried ($MgSO_4$), filtered and concentrated to give the crude product. The crude product is purified by silica gel flash column chromatography using an appropriate solvent mixture as the eluent (e.g. MeOH:EtOAc:$CH_2Cl_2$ (5/30/65, v/v/v)). The appropriate fractions are collected and concentrated to afford the title library.

Example 20

Preparation of Library 9, 2-[N-($L_1$–$L_5$)]-Piperazinyl-6-[N-piperazinyl]-N9-[(N'-t-Boc-N"-acetyl)piperazinyl]purine The trimethylsilylethoxycarbonyl protecting group is removed from Library 8 following the procedures illustrated in Example 8 Method B to give the title library.

Example 21

Preparation of Library 10, 2-[N-($L_1$–$L_5$)]-Piperazinyl-6-[N-$L_1$-piperazinyl]-N9-[(N'-t-Boc-N"-acetyl)piperazinyl]purine Library 9 is treated as per the procedures of Example 14 to give the title library.

Example 22

Preparation of Library 11, 2-[N-($L_1$–$L_5$)-Piperazinyl-6-[N-$L_1$-piperazinyl]-N9-(N-acetylpiperazinyl)purine The t-Boc protecting group of Library 10 is removed as per the procedure of Example 13 to give the title Library.

Example 23

Preparation of Library 12, 2-[N-($L_1$–$L_5$)]-Piperazinyl-6-[N-$L_1$-piperazinyl]-N9-[(N'-$L_2$-N"-acetyl)piperazinyl]purine Library 11 is treated as per the procedures of Example 15 to give the title Library.

Example 24

2,6-[Di-(N-$L_1$ and $L_4$–$L_{12}$-dipiperazinyl)]-N9-[(N'-t-Boc-N"-acetyl)piperazinyl]purine, Preparation of Library 13

2,6-Dipiperazinyl-N9-[(N'-t-Boc-N"-acetyl)-piperazinyl] purine (1 g, 1.94 mmol) was dissolved in a mixture of MeOH:THF (3 mL/3 mL, and diisopropylethylamine (1.1 eq. 2.14 mmol, 372 μL). To this solution was added a solution of 5 benzylbromides prepared by mixing together standard solutions (2.33 mL, 389 μMoles) of m-chlorobenzylbromide ($L_6$), m-cyanobenzylbromide ($L_7$), m-nitrobenzylbromide ($L_8$), m-methylesterbenzylbromide ($L_9$), and m-triflouromethylbenzylbromide ($L_{10}$) in MeOH (167 mL) in one portion. The reaction was completed after stirring for 24 hours as indicated by TLC.

To the reaction mixture was added diisopropylethylamine (812 μl, 4.66 mmol) followed by a solution of 5 α-bromoacetamides prepared by mixing together weighted amounts of each α-bromoacetamide in THF (3 mL). The equivalent amount of each α-bromoacetamide used was based on the apparent rate constant as illustrated in examples 81–87. The amounts used were: 2-bromo-N-(cycloheptyl) acetamide (328 mg, 1.4 mmol, $L_1$), 2-bromo-N-(furfuryl) acetamide (268 mg, 1.23 mmol, $L_5$), N-(α-bromoacetyl)-2-aminobenzothiazole (116 mg, 0.427 mmol, $L_4$), 2-bromo-N-(3-5'-methylisoxazolyl)acetamide (113 mg, 0.514 mmol, $L_{11}$), and 2-bromo-N-(1,2,3,4-tetrahydroisoquinoline) acetamide (351 mg, 3.387 mmol, $L_{12}$). The TLC showed disappearance of the 2,6-dipiperazinyl-N9-[(N'-t-Boc-N"-acetyl)piperazinyl]purine after 3 hours.

The reaction mixture was quenched by addition of a quenching solution that was prepared by stirring 2-mercaptoethane sulfonic acid (638 mg, 3.89 mmol, 2 eq.) and $K_2CO_3$ (37 mg, 3.89 mmol, 2 eq.) in $H_2O$ (10 mL) for 2 hours. The reaction mixture was concentrated to a volume of about 7 to 10 mL and partitioned between $CH_2Cl_2$ and water (10 mL/10 mL). The water layer was extracted twice with $CH_2Cl_2$ (15 mL) and the pooled $CH_2Cl_2$ layers were washed once with a brine solution (15 mL). The $CH_2Cl_2$ layer was dried ($MgSO_4$), filtered and concentrated. The title library was obtained in 96% yield (1.50 g) based on the average mass of the library.

Example 25

2,6-[Di-(N-$L_1$ and $L_4$–$L_{12}$-dipiperazinyl)]-N9-[(N-acetyl)-piperazinyl]purine, deprotection of Library 13, preparation of Library 14

Library 13 (1.50 g, 1.85 mmol) was dissolved in a solution of $CH_2Cl_2$:MeOH (0.5 mL/0.5 mL) and HCl (5 mL, 5N) was added. The mixture was stirred for 1.5 hours, concentrated and dried on high vacuum to give the crude library as a brown solid. A sample of the crude library was submitted as an HCl salt for mass spectrum analysis. The remainder of the crude library was neutralized with dowex G-55 OH strongly basic resin. The mixture was dissolved in MeOH (20 mL) and 5 g of the above resin was added; The pH of the reaction mixture was tested with pH paper and was found to be basic (~pH 8). The resin was filtered and the solvent was removed in vacuo to give 810 mg (62%) of the neutralized Library 13 as a yellowish brown foam (based on the average mass of the library). A sample of the neutralized library was also submitted for Mass spectrum analysis. Mass spectrum (ES/MS⁺) data of both samples, before and after neutralization, were consistent with theoretical expectations. The product mixture has 55 different masses for 100 different compounds with greater than 95% of the desired masses found in both of the spectra.

Example 26

General procedure for alkylation of the N9-acetylpiperazinyl amino position with a letter, 2,6-[Di-(N-$L_1$ and $L_4$–$L_{12}$-dipiperazinyl)]-N9-[(N'-$L_1$-N"-acetyl)piperazinyl]purine, preparation of Library 15

2-Bromo-N-(cycloheptyl)acetamide (18 mg, 92 μmol, $L_1$) was added to a solution of Library 14 (50 mg, 71 μmol) dissolved in THF (3 mL) and diisopropylethylamine (16 μl). After 2 hours the reaction was completed as indicated by TLC using $NH_4OH$:MeOH:EtOAc (10/10/80, v/v/v). A solution of 2-mercaptoethanesulfonic acid, sodium salt (12 mg, 71 μmol) and potassium carbonate (10 mg, 71 μmol) in water (5 mL) was added to quench any excess electrophile. The reaction mixture was partitioned between water (25 mL) and $CH_2Cl_2$ (25 mL). The water was separated and extracted with $CH_2Cl_2$ (2×15 mL). The combined $CH_2Cl_2$ layers were washed with brine (25 ml), dried ($MgSO_4$), filtered and concentrated to give a yellow amorphous solid. The solid was purified by silica gel flash column chromatography using $MeOH:EtOAc:CH_2Cl_2$ (5/35/60–10/40/50, v/v/v) as the eluent. The appropriate fractions were combined, concentrated and dried under high vacuum to give 49 mg (80%) of Library 15 (based on the average masses of starting material and product). Mass spectrum data (ES/MS) of the product mixture show greater than 95% of the desired masses.

Example 27

General procedure for alkylation of the N9-acetylpiperazinyl amino position with a letter, 2,6-[Di-(N-$L_1$ and $L_4$–$L_{12}$-dipiperazinyl)]-N9-[(N'-$L_8$-N"-acetyl)piperazinyl]purine, preparation of Library 16 m-Nitrobenzylbromide (20 mg, 92 $\mu$mol, $L_8$) was added to a solution of Library 14 (50 mg, 71 $\mu$mol) dissolved in THF (3 mL) and diisopropylethylamine (16 $\mu$l). After 2 hours the reaction was completed as indicated by TLC using $NH_4OH:MeOH:EtOAc$ (10/10/80, v/v/v). A solution of 2-mercaptoethanesulfonic acid, sodium salt (12 mg, 71 $\mu$mol) and potassium carbonate (10 mg, 71 $\mu$mol) in water (5 mL) was added to quench any excess electrophile. The reaction mixture was partitioned between water (25 mL) and $CH_2Cl_2$ (25 mL). The water was separated and extracted with $CH_2Cl_2$ (2×15 mL). The combined $CH_2Cl_2$ layers were washed with brine (25 mL), dried ($MgSO_4$), filtered and concentrated to give a yellow amorphous solid. The solid was purified by silica gel flash column chromatography using $MeOH:EtOAc:CH_2Cl_2$ (5/35/60–10/40/50, v/v/v) as the eluent. The appropriate fractions were combined, concentrated and dried under high vacuum to give 50 mg (83%) of Library 16 (based on the average masses of starting material and product). Mass spectrum data (ES/MS) of the product mixture show greater than 95% of the desired masses.

Example 28

2,6-[Di-(N-$L_1$ and $L_4$–$L_{12}$-dipiperazinyl)]-N9-[(N'-$L_5$-N"-acetyl)-piperazinyl]-[(N-acetyl)piperazinyl] purine, preparation of Library 17

The title library was prepared as per the procedures illustrated in examples 26 and 27 using 2-bromo-N-(furfuryl)acetamide ($L_5$).

Example 29

2,6-[Di-(N-$L_1$ and $L_4$–$L_{12}$-dipiperazinyl)]-N9-[(N'-$L_4$-N"-acetyl)-piperazinyl]-[(N-acetyl)piperazinyl] purine, preparation of Library 18

The title library was prepared as per the procedures illustrated in examples 26 and 27 using 2-bromo-N-(2-benzothiazolyl)acetamide ($L_4$).

Example 30

2,6-[Di-(N-$L_1$ and $L_4$–$L_{12}$-dipiperazinyl)]-N9-[(N'-$L_{11}$-N"-acetyl)piperazinyl]-[(N-acetyl)piperazinyl] purine, preparation of Library 19

The title library was prepared as per the procedures illustrated in examples 26 and 27 using 2-bromo-N-(3-5'-methylisoxazolyl)acetamide(–$L_{11}$).

Example 31

2,6-[Di-(N-$L_1$ and $L_4$–$L_{12}$-dipiperazinyl)]-N9[(N'-$L_{12}$-N"-acetyl)piperazinyl]-[(N-acetyl)piperazinyl] purine, preparation of Library 20

The title library was prepared as per the procedures illustrated in examples 26 and 27 using 2-bromo-N-(1,2,3,4-tetrahydroisoquinoline)acetamide-$L_{12}$).

Example 32

2,6-[Di-(N-$L_1$ and $L_4$–$L_{12}$-dipiperazinyl)]-N9-[(N'-$L_6$-N"-acetyl)-piperazinyl]-[(N-acetyl)piperazinyl] purine, preparation of Library 21

The title library was prepared as per the procedures illustrated in examples 26 and 27 using m-chlorobenzylbromide ($L_6$).

Example 33

2,6-[Di-(N-$L_1$ and $L_4$–$L_{12}$-dipiperazinyl)]-N9-(N'-$L_7$-N"-acetyl)-piperazinyl]-[(N-acetyl)piperazinyl] purine, preparation of Library 22

The title library was prepared as per the procedures illustrated in examples 26 and 27 using m-cyanobenzylbromide ($L_7$).

Example 34

2,6-[Di-(N-$L_1$ and $L_4$–$L_{12}$-dipiperazinyl)]-N9-[(N'-$L_9$-N"-acetyl)-piperazinyl]-[(N-acetyl)piperazinyl] purine, preparation of Library 23

The title library was prepared as per the procedures illustrated in examples 26 and 27 using m-methylesterbenzylbromide ($L_9$).

Example 35

2,6-[Di-(N-$L_1$ and $L_4$–$L_{12}$-dipiperazinyl)]-N9-[(N'-$L_{10}$-N"-acetyl)piperazinyl]-[(N-acetyl)piperazinyl] purine, preparation of Library 24

The title library was prepared as per the procedures illustrated in examples 26 and 27 using m-triflouromethylbenzylbromide ($L_{10}$)

Example 36

2,6-[Di-(N-$L_1$ and $L_4$–$L_{12}$-dipiperazinyl)]-N9-[(N'-$L_{13}$-N"-acetyl)piperazinyl]-[(N-acetyl)piperazinyl] purine, preparation of Library 25

The title library was prepared as per the procedures illustrated in examples 26 and 27 using adamantane-1-carborbonyl chloride ($L_{13}$).

Example 37

2,6-[Di-(N-$L_1$ and $L_4$–$L_{12}$-dipiperazinyl)]-N9-(N'-$L_{14}$-N"-acetyl)piperazinyl]-[(N-acetyl)piperazinyl] purine, preparation of Library 26

The title library was prepared as per the procedures illustrated in examples 26 and 27 using bromoacetonitrile ($L_{14}$).

Example 38

2,6-[Di-(N-$L_1$ and $L_4$–$L_{12}$-dipiperazinyl)]-N9-[(N'-$L_{15}$-N"-acetyl)piperazinyl]-[(N-acetyl)piperazinyl] purine, preparation of Library 27

The title library was prepared as per the procedures illustrated in examples 26 and 27 using propargyl bromide ($L_{15}$)

Example 39

2-(N-$L_1$, $L_4$-$L_{12}$) Piperazinyl-6-[N-(trimethylsilyl-ethoxycarbonyl)piperazinyl]-N9-[(N'-t-Boc-N"-acetyl)-piperazinyl]purine, preparation of Library 28

To a solution of 2-piperazinyl-6-[N-(trimethylsilylethoxycarbonyl)piperazinyl]-N9-[(N'-t-Boc-N"-acetyl)piperazinyl]purine (2.14 g, 3.25 μmol) in THF (30 mL) and diisopropylethylamine (735 μl, 4.22 μmol) was added one tenth of an equivalent of m-chlorobenzylbromide (53 μL, $L_6$), m-cyanobenzylbromide (64 mg, $L_7$), m-nitrobenzylbromide (70 mg, $L_8$), m-methylesterbenzylbromide (74 mg, $L_9$), m-triflouromethylbenzylbromide (50 μl, $L_{10}$) 2-bromo-N-(1,2,3,4-tetrahydroisoquinoline)acetamide (83 mg, $L_{12}$), 2-bromo-N-(3-5'-methylisoxazolyl)acetamide (71 mg, $L_5$), 2-bromo-N-(furfuryl)acetamide (71 mg, $L_5$) 2-bromo-N-(cycloheptyl)acetamide (76 mg, $L_1$) and 2-bromo-N-(2-benzothiazolyl)acetamide (88 mg, $L_4$). The addition of the ten active letters to the scaffold was made simultaneously. The reaction went to completion after 20 hours as indicated by TLC using MeOH:EtOAc (10/90, v/v). A solution of 2-mercaptoethanesulfonic acid sodium salt (532 mg, 3.25 μmol) and potassium carbonate (449 mg, 3.25 μmol) in water (10 mL) was added to quench any excess electrophile. The reaction mixture was partitioned between water (40 mL) and $CH_2Cl_2$ (40 mL). The water layer was separated and extracted with $CH_2Cl_2$ (2×25 mL). The $CH_2Cl_2$ layers were combined, washed with brine (25 mL), dried ($MgSO_4$), filtered and concentrated to give 1.92 g (74% based on average formula weight of library) of the title library as a yellow amorphous solid.

Example 40

2-(N-$L_1$, $L_4$-$L_{12}$) Piperazinyl-6-piperazinyl-N9-[(N'-t-Boc-N"-acetyl)piperazinyl]purine, deprotection of Library 28, preparation of Library 29

Library 28 (1.92 g) was dissolved in THF (100 mL) and tetrabutylammoniumflouride (TBAF) on silica (1.1 mmol/g, 2.38 g, 10 eq.) was added in one portion. The reaction had gone to completion after stirring for 20 hours as indicated by TLC using MeOH:$NH_4OH$:EtOAc (5/5/90/, v/v/v). The reaction mixture was filtered through a bed of celite and concentrated. The resultant oil was purified by silica gel flash column chromatography using MeOH:$NH_4OH$:THF (5/5/90, v/v/v) as the eluent. The appropriate fractions were pooled, concentrated and dried on high vacuum to give 735 mg (55%) of the title library. Mass spectrum data: (ES/MS$^+$) m/z 528, 538, 548, 550, 551, 561, 566, 571, 586, 603.

Example 41

2-(N-$L_1$, $L_4$-$L_{12}$)Piperazinyl-6-[N-(m-nitrobenzyl)piperazinyl]-N9-[(N'-t-Boc-N"-acetyl)piperazinyl]purine, general procedure for alkylation of the 6-piperazinyl position, preparation of Library 30 m-Nitrobenzylbromide (21.5 mg, 99.6 μmol, $L_8$) was added to solution of Library 29 (60 mg, 91 μmoles) dissolved in THF (3 mL) and diisopropylethylamine (22 μl). The reaction had gone to completion after stirring for 2 hours as indicated by TLC using MeOH:$NH_4OH$:EtOAc (5/5/90/, v/v/v). A solution of 2-mercaptoethanesulfonic acid, sodium salt (15 mg, 90 μmol) and potassium carbonate (13 mg, 90 μmol) in water (3 mL) was added to quench any excess electrophile. The reaction mixture was partitioned between water (20 mL) and $CH_2Cl_2$ (20 mL). The water layer was separated and extracted with $CH_2Cl_2$ (2×15 mL). The $CH_2Cl_2$ layers were combined, washed with brine (25 mL)), dried ($MgSO_4$), filtered and concentrated to a yellow amorphous solid. The solid was purified by silica gel flash column chromatography using MeOH:EtOAc:$CH_2Cl_2$ (5/35/60, v/v/v) as the eluent. The appropriate fractions were combined and concentrated to give 60 mg (90%) of the title library. Mass spectrum data: (ES/MS+) m/z 664, 674, 684, 686, 688, 697, 702, 709, 723, 740.

Example 42

2-(N-$L_1$, $L_4$–$L_{12}$)Piperazinyl-6-[N-($L_n$)piperazinyl]-N9-[(N'-t-Boc-N"-acetyl) piperazinyll purine, general procedure for alkylation of the 6-piperazinyl position, preparation of Libraries 31–39

Following the procedures illustrated in Example 41, 9 additional libraries were synthesized. The synthesis of libraries 31–39 employed using one of 2-bromo-N-(cycloheptyl)acetamide ($L_1$), 2-bromo-N-(2-benzothiazolyl)acetamide ($L_4$), 2-bromo-N-(furfuryl)acetamide ($L_5$), m-chlorobenzylbromide ($L_6$), m-cyanobenzylbromide ($L_7$), m-methylesterbenzylbromide ($L_9$), m-triflouromethylbenzyl-bromide ($L_{10}$), 2-bromo-N-(1,2,3,4-tetrahydroisoquinoline)acetamide ($L_{12}$) or 2-bromo-N-(3-5'-methylisoxazolyl)acetamide ($L_{11}$), respectively, in place of the m-nitrobenzylbromide ($L_8$) used in Example 41. The mass spectrum determined for each library was consistent with theoretical expectations.

Example 43

6-Piperazinyl-2-[N-(trimethylsilyletboycarbonyl)-piperazinyl]-N9-[(N'-t-Boc-N"-acetyl)piperazinyl] purine

2-(Trimethylsilyl)ethyl-p-nitrophenyl carbonate (3.30 g, 11.65 mmol) was added to a solution of 2,6-dipiperazinylpurine (6 g, 11.65 mmol) in DMF (600 mL) and diisopropylethylamine (2.44 mL, 14 mmol). The reaction had gone to completion after 20 hours as indicated by TLC (using MeOH:$NH_4OH$:EtOAc (5/5/90, v/v/v). The TLC showed that the 4 expected products were present (2-piperazinyl-6-[N-(tri-methylsilylethoxycarbonyl)piperazinyl]-N9-[(N'-t-Boc-N"-acetyl)piperazinyl]purine, the desired product N6-piperazinyl-2-[N-(trimethylsilylethoxycarbonyl)piperazinyl]-N9-[(N'-t-Boc-N"-acetyl)piperazinyl]purine, starting material 2,6-dipiperazinylpurine and N6-N2-{Bis[N-(trimethylsilylethoxycarbonyl)piperazinyl]-N9-[(N'-t-Boc-N"-acetyl)piperazinyl]purine. The reaction mixture was concentrated to a yellow oil. The oil was purified by silica gel flash column chromatography using MeOH:$CH_2Cl_2$ (5/95, v/v) to elute p-nitrophenol and the bis protected material. The column was then dried by passing Ar through the silica gel for 30 minutes. The title compound was eluted from the column using MeOH:$NH_4OH$:THF (5/5/90, v/v/v) as the eluent. The appropriate fractions were collected and concentrated to give 877 mg (46%) of the title compound.

Example 44

6-[(2-Aminobenzothiazole acetyl)piperazinyl]-2-[N-(tri-methylsilylethoxycarbonyl)piperazinyl]-N9-[(N'-t-Boc-N"-acetyl)piperazinyl]purine

2-Bromo-N-(2-benzothiazolyl)acetamide (217 mg, 801 μmol) was added to a solution of N6-piperazinyl-2-[N-

(trimethylsilylethoxycarbonyl)piperazinyl]-N9-[(N'-t-Boc-N''-acetyl)piperazinyl]purine (440 mg, 668 μmol) in THF (20 mL) and diisopropylethylamine (163 μL, 935 μmol). The reaction went to completion after 16 hours as indicated by TLC using MeOH:NH$_4$OH:EtOAc (5/5/90, v/v/v). The reaction mixture was partitioned between water (20 mL) and CH$_2$Cl$_2$ (30 mL). The water layer was separated and extracted CH$_2$Cl$_2$ (2×15 mL). The combined CH$_2$Cl$_2$ layers were washed with brine (25 mL), dried (MgSO$_4$), filtered and concentrated to a yellow amorphous solid. The solid was purified further by silica gel flash column chromatography using MeOH:EtOAc:CH$_2$Cl$_2$, (5/35/60, v/v/v) as the eluent. The appropriate fractions were collected and concentrated to give 509 mg (90%) of title compound. $^1$H NMR (CDCl$_3$): δ 0.04 (s, 9H, Me$_3$Si), 1.20 (m, 2H, CH$_2$), 1.48 (s, 9H, t-butyl), 2.78 (bs, 4H, 2×CH$_2$), 3.37 (s, 2H, CH$_2$), 3.43 (m, 4H, 2×CH$_2$), 3.57 (m, 4H, 2×CH$_2$), 3.61 (m, 4H, 2×CH$_2$), 3.75 (m, 4H, 2×CH$_2$), 4.22 (m, 2H, CH$_2$), 4.35 (m, 4H, 2×CH$_2$), 4.90 (s, 2H, N9—CH$_2$), 7.22 (CDCl$_3$), 7.37 (t, 1H, Ar), 7.44 (t, 1H, Ar), 7.61 (s, 1H, C$_8$H), 7.82 (t, 1H, Ar), 10.48 (bs, 1H, amide NH).

Example 45

6-[(2-Aminobenzothiazole acetyl)piperazinyl]-2-piperazinyl-N9-[(N'-t-Boc-N''-acetyl)piperazinyl]purine TBAF on silica (1.1 mmol/g, 5.35 g, 5.89 mmol) was added to a solution of 6-[(2-aminobenzothiazole acetyl)piperazinyl]-2-[N-(trimethylsilylethoxycarbonyl)piperazinyl]-N9-[(N'-t-Boc-N''-acetyl)piperazinyl]purine (500 mg, 598 μmol) in THF (50 mL). $^1$H NMR (CDCl$_3$): δ 1.45 (s, 9H, t-butyl), 2.71 (bs, 4H, 2×CH$_2$), 2.95 (bs, 4H, 2×CH$_2$), 3.37 (s, 2H, CH$_2$), 3.40 (bs, 4H, 2×CH$_2$), 3.59 (bs, 4H, 2×CH$_2$), 3.78 (bs, 4H, 2×CH$_2$), 4.88 (s, 2H, CH$_2$), 7.23 (CDCl$_3$), 7.37 (t, 1H, Ar), 7.44 (t, 1H, Ar), 7.61 (S, 1H, C$_8$H), 7.82 (t, 1H, Ar).

Example 46

General procedure for alkylation at the 2-piperazinyl postition, 6-[(2-aminobenzothiazole acetyl)piperazinyl]-2-[(m-chlorobenzyl)-piperazinyl]-N9-[(N'-t-Boc-N''-acetyl)piperazinyl]purine m-Chlorobenzylbromide (6.3 μl, 56 μmol) was added to a solution of 6-[(2-aminobenzothiazole acetyl)piperazinyl]-2-piperazinyl-N9-[(N'-t-Boc-N''-acetyl)piperazinyl]purine (28 mg, 40 μmol) in THF (3 mL) and diisopropylethylamine (10 μl, 56 μmol). The reaction went to completion after stirring for 20 hours as indicated by TLC using MeOH:NH$_4$OH:EtOAc (5/5/90, v/v/v). The reaction mixture was concentrated and the resultant residue purified by silica gel flash column chromatography using MeOH:EtOAc:CH$_2$Cl$_2$, (5/5/90, v/v/v) as the eluent. The appropriate fractions were combined, concentrated and dried on high vacuum to give a residue of the title compound. To the residue dissolved in a mixture of CH$_2$Cl$_2$ and MeOH (0.5 mL each) was added HCl (5 mL, 5 N/MeOH). The mixture was stirred for 1.5 hours and concentrated to give 26 mg (86%, based on mono HCl salt) of the title compound as the HCl salt. Mass spectrum data: (FAB+) exact/unit mass (ie. C$_{60}$=720.0000), mass expected: 729.2963, Mass observed: 729.2989.

Example 47

6-[(2-Aminobenzothiazole acetyl)piperazinyl]-2-[(N-m-cyano-benzyl)piperazinyl]-N9-[(N'-t-Boc-N''-acetyl)piperazinyl]purine The title compound was prepared following the general procedure illustrated in Example 46, using m-cyanobenzylbromide (L$_7$) as the alkylating agent. Isolated 25 mg (83%, based on the mono HCl salt). Mass spectrum data: (FAB+) exact/unit mass (ie. C$_{60}$=720.0000), mass expected: 720.3305; mass observed: 720.3280.

Example 48

6-[(2-Aminobenzothiazole acetyl)piperazinyl]-2-[(N-m-nitrobenzyl)piperazinyl]-N9-[(N'-t-Boc-N''-acetyl)piperzinyl]purine The title compound was prepared following the general procedure illustrated in Example 46, using m-nitrobenzylbromide (L$_8$) as the alkylating agent and 29 mg (94%, based on the mono HCl salt) of product was isolated. Mass spectrum data: (FAB+) exact/unit mass (ie. C$_{60}$=720.0000), mass expected: 740.3203; mass observed: 740.3179.

Example 49

6-[(2-Aminobenzothiazole acetyl)piperazinyl]-2-[(N-methyl-esterbenzyl)piperazinyl]-N9-[(N'-t-Boc-N''-acetyl) piperzinyl]purine The title compound was prepared following the general procedure illustrated in Example 46, using m-methylesterbenzylbromide (L$_9$) as the alkylating agent and 18mg (58%, based on the mono HCl salt) of product was isolated. Mass spectrum data: (FAB+) exact/unit mass (ie. C$_{60}$=720.0000), mass expected: 753.3407; mass observed: 753.3431.

Example 50

6-[(2-Aminobenzothiazole acetyl)piperazinyl]-2-[(N-m-triflouromethylbenzyl)piperazinyl]-N9-[(N'-t-Boc-N''-acetyl)piperazinyl]purine The title compound was prepared following the general procedure illustrated in Example 46, using m-triflouromethylbenzylbromide (L$_{10}$) as the alkylating agent and 26 mg (84%, based on the mono HCl salt) of product was isolated. Mass spectrum data: (FAB+) exact/unit mass (ie. C$_{60}$=720.0000), (M+Cs+) mass expected: 895.2203; mass observed: 895.2175.

Example 51

6-[(2-Aminobenzothiazole acetyl)piperazinyl]-2-[(N-acetyl-tetrahydroisoquinoline)piperazinyl]-N9-[(N'-t-Boc-N''-acetyl)piperazinyl]purine The title compound was prepared following the general procedure illustrated in Example 46, using 2-bromo-N-(1,2,3,4-tetrahydroisoquinoline)acetamide (L$_{12}$) as the alkylating agent and 25 mg (81%, based on the mono HCl salt) of product was isolated. Mass spectrum data: (FAB+) exact/unit mass (ie. C$_{60}$=720.0000), (M+) mass expected: 778.3724; mass observed: 778.3750.

Example 52

6-1(2-Aminobenzothiazole acetyl)piperazinyl]-2-[(N-(acetyl)-3-amino-5-methylisoxazole) piperazinyl]-N9-[(N'-t-Boc-N''-acetyl)piperazinyl]purine The title compound was prepared following the general procedure illustrated in Example 46, using 2-bromo-N-(3-

5'-methylisoxazolyl)acetamide ($L_{11}$) as the alkylating agent and 26 mg (84%, based on the mono HCl salt) of product was isolated. Mass spectrum data: (FAB+) exact/unit mass (ie. $C_{60}$=720.0000), (M+) mass expected: 743.3312; mass observed: 743.3340.

Example 53

6-[(2-Aminobenzothiazole acetyl)piperazinyl]-2-[(acetyl)-1-aminocycloheptane)piperazinyl]-N9-[(N'-t-Boc-N"-acetyl)-piperazinyl]purine The title compound was prepared following the general procedure illustrated in Example 46, using 2-bromo-N-(cycloheptyl)acetamide ($L_1$) as the alkylating agent and 30 mg (94%, based on the mono HCl salt) of product was isolated. Mass spectrum data: (FAB+) exact/unit mass (ie. $C_{60}$=720.0000), (M+) mass expected: 758.4037; mass observed: 758.4069.

Example 54

2,6-[Bis-(2-aminobenzothiazole acetyl)piperazinyl]-N9-[(N'-t-Boc-N"-acetyl) piperazinyl]purine The title compound was prepared following the general procedure illustrated in Example 46, using 2-bromo-N-(2-benzothiazolyl)acetamide ($L_4$) as the alkylating agent and 31 mg (94%, based on the mono HCl salt) of product was isolated. Mass spectrum data: (FAB+) exact/unit mass (ie. $C_{60}$=720.0000), (M+) mass expected: 795.3084, mass observed: 795.3052.

Example 55

6-[(2-Aminobenzothiazole acetyl)piperazinyl]-2-piperazinyl-N9-(acetyl piperazinyl) purine HCl (5 mL, 5N/MeOH) was added to a solution of 6-[(2-aminobenzothiazole acetyl)piperazinyl]-2-piperazinyl-N9-[(N'-t-Boc-N"-acetyl)piperazinyl]purine (28 mg, 40 µmol) in $CH_2Cl_2$:MeOH (0.5 mL each). The reaction mixture was stirred for 1.5 hours and concentrated to give 21 mg (84%, based on mono HCl salt) of the title compound as the HCl salt. Mass spectrum data: (FAB+) exact/unit mass (ie. $C_{60}$=720.0000), mass expected: 605.2883, mass observed: 605.2859.

Examples 56–88

The purity and commercial source of reagents for Examples 56–88 are as follows: Formic acid (98%), N,N-dimethylisopropylamine (>98%) and bromoacetyl bromide were purchased from Fluka. MeOH (ACS reagent) was purchased from Baker. (+−)-Dropropizine was purchased from Sigma Chemical Co. THF (sure-seal), DMF (sure-seal), diisopropyl-ethylamine, 1-phenylpiperazine, cycloheptylamine, furfurylamine, 4-methoxyaniline, 3-nitroaniline, 1,2,3,4-tetrahydroisoquinoline hydrochloride, 2-amino-4-methylthiazole, 2-bromoacetamide (Br-$L_{17}$), and 1-bromo-2-butanone (technical grade 90%) (Br-$L_{18}$) were purchased from Aldrich Chemical Co. 2-Aminobenzothiazole and 3-amino-5-methylisoxazole were purchased from Lancaster Synthesis Inc. 6-(Bromoacetyl)-2-oxo-1,2,3,4-tetrahydroquinoline (Br-$L_{20}$), 2-(bromoacetyl)-5-chloro-3-methylbenzo[b]thiophene (Br-$L_{21}$), 6-(bromoacetyl)-1,2,3,4-tetrahydro-1,1,4,4-tetramethyl-naphthalene (Br-$L_{19}$), 5-(bromomethyl) benzofurazan (Br-$L_{22}$), 3-(bromomethyl)-5-chlorobenzo[b]thiophene (Br-$L_{23}$), 6-(bromo-methyl)-4-chloro-2-trifluoromethyl)quinoline (Br-$L_{24}$) and 4-(4-bromomethylphenyl)-1,2,3-thiadiazole (Br-$L_{25}$) were purchased from Maybridge Chemical Co. Rotary evaporations were performed in vacuo (50 torr) at 35° C. unless otherwise noted. NMR was performed on a Varian Gemini 200 or Varian Unity 400. Mass spectral data were taken on a Hewlett Packard 59987A electrospray mass spectrometer (quadrupole mass analyzer 0–2600 amu). One procedure for performing capillary electrophoresis (Set 1) utilized an Applied Biosystems 270A capillary electrophoresis system under the following conditions: detection wavelength of 214 nm, fused-silica capillary (60 cm×50 µm i.d., 50 cm to detector), capillary and samples at ambient temperature, samples injected under vacuum of 5 in. for 5 seconds analysis voltage of 30 kV, between analyses capillaries flushed for 2 minutes with electrophoresis medium, buffer: 20 mM ammonium acetate, 94% MeOH (reagent grade), 0.75% formic acid, 5% water. Another procedure for performing capillary electrophoresis (Sets 2–5) utilized a Beckman P/ACE system 5500 equipped with diode array detector under the following conditions: detection wavelength of 214 nm, fused-silica capillary (47 cm×75 µm i.d., 40 cm to detector), samples injected under pressure of 5 kPa for 6 seconds analysis voltage of 25 kV, capillary at 16° C., between analyses capillaries flushed for 2 minutes with electrophoresis medium, buffer: 10 mM ammonium acetate, 95% MeOH, 0.2% formic acid, 5% water. Absorbances were represented by areas and each CZE was repeated twice with the averaged values used for further determinations.

Example 56

2-Bromo-N-(cycloheptyl)acetamide (Br-$L_1$) (compound 1)

To a −20° C. solution of cycloheptylamine (6.37 mL, 50.0 mmol) and diisopropylethylamine (9.58 mL, 55.0 mmol) in $CH_2Cl_2$ (250 mL) was slowly added bromoacetyl bromide (4.78 mL, 55.0 mmol). The reaction mixture was warmed to room temperature over 20 minutes and stirred for an additional 30 minutes. The reaction mixture was diluted with water (100 mL) and stirred for an additional 30 minutes. The organic layer was separated, washed with water (3×100 mL), dried over magnesium sulfate and concentrated in vacuo to afford a beige solid (10.5 g). The crude material was further purified by silica gel flash column chromatography using hexane:ethyl acetate (1/1, v/v) as the eluent to give the purified title compound as an oil (9.77 g, 83%). $^1$H-NMR ($Me_2SO$-$d_6$): δ 8.20 (br d, 1H), 3.77 (s, 2H), 3.67 (m, 1H) and 1.8–1.3 (m, 12H). $^{13}$C-NMR ($CDCl_3$): δ 164.01, 51.04, 34.59, 29.40, 27.80 and 23.87. Mass spectrum (FAB+) m/z 234/236 [M+H]$^+$ and 256/258 [M+Na]$^+$.

Example 57

2-Bromo-N-(furfuryl)acetamide (Br-$L_5$) (compound 2)

The title compound was prepared as per the procedures illustrated in Example 56. Furfurylamine (9.10 mL, 103 mmol), dry $CH_2Cl_2$ (200 mL), diisopropylethylamine (20 mL, 113 mmol), and bromoacetyl bromide (9.84 mL, 113 mmol) gave after work-up an oil which was purified by flash chromatography using $CH_2Cl_2$:EtOAc (100:1, v/v) to give the title compound as a beige solid (9.67 g, 88%). $^1$H-NMR ($CDCl_3$): δ 7.37 (m, 1H), 6.34 (m, 1H), 6.26 (m, 1H), 4.47 (d, 2H), 3.90 (s, 2H). $^{13}$C-NMR ($CDCl_3$): δ 165.3, 150.5, 142.5, 110.5, 108.0, 37.0, 29.0. Mass spectrum (FAB+) m/z 218/220 [M+H]+.

Example 58

2-Bromo-N-(4-methoxyphenyl)acetamide (Br-L$_3$) (compound 3)

The title compound (Vloon, W. J.; et al., *J. Med. Chem.*, 1987, 30, 20–24) was prepared as per the procedures illustrated in Example 56. 4-Methoxyaniline (4.93 g, 40.0 mmol), dry CH$_2$Cl$_2$ (200 mL), diisopropylethylamine (7.66 mL, 44.0 mmol), and bromoacetyl bromide (3.82 mL, 44.0 mmol) gave a beige solid (9.68 g) which was crystallized from ethyl acetate at reflux temperature to provide the title compound as white crystals (6.31 g, 65%).

Example 59

2-Bromo-N-(3-nitrophenyl)acetamide (Br-L$_2$) (compound 4)

The title compound (Johnson, H. W., Iwata, Y., *J. Org. Chem.*, 1971, 36, 1921–1925) was prepared as per the procedures illustrated in Example 56. 3-Nitroaniline (10.08 g, 73.0 mmol), dry CH$_2$Cl$_2$ (200 mL), diisopropylethylamine (14.0 mL, 80.3 mmol) and bromoacetyl bromide (7.0 mL, 80.3 mmol) gave a brown gum which was purified by flash chromatography using hexane:EtOAc (70:30, v/v) to give the title compound as a beige solid (12.84 g, 68%). $^1$H-NMR (Me$_2$SO-d$_6$): δ 10.9 (br s, 1H), 8.60 (m, 1H), 7.93 (m, 2H), 7.63 (m, 1H), 4.10 (s, 2H). $^{13}$C-NMR (CDCl$_3$): δ 163.6, 155.3, 130.6, 120.5, 113.0, 54.4, 28.9. Mass spectrum (FAB+) m/z 259/261 [M+H]+, 281/283 [M+Na]+.

Example 60

2-Bromo-N-(2-benzothiazolyl)acetamide (Br-L$_4$) (compound 5)

Compound 5 (Yuan, J., Zhang, M., *Beijing Daxue Xuebao, Ziran Kexueban*, 1988, 24, 504–506) was prepared as per the procedures illustrated in Example 56. 2-Aminobenzothiazole (7.50 g, 50.0 mmol), dry THF (250 mL), diisopropylethylamine (9.58 mL, 55.0 mmol), and bromoacetyl bromide (4.78 mL, 55.0 mmol) gave a purple solid which was crystallized from ethyl acetate at reflux temperature to provide the title compound as purple crystals (8.30 g, 61%). $^1$H-NMR (Me$_2$SO-d$_6$): δ 12.78 (br, 1H), 8.0–7.3 (m, 4H), 4.22 (s, 2H). Mass spectrum (FAB+) m/z 271/273 [M+H]+.

Example 61

2-Bromo-N-(1,2,3,4-tetrahydroisoquinoline) acetamide (Br-L$_{12}$) (compound 6)

The title compound was prepared as per the procedures illustrated in Example 56. 1,2,3,4-Tetrahydroisoquinoline hydrochloride (8.48 g, 50.0 mmol), dry CH$_2$Cl$_2$ (250 mL), diisopropylethylamine (19.2 mL, 110 mmol), and bromoacetyl bromide (4.78 mL, 55.0 mmol) gave a solid which was purified by flash chromatography using CH$_2$Cl$_2$:acetone (97:3, v/v) to afford the title compound as a yellow solid (9.38 g, 74%). $^1$H-NMR (CDCl$_3$): δ 7.17 (m, 4H), 4.72, 4.67 (s, s, 2H), 4.16, 4.14 (d, d, 2H), 3.75 (m, 2H), 2.80 (m, 2H). $^{13}$C-NMR (CDCl$_3$): δ 165.3, 134.4, 133.5, 132.4, 131.8, 128.6, 128.2, 126.5, 125.8, 48.0, 47.5, 44.5, 43.6, 41.2, 40.3, 29.1, 28.0, 26.3, 26.0. Mass spectrum (ES+) m/z 254/256 [M+H]+.

Example 62

2-Bromo-N-(3-5'-methylisoxazolyl)acetamide (Br-L$_1$) (compound 8)

The title compound was prepared as per the procedures illustrated in Example 56. 3-Amino-5-methylisoxazole (4.02 g, 41.0 mmol), dry THF (200 mL), diisopropylethylamine (7.85 mL, 45.1 mmol), and bromoacetyl bromide (3.91 mL, 41.1 mmol) gave a solid which was washed with CH$_2$Cl$_2$, then EtOAc to give the title compound as a white solid (5.17 g, 58%). $^1$H-NMR (Me$_2$SO-d$_6$): δ 11.32 (br s, 1H), 6.60 (s, 1H), 4.05 (s, 2H), 2.35 (s, 3H). $^{13}$C-NMR (CDCl$_3$): δ 170.0, 165.2, 158.0, 96.0, 29.3, 12.0. Mass spectrum (ES+) m/z 219/221 [M+H]+.

Example 63

N-(α-bromoacetyl)-4-methyl-2-amino-thiazole (Br-L$_{16}$) (compound 9)

The title compound (Kano, S., JP 45000326B4, 1970) was prepared as per the procedures illustrated in Example 56. 2-Amino-4-methylthiazole (11.42 g, 100 mmol), dry CH$_2$Cl$_2$ (200 mL), diisopropylethylamine (19.16 mL, 110 mmol), and bromoacetyl bromide (9.55 mL, 110 mmol) gave a solid which was washed with EtOAc, then methanol to afford the title compound as a beige solid (16.74 g, 71%). $^1$H-NMR (Me$_2$SO-d$_6$): δ 12.4 (br s, 1H), 6.80 (s, 1H), 4.12 (s, 2H), 2.24 (s, 3H). $^{13}$C-NMR (CDCl$_3$): δ 163.8, 157.2, 147.5, 109.0, 27.5, 17.0. Mass spectrum (ES+) m/z 235/237 [M+H]+.

Example 64

1-Phenyl-4-(2-N-(cycloheptyl)acetamido)piperazine (compound 18)

2-Bromo-N-(cycloheptyl)acetamide (Br-L$_1$) (234 mg, 1.0 mmol) was dissolved in dry THF (2.5 mL) and dry DMF (2.5 mL) followed by addition of 1-phenylpiperazine (0.153 mL, 1.0 mmol) and diisopropylethylamine (0.209 mL, 1.2 mmol) at ambient temperature. After stirring at ambient temperature for several hours, water (5 mL) was added and the reaction mixture was stirred for an additional 30 minutes. EtOAc (20 mL) was added and the organic layer was separated, washed twice with water then brine and dried with MgSO$_4$. The solvent was evaporated to afford the title compound as a solid (310 mg, 98%). $^1$H-NMR (acetone-d$_6$): δ 7.22–6.78 (m, 5H), 3.91 (m, 1H), 3.20 (t, 4H), 2.96 (s, 2H), 2.65 (t, 4H), 1.84–1.56 (m, 12H). $^{13}$C-NMR (acetone-d$_6$): δ 168.3, 152.2, 129.7, 120.0, 116.6, 62.4, 54.1, 50.2, 49.6, 35.5, 24.8. Mass spectrum (FAB+) m/z 316 [M+H]+, 338 [M+Na]+.

Example 65

1-Phenyl-4-(2-N-(furfuryl)acetamido)piperazine (compound 19)

The title compound was prepared as per the procedures illustrated in Example 64. 2-Bromo-N-(furfuryl)acetamide (Br-L$_5$) (0.24 mg, 1.10 mmol), 1-phenylpiperazine (0.15 mL, 1.0 mmol), and diisopropylethylamine (0.209 mL, 1.2 mmol) gave the title compound as a solid (284 mg, 95%). $^1$H-NMR (CDCl$_3$): δ 7.5 (br, 1H), 7.35–6.8 (m, 6H), 6.32 (m, 1H), 6.22 (m, 1H), 4.48 (d, 2H), 3.20 (t, 4H), 3.10 (s, 2H), 2.68 (t, 4H). $^{13}$C-NMR (CDCl$_3$): δ 170, 151.5, 150, 142, 129.5, 120, 116, 110.5, 107.5, 61.5, 53.5, 49, 36. Mass spectrum (ES+) m/z 300 (M +H]+.

Example 66

1-Phenyl-4-(2-N-(4-methoxyphenyl)acetamido) piperazine (compound 20)

The title compound was prepared as per the procedures illustrated in Example 64. 2-Bromo-N-(4-methoxyphenyl)

acetamide (Br-L₃) (244 mg, 1.00 mmol), 1-phenylpiperazine (0.153 mL, 1.00 mmol), and diisopropylethylamine (0.209 mL, 1.2 mmol) gave the title compound as a solid (319 mg, 98%). $^1$HNMR (acetone-d₆): δ 9.3 (br, 1H), 7.6–6.7 (m, 9H), 3.75 (s, 3H), 3.28 (t, 4H), 3.14 (s, 2H), 2.76 (t, 4H). $^{13}$C-NMR (acetone-d₆): δ 168.2, 156.8, 152.3, 132.7, 129.7, 121.6, 120.0, 116.6, 114.5, 62.7, 55.5, 54.1, 49.6. Mass spectrum (FAB+) m/z 326 [M+H]+458 [M+Cs]+.

Example 67

1-Phenyl-4-(2-N-(3-nitrophenyl)acetamido) piperazine (compound 21)

The title compound was prepared as per the procedures illustrated in Example 64. 2-Bromo-N-(3-nitrophenyl) acetamide (Br-L₂) (0.28 g, 1.10 mmol), 1-phenylpiperazine (0.15 mL, 1.0 mmol), and diisopropylethylamine (0.209 mL, 1.2 mmol) gave the title compound as a solid (0.33 g, 95%). $^1$H-NMR (CDCl₃): δ 9.4 (br, 1H), 8.4–6.7 (m, 9H), 3.30 (t, 4H), 3.25 (s, 2H), 2.80 (t, 4H). $^{13}$C-NMR (CDCl₃): δ 168.5, 149, 130, 129.5, 125, 121.5, 119, 116.5, 114, 62, 53.5, 49. Mass spectrum (ES+) m/z 341 [M+H]+.

Example 68

1-Phenyl-4-(2-N-(2-benzothiazolyl)acetamide) piperazine (compound 22)

The title compound was prepared as per the procedures illustrated in Example 64. 2-Bromo-N-(2-benzothiazolyl) acetamide (Br-L₄) (271 mg, 1.0 mmol), 1-phenylpiperazine (0.153 mL, 1.0 mmol), and diisopropylethylamine (0.209 mL, 1.2 mmol) gave the title compound as a solid (340 mg, 96%). $^1$H-NMR (Me₂SO-d₆): δ 12.0 (br, 1H), 8.0–6.75 (m, 9H), 3.41 (s, 2H), 3.15 (m, 4H), 2.68 (m, 4H). $^{13}$C-NMR (Me₂SO-d₆): δ 169.4, 157.5, 151.0, 148.5, 131.5, 128.9, 126.2, 123.6, 121.7, 120.6, 118.9, 115.5, 60.2, 52.5, 48.2. Mass spectrum (FAB+) m/z 353 [M+H]+, 375 [M+Na]+.

Example 69

1-Phenyl-4-(2-N-(1,2,3,4-tetrahydroisoquinoline) acetamide)-piperazine (compound 23)

The title compound was prepared as per the procedures illustrated in Example 64. 2-Bromo-N-(1,2,3,4-tetrahydroisoquinoline)acetamide (Br-L₁₂)(127 mg, 0.50 mmol), 1-phenylpiperazine (0.0764 mL, 0.50 mmol), and diisopropylethylamine (0.104 mL, 0.60 mmol) gave the title compound as a solid (160 mg, 95%). $^1$H-NMR (CD₃CN): δ 7.25–6.75 (m, 9H), 4.79 (br s, 0.66 H), 4.64 (br s, 1.34 H), 3.75 (m, 2H), 3.28 (s, 2H), 3.1 (m, 4H), 2.85 (m, 2H), 2.60 (m, 4H). Mass spectrum (FAB+) m/z 336 [M+H]+.

Example 70

1-Phenyl-4-(2-N-acetamide)piperazine (compound 24)

The title compound was prepared as per the procedures illustrated in Example 64. 2-Bromoacetamide (Br-L₁₇) (7.59 g, 55 mmol), 1-phenylpiperazine (7.64 mL, 50.0 mmol), and diisopropylethylamine (9.58 mL, 55.0 mmol) gave the title compound as a solid (6.7 g, 61%). The crude product was crystallized from acetone to give the title compound as white crystals (3.05 g). $^1$H-NMR (Me₂SO-d₆) δ 7.25–6.7 (m, 5H), 7.15 (br, 2H), 3.14 (t, 4H), 2.90 (s, 2H), 2.56 (t, 4H). $^{13}$C-NMR (CDCl₃): δ 173.2, 150.9, 129.0, 119.9, 116.0, 61.4, 53.4, 49.2.

Example 71

1-Phenyl-4-(2-N-(3-5'-methylisozazolyl)acetamide) piperazine (compound 25)

The title compound was prepared as per the procedures illustrated in Example 64. 2-Bromo-N-(3-5'-methylisoxazolyl)acetamide (Br-L₁₁) (0.24 g, 1.10 mmol), 1-phenylpiperazine (0.153 mL, 1.0 mmol), and diisopropylethylamine (0.19 mL, 1.1 mmol) gave the title compound as a solid (0.28 g, 95%). $^1$H-NMR (CD₃CN): δ 9.5 (br, 1H), 7.3–6.65 (m, 6H), 3.20 (t, 4H), 3.18 (s, 2H), 2.70 (t, 4H), 2.35 (s, 3H). $^{13}$C-NMR (CD₃CN): δ 171.5, 169.5, 158.5, 152.5, 130, 120, 116.5, 97, 62, 54, 49.5, 12.5. Mass spectrum (ES+) m/z 301 [M+H]+. (ES−) m/z 299 [M−H]−.

Example 72

1-Phenyl-4-(2-N-(2-4'-methylthiazolyl)acetamide) piperazine (compound 26)

The title compound was prepared as per the procedures illustrated in Example 64. N-(α-bromoacetyl)-4-methyl-2-amino-thiazole (Br-L₁₆) (0.26 g, 1.1 mmol), 1-phenylpiperazine (0.153 mL, 1.0 mmol), and diisopropylethylamine (0.19 mL, 1.1 mmol) gave the title compound as a solid (0.29 g, 95%). $^1$H-NMR (CD₃CN): δ 7.25–6.6 (m, 6H), 3.25 (s, 2H), 3.20 (t, 4H), 3.1 (br, 1H), 2.68 (t, 4H), 2.25 (s, 3H). $^{13}$C-NMR (CD₃CN) δ 130, 121, 117, 109, 61.5, 54, 50, 17. Mass spectrum (ES+) m/z 317 [M+H]+. (ES−) m/z 315 [M−H].

Example 73

1-Phenyl-4-(1-2-butanonyl)piperazine (compound 27)

The title compound was prepared as per the procedures illustrated in Example 64. 1-Bromo-2-butanone (Br-L₁₈) (0.124 mL, 1.1 mmol), 1-phenylpiperazine (0.153 mL, 1.0 mmol), and diisopropylethylamine (0.209 mL, 1.2 mmol) gave the title compound as an oil (234 mg, 95%). $^1$H-NMR (pyr-d₅): δ 7.35–6.85 (m, 5H), 3.20 (t, 4H), 3.18 (s, 2H), 3.26 (t, 4H), 2.44 (q, 2H), 1.02 (t, 3H).

Example 74

1-Phenyl-4-(6-acetyl-1,2,3,4-tetrahydro-1,1,4,4-tetramethyl-naphthalene-acetamido)piperazine (compound 28)

The title compound was prepared as per the procedures illustrated in Example 64. 6-(Bromoacetyl)-1,2,3,4-tetrahydro-1,1,4,4-tetramethylnaphthalene (Br-L₁₉) (309 mg, 1.0 mmol), 1-phenylpiperazine (0.153 mL, 1.0 mmol), and diisopropylethylamine (0.209 mL, 1.2 mmol) gave the title compound as an oil (390 mg, 95%). $^1$H-NMR (pyridine-d₅): δ 8.35–6.9 (m, 8H), 3.94 (s, 2H), 3.20 (t, 4H), 2.80 (t, 4H), 1.59 (s, 4H), 1.24 (d, 12H). Mass spectrum (ES+) m/z 391 [M+H]+.

Example 75

1-Phenyl-4-(6-acetyl-2-ozo-1,2,3,4-tetrahydroquinoline)piperazine (compound 29)

The title compound was prepared as per the procedures illustrated in Example 64. 6-(Bromoacetyl)-2-oxo-1,2,3,4-tetrahydroquinoline (Br-L₂₀) (268 mg, 1.0 mmol), 1-phenylpiperazine (0.153 mL, 1.0 mmol), and diisopropylethylamine (0.209 mL, 1.2 mmol) gave the title compound as a solid (295 mg, 84%). $^1$H-NMR (pyridine-d$_5$): δ 8.1–6.9 (m, 8H), 3.90 (s, 2H), 3.24 (m, 4H), 2.9–2.65 (m, 4H), 2.82 (m, 4H). Mass spectrum (ES+) m/z 350 [M+H]+.

Example 76

1-Phenyl-4-(2-acetyl-5-chloro-3-methylbenzo[b] thiophene)-piperazine (compound 30)

The title compound was prepared as per the procedures illustrated in Example 64. 2-(Bromoacetyl)-5-chloro-3-methylbenzo[b]thiophene(Br-L$_{21}$) (334 mg, 1.1 mmol), 1-phenylpiperazine (0.153 mL, 1.0 mmol), and diisopropylethylamine (0.209 mL, 1.2 mmol) gave the title compound as a solid (410 mg, 95%). $^1$H-NMR (pyr-d$_5$): δ 8.00–6.9 (m, 8H), 3.69 (s, 2H), 3.26 (t, 4H), 2.73 (t, 4H), 2.74 (s, 3H).

Example 77

1-Phenyl-4-(5-methylbenzofurazan)piperazine (compound 31)

The title compound was prepared as per the procedures illustrated in Example 64. 5-(Bromomethyl)benzofurazan (104 mg, 0.488 mmol) (Br-L$_{22}$), 1-phenylpiperazine (0.75 mL, 0.488 mmol), and diisopropylethylamine (0.093 mL, 0.536 mmol) gave the title compound as a solid (139 mg, 96%). $^1$H-NMR (CDCl$_3$): δ 7.8–6.8 (m, 8H), 3.65 (s, 2H), 3.23 (t, 4H), 2.67 (t, 4H). Mass spectrum (ES+) m/z 296 [M+H]+.

Example 78

1-Phenyl-4-(3-methyl-5-chlorobenzo[b]thiophene) piperazine (compound 32)

The title compound was prepared as per the procedures illustrated in Example 64. 3-(bromomethyl)-5-chlorobenzo[b]thiophene (Br-L$_{23}$) (99.9 mg, 0.461 mmol), 1-phenylpiperazine (0.070 mL, 0.461 mmol), and diisopropylethylamine (0.087 mL, 0.507 mmol) gave the title compound as a solid (150 mg, 95%). $^1$H-NMR (CDCl$_3$): δ 8.0–6.8 (m, 9H), 3.76 (s, 2H), 3.20 (t, 4H), 2.65 (t, 4H).

Example 79

1-Phenyl-4-(6-methyl-4-chloro-2-trifluoromethyl-quinoline)-piperazine (compound 33)

The title compound was prepared as per the procedures illustrated in Example 64. 6-(Bromomethyl)-4-chloro-2-trifluoromethyl)quinoline (Br-L$_{24}$) (106 mg, 0.326 mmol), 1-phenylpiperazine (0.050 mL, 0.326 mmol), and diisopropylethylamine (0.061 mL, 0.359 mmol) gave the title compound as a solid (122 mg, 92%). $^1$H-NMR (CDCl$_3$): δ 8.25–6.85 (m, 9H), 3.80 (s, 2H), 3.23 (t, 4H), 2.70 (t, 4H).

Example 80

1-Phenyl-4-(4-(4-methylphenyl)-1,2,3-thiadiazole) piperazine (compound 34)

The title compound was prepared as per the procedures illustrated in Example 64. 4-(4-Bromomethylphenyl)-1,2,3-thiadiazole (Br-L$_{25}$) (101 mg, 0.396 mmol), 1-phenylpiperazine (0.60 mL, 0.396 mmol), and diisopropylethylamine (0.076 mL, 0.436 mmol) gave the title compound as a solid (133 mg, 95%). $^1$H-NMR (CDCl$_3$): δ 8.65–6.9 (m, 10H), 3.65 (s, 2H), 3.23 (t, 4H), 2.65 (t, 4H). Mass spectrum (ES+) m/z 337 [M+H]+.

In addition the letter sets may be expanded by inclusion of other commercially available classes of reactive compounds, e.g., b enzyl, benzyl-like heteraromatic-bromides, or α-bromoketones.

Example 81

Calibration Curves for Set 1, L$_1$–L$_5$ (FIG. 1), Preparation of Libraries 40–44

Calibration curves were generated to enable the determination of the concentration of a compound within a library. Varying concentrations of L$_1$–L$_5$ (examples 56–60) were reacted with 1-phenyl-piperazine to prepare 5 libraries (libraries 40–44) with unique concentrations of products. In each library the concentration of products is determined by the amounts of starting materials used. Each library was analyzed by CZE and the data was correlated with the CZE's of the pure compounds. Each of the 5 compounds that are in each library were prepared pure in examples 64–68. The pure compounds were used to assign the peaks in the electropherogram. The 5 libraries were prepared as per Table 1 below.

TABLE 1

| Concentration array for calibration curves, (mmol) | | | | | |
|---|---|---|---|---|---|
| Compound | Lib 40 | Lib 41 | Lib 42 | Lib 43 | Lib 44 |
| 1 | 0.033 | 0.167 | 0.133 | 0.100 | 0.067 |
| 2 | 0.067 | 0.033 | 0.167 | 0.133 | 0.100 |
| 3 | 0.100 | 0.067 | 0.033 | 0.167 | 0.133 |
| 4 | 0.133 | 0.100 | 0.067 | 0.033 | 0.167 |
| 5 | 0.167 | 0.133 | 0.100 | 0.067 | 0.033 |
| total | 0.500 | 0.500 | 0.500 | 0.500 | 0.500 |
| 1-phenyl-piperazine | 0.500 | 0.500 | 0.500 | 0.500 | 0.500 |

0.500 M Stock solutions of L$_1$–L$_5$ were prepared by dissolving each compound (0.001 moles) in a 2.00 mL volumetric flask using dry DMF. The variance of concentrations of L$_1$–L$_5$ in each library resulted in a unique concentration for each product in each library. For example in Library 40, the amounts used were 67 μL, 0.033 mmol; 133 λL, 0.067 mmol; 200 μL, 0.100 mmol; 267 μL, 0.133 mmol; and 333 μL, 0.167 mmol of compounds 1–5, respectively. Each library was prepared in a glass scintillation vial containing dry THF (1.35 mL) and the indicated concentrations of L$_1$–L$_5$. 1-Phenylpiperazine (250 μL, 0.500 mmol) was added dropwise from a 2.00 M stock solution in DMF to the well-stirred reaction mixture followed by addition of neat N,N-diisopropylethylamine (105 μL, 0.600 mmol). 1-Phenyl-4-(2-acetamido)piperazine (24) (100 μL, 0.100 mmol) was added to Library 40, from a 1.00 M stock solution in DMF, as an internal standard (subsequently (+–)-dropropizine was used for libraries 2–5). After stirring the sealed reaction mixtures for 1 hour at ambient temperature, an aliquot (5.6 μL) was taken and diluted to a volume of 10 mL with 0.5% AcOH in MeOH to give 100 μM CZE samples. The CZE analysis of each library generated 5 points, one point per compound. The 5 libraries collectively produced a total of 25 points, 5 points per compound.

Analyses of the resulting data using Microsoft Excel software provided absorbance vs. concentration calibration curves for each of the products. The application of Beer's law to the resulting data yielded the data necessary for determination of the identity and concentration of each the compounds in a mixture.

Example 82

Method for Obtaining Uniform Rates and k$_{app}$, Preparation of Library 45

As per the procedure illustrated in Example 81, and using compounds Br-L$_4$ and Br-L$_{22}$ thru Br-L$_{25}$ as alkylating agents, a calibration curve was generated for compounds 22 and 31–34. A pseudo-competitive reaction was then performed in which 0.5 equivalent of compounds Br-$L_4$ and Br-$L_{22}$ thru Br-$L_{25}$ (2.5 eq. total) was reacted with 0.5 equivalent of the nucleophile, 1-phenylpiperazine, to form products 22 and 31–34 (Table 2, exp 1).

The next step was the determination of relative reactivities under competitive conditions for compounds Br-$L_4$ and Br-$L_{22}$ thru Br-$L_{25}$. (Ragnarsson, U., et al., *J. Org. Chem.*, 1974, 39, 3837–3841). Compounds Br-$L_4$ (0.500 mmol), Br-$L_{22}$ (0.500 mmol), Br-$L_{23}$ (0.500 mmol), Br-$L_{24}$ (0.500 mmol) and Br-$L_{25}$ (0.500 mmol) were dissolved in dry DMF (6.25 mL) and dry THF (6.25 mL) in a scintillation vial. 1-Phenylpiperazine (250 μL, 0.500 mmol) from a 2.00 M stock solution in DMF was added dropwise to the well-stirred reaction mixture followed by addition of neat N,N-diisopropylethylamine (105 μL, 0.600 mmol). Dropropizine (internal standard) (0.100 mmol) from a 1.00 M stock solution in DMF was added and the mixture was sealed and stirred for 1 hour at ambient temperature. An aliquot (26 μL) of the reaction mixture was removed and diluted to a volume of 10 mL with 0.5% AcOH in MeOH to give a 100 μM sample.

The sample was analyzed by CZE and the concentration of each product was determined by converting the absorbance to a concentration using the calibration curves previously generated above (equation takes form of y=mx+b, where y=absorbance, m=extinction coefficient (ε), x=concentrtion, and b=intercept). It is noted that although there are excess alkylating agents present within the reaction mixture, they are transparent to the CZE method as they are not charged under the given conditions (pH 3) and migrate with the electroosmotic flow.

To a first approximation the gross relative rates of product formation are estimated to be proportional to the relative concentrations of products at equilibrium, with 22 serving as a standard (Ragnarsson, ibid). Compound 22 was used as a standard because it consistently had a faster relative rate in the reaction schemes examined. The rank order of rates for product formation was determined as 22>33>31>32>34. The relative rate was estimated as the ratio of the equilibrium concentration of each compound to the equilibrium concentration of compound 22 (e.g. relative rate of 34 is=0.355 (Table 2, exp. 1). For further refinement a weighting factor (wt. factor) was calculated as being inversely proportional to the relative rate , i.e., 1/rel rate (Ostresh, J. M., et al., *Biopolymers*, 1994, 34, 1681–1689).

To determine the adjusted concentration of each alkylating agent for Run 2 (Table 2) of the normalization process, the concentration of compound 22 was arbitrarily set to be equal to 0.110 mmol (or 0.22 eq.). This amount is based on providing a total of 10 mole % excess of 5 alkylating agents and 0.500 mmol of 1-phenylpiperazine. The concentrations of compounds Br-$L_{22}$ thru Br-$L_{25}$ (14–17) were calculated as their wt. factor from exp. 1, times the amount of RBr, exp 1., normalized to standard, ie., wt. factor times 0.110 mmol. In Table 2, Run 2 these new calculated concentrations were used and the procedures used in run 1 above were repeated. Run 2 (Table 2) generates a second round of wt. factors which are applied to the amounts of alkylating agents used in exp. 3, in a third round of synthesis (Run 3, Table 2).

TABLE 2

| compd | R—Br (mmol) | rel conc (M) | rel rate | wt factor |
|---|---|---|---|---|
| Run 1 | | | | |
| 34 | 0.500 | 0.071 | 0.355 | 2.820 |
| 32 | 0.500 | 0.074 | 0.374 | 2.675 |
| 33 | 0.500 | 0.085 | 0.427 | 2.341 |
| 31 | 0.500 | 0.082 | 0.411 | 2.434 |
| 22 | 0.500 | 0.199 | 1.000 | 1.000 |
| total R—Br | 2.500 | | | |
| 1-phenyl-piperazine | 0.500 | | | |
| RUN 2 | | | | |
| 34 | 0.310 | 0.0765 | 1.229 | 0.813 |
| 32 | 0.294 | 0.0766 | 1.230 | 0.813 |
| 33 | 0.257 | 0.0757 | 1.217 | 0.822 |
| 31 | 0.268 | 0.0844 | 1.357 | 0.737 |
| 22 | 0.110 | 0.0622 | 1.000 | 1.000 |
| total R—Br | 1.240 | | | |
| 1-phenyl-piperazine | 0.500 | | | |

| | RUN 3 | | | |
|---|---|---|---|---|
| compd | R—Br (mmol) | rel conc (M) | rel rate | wt factor |
| 34 | 0.252 | 0.0922 | 1.03 | 0.974 |
| 32 | 0.239 | 0.0930 | 1.04 | 0.965 |
| 33 | 0.212 | 0.0937 | 1.04 | 0.958 |
| 31 | 0.197 | 0.0930 | 1.04 | 0.966 |
| 22 | 0.110 | 0.0898 | 1.00 | 1.000 |
| total R—Br | 1.010 | | | |
| 1-phenyl-piperazine | 0.500 | | | |

| | RUN 4 PROJECTED | |
|---|---|---|
| compd | wtd R—Br (mmol) | kapp |
| 34 | 0.302 | 0.364 |
| 32 | 0.284 | 0.387 |
| 33 | 0.247 | 0.446 |
| 31 | 0.259 | 0.425 |
| 22 | 0.110 | 1.000 |
| total R—Br | 1.201 | |
| 1-phenyl-piperazine | 0.500 | |

Compound 34, in exp. 2, e.g., generated a wt. factor of 0.813, which was applied to the RBr amount (0.310 mmol) of exp. 2 to provide the exp. 3 RBr amount (0.252 mmol= 0.813×0.310 mmol).Typically, by the third competitive experiment the relative rates of reaction for the 5 products lay within a range of <15% of the reference (compound 22). Final refinements of the weighted concentrations were calculated, without performing the experiment, and to a first approximation apparent relative rate constants ($k_{app}$) were derived by normalizing to compound 22 and by assuming the $k_{app}$'s are inversely proportional to concentrations at which uniform relative rates are obtained. The $k_{app}$ values were determined for each of compounds $L_{1-5}$, $L_{11-12}$ and $L_{16-25}$ using the procedures illustrated above (FIGS. 1–4).

To illustrate, for compound 34 (Table 2, exp. 4), the rates can be represented (March, J., *adv. Organic Chem.*,

*Reactions, Mechanisms, and Structure*, 4th ed., 1992, J. Wiley and Sons) as:

$$d[34]/dt = k_{app\ 34}[\text{Ph-piperazine}][RBr_{34}] \quad (1)$$

$$d[22]/dt = k_{app\ 22}[\text{Ph-piperazine}][RBr_{22}] \quad (2)$$

since the relative rates are uniform:

$$d[34]/dt = d[22]/dt \quad (3)$$

after rearrangement:

$$k_{app\ 34}/k_{app\ 22} = [RBr_{22}]/[RBr_{34}] \quad (4)$$

or $$k_{app\ 34} = [RBr_{22}]/[RBr_{34}] \quad (5)$$

where $k_{app\ 22} = 1.00$ thus $$k_{app\ 34} = 0.110/0.302 = 0.364$$

If the letters are segregated by reactivities as electrophiles, i.e., slow, moderate, and fast, certain trends become apparent. In regard to the bromoacetamides, the slow reactors are comprised of those compounds in which the nitrogen is bonded to an aliphatic or benzylic-like carbon or to hydrogen. The moderately reactive bromoacetamides contain a nitrogen bonded to phenyl ring containing a strongly electron-releasing group, while the fast-reacting bromoacetamides include a nitrogen bonded to a heteroaromatic ring or to a phenyl ring containing a strongly electron-withdrawing group. Based on these results the reactivities of most bromoacetamides can be predicted to be slow, moderate, or fast reactors according to the previous criteria. Many bromoacetamides are available either commercially or are convenient synthetically in one step from selected amines. See Ser. No. 08/691,139, filed Aug. 1, 1996, incorporated herein by reference and assigned to the assignee of this invention. The ability to predict their reactivities provides a valuable tool in competitive reactions. In practice, any selected bromoacetamide may be assigned an approximate $k_{app}$ value according to the discussed criteria. The $k_{app}$ may then be used to estimate the proper concentration to achieve uniform reaction rates. In addition the letter sets may be expanded by inclusion of other commercially avialable classes of reactive compounds, e.g., benzyl, benzyl-like heteroaromatic-bromides, or α-bromoketones.

Example 83

Method for Obtaining Uniform Rates and $k_{app}$, Preparation of Library 46

I. Determination of relative reactivities for compounds Br-L$_1$ (117 mg, 0.500 mmol), Br-L$_2$ (109 mg, 0.500 mmol), Br-L$_3$ (122 mg, 0.500 mmol), Br-L$_4$ (130 mg, 0.500 mmol) and Br-L$_5$ (136 mg, 0.500 mmol) were dissolved in dry DMF (6.25 mL) and dry THF (6.25 mL) in a scintillation vial. 1-Phenylpiperazine (250 µL, 0.500 mmol) from a 2.00 M stock solution in DMF was added dropwise to the well-stirred reaction mixture followed by addition of neat N,N-diisopropylethylamine (105 µL, 0.600 mmol). 1-Phenyl-4-(2-acetamide)piperazine 24 (internal standard) (100 µL, 0.100 mmol) from a 1.00 M stock solution in DMF was added and the mixture was sealed and stirred for 1 hour at ambient temperature. An aliquot (26 µL) of the reaction mixture was removed and diluted to a volume of 10 mL with 0.5% AcOH in MeOH to give a 100 µM sample that was analyzed by CZE. Using the calibration curves obtained in Example 81 the concentration of each compound was determined. This information was used to assign relative reactivities to each of compounds 1–5.

II. Refinement of relative rates for compounds 1–5. From the results of step 1, adjusted concentrations of compounds Br-L$_{1-5}$ were used to approximate uniform rates in reaction with 1-phenylpiperazine. Compounds Br-L$_1$ (68.4 mg, 0.292 mmol), Br-L$_2$ (63.7 mg, 0.292 mmol), Br-L$_3$ (43.4 mg, 0.178 mmol), Br-L$_4$ (46.1 mg, 0.178 mmol), Br-L$_5$ (29.8 mg, 0.110 mmol) were dissolved in dry DMF (2.50 mL) and dry THF (2.50 mL) in a scintillation vial. 1-Phenylpiperazine (250 µL, 0.500 mmol) from a 2.00 M stock solution in DMF was added dropwise to the well-stirred reaction mixture followed by addition of neat N,N-diisopropylethylamine (105 µL, 0.600 mmol) and 1-phenyl-4-(2-acetamide)piperazine 24 (internal standard) (100 µL, 0.100 mmol) from a 1.00 M stock solution in DMF. After stirring the sealed reaction mixture for 1 hour at ambient temperature, an aliquot (10 µL) of the reaction mixture was diluted to a volume of 10 mL with 0.5% AcOH in MeOH to give a 100 µM sample that was analyzed by CZE. Using the calibration curves obtained in Example 81 the concentration of each compound was determined. This information was used to assign relative reactivities to each of compounds Br-L$_{1-5}$.

III. Final refinement of relative rates for compounds Br-L$_{1-5}$. From the results of step II, a further adjustment of concentrations of compounds Br-L$_{1-5}$ were used to approximate uniform rates in reaction with 1-phenylpiperazine. Compounds Br-L$_1$ (76.7 mg, 0.327 mmol), Br-L$_2$ (66.4 mg, 0.304 mmol), Br-L$_3$ (44.6 mg, 0.183 mmol), Br-L$_4$ (32.2 mg, 0.124 mmol), Br-L$_5$ (29.8 mg, 0.110 mmol) were dissolved in dry DMF (2.37 mL) and dry THF (2.62 mL) in a scintillation vial. 1-Phenylpiperazine (250 µL, 0.500 mmol) from a 2.00 M stock solution in DMF was added dropwise to the well-stirred reaction mixture followed by addition of neat N,N-diisopropylethylamine (105 µL, 0.600 mmol) and 1-phenyl-4-(2-acetamide)piperazine 24 (internal standard) (100 µL, 0.100 mmol) from a 1.00 M stock solution in DMF. After stirring the sealed reaction mixture for 1 hour at ambient temperature, an aliquot (10.5 µL) of the reaction mixture was diluted to a volume of 10 mL with 0.5% AcOH in MeOH to give a 100 µM sample for CZE analysis. Using the calibration curves obtained in Example 81 the concentration of each compound was determined. This information was used to assign relative reactivities to each of compounds Br-L$_{1-5}$.

Example 84

Equimolar Mixture of Compounds 18–22 (Set 1), Preparation of Library 47

Following the procedures illustrated in example 83, an adjusted mixture of compounds Br-L$_{1-5}$ was prepared representing a further refinement of data based on the relative rates for compounds Br-L$_{1-5}$. This mixture was reacted with 1-phenylpiperazine as per the procedures of Example 83. Freshly prepared 2-mercaptoethanesulfonic acid, sodium salt (271 mg, 1.65 mmol) and K$_2$CO$_3$ (228 mg, 1.65 mmol) dissolved in water (3.2 mL) were added to the reaction mixture and the mixture was stirred at ambient temperature for 30 minutes after which time EtOAc (25 mL) was added. After agitating the biphasic mixture, the organic layer was separated, washed with water (2×5 mL), brine (1×3 mL), and dried with MgSO$_4$. The solvent was evaporated in vacuo to give an oil which was coevaporated with toluene and dried in vacuo for 12 hours to provide compounds 18–22 and 24 (internal standard) as a residue (193 mg). Mass spectrum (ES+) m/z 220.5 [M+H]+, 299.9 [M+H]+, 315.8 [M+H]+, 325.7 [M+H]+, 340.5 [M+H]+, 352.5 [M+H]+.

Example 85

Equimolar Mixture of Compounds 22–26 (Set 2), Preparation of Library 48

The competitive reactions led to final weighted concentrations of Br-$L_4$, Br-$L_{11}$, Br-$L_{12}$, Br-$L_{16}$ and Br-$L_{17}$. Compounds Br-$L_{12}$ (80.4, 0.316 mmol), Br-$L_{17}$ (75.1 mg, 0.545 mmol), Br-$L_{11}$ (32.9 mg, 0.150 mmol), Br-$L_{16}$ (29.8 mg, 0.127 mmol), and Br-$L_4$ (29.8 mg, 0.110 mmol) were dissolved in dry DMF (3.12 mL) and dry THF (3.12 mL) in a scintillation vial. A 2.00 M stock solution in DMF of 1-phenylpiperazine (250 μL, 0.500 mmol) was added dropwise to the well-stirred reaction mixture followed by addition of neat N,N-diisopropylethylamine (105 μL, 0.600 mmol). The internal standard was inadvertently omitted in this case. After stirring the sealed reaction mixture for 1 hour at ambient temperature, an aliquot (13.4 μL) of the reaction mixture was diluted to a volume of 10 mL with 0.5% AcOH in MeOH to give a 100 μM CZE sample. CZE was performed to provide relative rates for compounds 5–9. Freshly prepared 2-mercaptoethanesulfonic acid, sodium salt (369 mg, 2.25 mmol) and $K_2CO_3$ (311 mg, 2.25 mmol) dissolved in water (5 mL) were added to the reaction mixture and the mixture was stirred at ambient temperature for 30 minutes after which time EtOAc (25 mL) was added to the reaction mixture. After agitating the biphasic mixture, the organic layer was separated, washed with water (2×5 mL), brine (1×3 mL), and dried with $MgSO_4$. The solvent was evaporated in vacuo to give an oil which was coevaporated with toluene and dried in vacuo for 12 hours to provide compounds 22–26 as a residue (168 mg). Mass spectrum (ES+) m/z 221.6 [M+1]+, 302.1 [M+1]+, 317.9 [M+1]+, 336.9 [M+1]+, 353.7 [M+1]+.

Example 86

Equimolar Mixture of Compounds 22 and 31–34 (Set 4), Preparation of Library 49

The competitive reactions led to final weighted concentrations of Br-$L_4$ and Br-$L_{22-25}$. Compounds Br-$L_{22}$ (42.0 mg, 0.197 mmol), Br-$L_{23}$ (62.6 mg, 0.239 mmol), Br-$L_{24}$ (68.7 mg, 0.212 mmol), Br-$L_{25}$ (64.4 mg, 0.252 mmol), Br-$L_4$ (29.8 mg, 0.110 mmol) were dissolved in dry DMF (2.53 mL) and dry THF (2.53 mL) in a scintillation vial. A 2.00 M stock solution in DMF of 1-phenylpiperazine (250 μL, 0.500 mmol) was added dropwise to the well-stirred reaction mixture followed by addition of neat N,N-diisopropylethylamine (105 μL, 0.600 mmol) and a 1.00 M stock solution in DMF of (+−)-dropropizine (internal standard) (100 μL, 0.100 mmol). After stirring the sealed reaction mixture for 1 hour at ambient temperature, an aliquot (11 μL) of the reaction mixture was diluted to a volume of 10 mL with 0.5% AcOH in MeOH to give a 100 μM CZE sample. Freshly prepared 2-mercaptoethanesulfonic acid, sodium salt (251 mg, 1.53 mmol) and $K_2CO_3$ (212 mg, 1.53 mmol) dissolved in water (3 mL) were added to the reaction mixture and the mixture was stirred at ambient temperature for 30 minutes after which time EtOAc (25 mL) was added to the reaction mixture. After agitating the biphasic mixture, the organic layer was separated, washed with water (2×5 mL), brine (1×3 mL), and dried with $MgSO_4$. The solvent was evaporated in vacuo to give an oil which was coevaporated with toluene and dried in vacuo for 12 hours to provide compounds 22, 31–34, and dropropizine as a residue (190 mg). Mass spectrum (ES+) m/z 237.3 [M+1]+, 294.9 [M+1]+, 336.6 [M+1]+, 342.5 [M+1]+, 352.5 [M+1]+, 405.0 [M+1]+.

Example 87

Equimolar Mixture of Set 5, Compounds 22, 25 and 27–29, Preparation of Library 50

The competitive reactions led to final weighted concentrations of Br-$L_4$, Br-$L_{11}$, Br-$L_2$, Br-$L_{18}$, Br-$L_{19}$ and Br-$L_{20}$. Compounds Br-$L_{18}$ (13.9 μL, 0.136 mmol), Br-$L_{19}$ (38.4 mg, 0.124 mmol), Br-$L_{20}$ (32.6 mg, 0.121 mmol), Br-$L_{11}$ (44.4 mg, 0.203 mmol) Br-$L_4$ (40.6 mg, 0.150 mmol) were dissolved in dry DMF (1.84 mL) and dry THF (1.84 mL) in a scintillation vial. A 2.00 M stock solution in DMF of 1-phenylpiperazine (250 μL, 0.500 mmol) was added dropwise to the well-stirred reaction mixture followed by addition of neat N,N-diisopropylethylamine (105 μL, 0.600 mmol) and a 1.00 M stock solution in DMF of (+−)-dropropizine (internal standard) (100 μL, 0.100 mmol). After stirring the sealed reaction mixture for 1 hour at ambient temperature, an aliquot (8.3 μL) of the reaction mixture was diluted to a volume of 10 mL with 0.5% AcOH in MeOH to give a 100 μM CZE sample. CZE was performed to provide relative rates for compounds Br-$L_4$, Br-$L_{11}$, Br-$L_2$, Br-$L_{18}$, Br-$L_{19}$ and Br-$L_{20}$. Freshly prepared 2-mercaptoethanesulfonic acid, sodium salt (115 mg, 0.70 mmol) and $K_2CO_3$ (97 mg, 0.70 mmol) dissolved in water (3 mL) were added to the reaction mixture and the mixture was stirred at ambient temperature for 30 minutes after which time EtOAc (25 mL) was added to the reaction mixture. After agitating the biphasic mixture, the organic layer was separated, washed with water (2×5 mL), brine (1×3 mL), and dried with $MgSO_4$. The solvent was evaporated in vacuo to give an oil which was coevaporated with toluene and dried in vacuo for 12 hours to provide compounds 22, 25, 27–29 and dropropizine as a residue (186 mg). Mass spectrum (ES+) m/z 234.6 [M+1]+, 238.5 [M+1]+, 302.1 [M+1]+, 350.7 [M+1]+, 353.7 [M+1]+, 391.6 [M+1]+.

Example 88

Correlation Coefficients ($r^2$), Extinction Coefficients ($\epsilon$), and Intercepts of Calibration Curves Following the procedures illustrated in examples 81–87 the correlation coefficients ($r^2$), extinction coefficients ($\epsilon$), and intercepts were calculated for the compounds listed in Table 3 below.

TABLE 3

| | compound | $r^2$ | $\epsilon$ | intercept |
|---|---|---|---|---|
| set 1 | 18 | 0.996 | 12.9 | −0.03 |
| | 20 | 0.999 | 21.9 | 0.02 |
| | 19 | 0.989 | 25.6 | 0.08 |
| | 21 | 0.999 | 25.0 | −0.05 |
| | 22 | 0.997 | 61.0 | −0.05 |
| set 2 | 23 | 0.999 | 22.4 | 0.11 |
| | 24 | 0.997 | 15.2 | 0.00 |
| | 25 | 1.000 | 83.4 | 0.09 |
| | 26 | 0.999 | 36.4 | −0.05 |
| | 22 | 1.000 | 127.3 | −0.10 |
| set 3 | 27 | 0.997 | 11.9 | −0.16 |
| | 28 | 0.993 | 32.6 | 0.00 |

TABLE 3-continued

| | compound | $r^2$ | $\epsilon$ | intercept |
|---|---|---|---|---|
| | 29 | 0.998 | 34.8 | 0.15 |
| | 30 | 0.918 | 31.0 | −0.55 |
| | 22 | 0.998 | 131.7 | −0.77 |
| set 4 | 34 | 0.999 | 42.6 | −0.02 |
| | 32 | 0.999 | 75.1 | −0.14 |
| | 33 | 0.998 | 165.6 | −0.20 |
| | 31 | 1.000 | 35.2 | −0.03 |
| | 22 | 0.998 | 117.1 | −0.09 | set 1 internal standard = 24, sets 2–4 internal standard = (+−)-dropropizine.

Example 89

2,6,8-Tris(mercapto)-9H-purine

The title compound was prepared by adapting the procedures of Noell, C. W., Robins, R. K., *J. Am. Chem. Soc.*, 1959, 81, 5997–6007. 2,8-Bis(mercapto)-6-hydroxypurine (10.0 g, 49.9 mmol) and phosphorous pentasulfide (19.96 g, 44.9 mmol) were mixed as solids, then suspended in anhydrous pyridine (180 mL). This mixture was heated at reflux temperature for 9 hours giving a dark solution. After cooling the reaction mixture to ambient temperature degassed water (180 mL) was slowly added. The solution was stirred for 12 hours and concentrated. The resulting residue was dissolved in 1N NH$_4$OH and heated to reflux temperature for 10 minutes. The dark mixture was filtered and the hot filtrate was acidified to pH 3 with aqueous 4N HCl to give a yellow precipitate which was filtered and washed with water 3 times. The crude material was purified by dissolution in aqueous 1N NH$_4$OH followed by precipitation by acidification to pH 3 with 4N HCl to give a yellow precipitate. The precipitate was washed with water and triturated with acetone to afford the title compound as a yellow solid (5.60 g, 52%).

Example 90

Preparation of Library 51

2,6,8-Tris(mercapto)-9H-purine (216.3 mg, 1.00 mmol) was suspended in DMF (2 mL), 2.0 N aqueous NaOH (1.8 mL, 3.6 mmol) was added to give a first solution. N-(α-Bromo-acetyl)-3-amino-5-methylisoxazole (219 mg, 1.00 mmol, Br-L$_{11}$), N-(α-bromoacetyl)-4-methyl-2-aminothiazole (235 mg, 1.00 mmol, Br-L$_{26}$), and N-(α-bromoacetyl)-2-aminobenzothiazole (271.1 mg, 1.00 mmol, Br-L$_4$) were dissolved in DMF (3 mL) to give a second solution. The second solution was added slowly to the first solution at ambient temperature. After 2 hours glacial AcOH (2 mL) was added followed by addition of water (5 mL) to give a precipitate. The precipitate was filtered, washed with water 3 times and dried in vacuo to afford the title compound as a tan solid.

Example 91

Preparation of Library 52

2,6,8-Tris(mercapto)-9H-purine (216.3 mg, 1.00 mmol) was suspended in DMF (2 mL), and 2.0 N aqueous NaOH (1.8 mL, 3.6 mmol) was added to give a first solution. α-Bromo-m-xylene (0.135 mL, 1.00 mmol, Br-L$_{27}$), m-triflouro-methylbenzylbromide (0.153 mL, 1.00 mmol, Br-L$_{10}$), and m-nitrobenzylbromide (271.1 mg, 1.00 mmol, Br-L$_8$) were dissolved in DMF (3 mL) and this solution was added dropwise to the first solution at ambient temperature. After 2 hours a solution of 2-mercaptoethanesulfonic acid, sodium salt (82 mg, 0.500 mmol) and K$_2$CO$_3$ (69 mg, 0.50 mmol) dissolved in water was added to the reaction mixture. After stirring for 5 minutes the pH was adjusted to 5–6 with glacial AcOH. Water (2 mL) was added followed by addition of EtOAc (50 mL) and the mixture was stirred. The organic layer was separated, washed with water (3×5 mL), brine and dried (MgSO$_4$). The solvent was evaporated in vacuo to give Library 52 as an oil (724 mg). MS(ES−) m/z: 558, 581, 589, 612, 620, 635, 643, 666, 689.

Example 92

Preparation of Library 53

The title library was prepared as per the procedures of Example 90 using 2,6,8-tris(mercapto)-9H-purine (216 mg, 1.00 mmol), 3-(bromomethyl)-benzonitrile (196 mg, 1.00 mmol, Br-L$_{29}$), m-nitrobenzylbromide (216 mg, 1.00 mmol, Br-L$_8$), and m-bromobenzyl bromide (250 mg, 1.00 mmol, Br-L$_{30}$). The crude material was treated with 2-mercaptoethanesulfonic acid, sodium salt to give Library 53 as a foam (552 mg). MS(ES−) m/z: 560, 580, 600, 615, 621, 635, 655, 668, 688, 723.

Example 93

Preparation of Library 54

The title library was prepared as per the procedures of Example 90 using 2,6,8-tris(mercapto)-9H-purine (216 mg, 1.00 mmol), 2-bromo-N'-(2'-ethyl-bis-N-tert-butoxycarbonyl-guanidino)-acetamide (254 mg, 0.60 mmol, Br-L$_{31}$), N'-4'-(bromoacetyl)-piperazino-N'-1'-(bis-N-tert-butoxycarbonyl-1-carboxamidine (270 mg, 0.60 mmol, Br-L$_{32}$), 2-bromo-N-(2'-ethyl-N'-tert-butoxycarbonylamino)-acetamide (169 mg, 0.60 mmol, Br-L$_{33}$), N-(α-bromoacetyl)-3-amino-5-methylisoxazole-(131 mg, 0.60 mmol, Br-L$_{11}$), and N-(α-Bromoacetyl)-2-aminobenzothiazole (163 mg, 0.60 mmol, Br-L$_4$). The crude material was treated with 2-mercaptoethanesulfonic acid, sodium salt to give a solid (1.03 g). The solid was dissolved in 5N HCl-MeOH and the solution was stirred at ambient temperature for 1 hour after which time the solvent was evaporated in vacuo at ambient temperature to give Library 54 as the HCl salt as a foam (903 mg). MS(ES+) m/z: 259 [M+2H$^+$], 278 [M+2H$^+$], 280 [M+2H$^+$], 293 [M+2H$^+$], 300 [M+2H$^+$], 301 [M+2H$^+$], 304 [M+2H$^+$], 313 [M+2H$^+$], 314 [M+2H$^+$], 320 [M+2H$^+$], 325 [M+2H$^+$], 333 [M+2H$^+$], 338 [M+2H$^+$], 346 [M+2H$^+$], 359 [M+2H$^+$], 372 [M+2H$^+$], 630 259 [M+H$^+$], 635 [M+H$^+$], 653 [M+H$^+$], 675 [M+H$^+$], 687 [M+H$^+$], 697 [M+H$^+$], 713 [M+H$^+$], 739 [M+H$^+$], 765 [M+H$^+$].

Example 94

Preparation of Library 55

The title library was prepared as per the procedures of Example 90 using 2,8-bis(mercapto)-6-hydroxypurine (200 mg, 1.00 mmol), 2-bromo-N'-(2'-ethyl-bis-N-tert-butoxycarbonylguanidino)-acetamide (121 mg, 0.286 mmol, Br-L$_{31}$), N'-4'-(bromoacetyl)-piperazino-N'-1'-(bis-N-tert-butoxy-carbonyl-1-carboxamidine (128 mg, 0.286 mmol, Br-L$_{32}$), 2-bromo-N-(2'-ethyl-N'-tert-butoxycarbonylamino)-acetamide (80.3 mg, 0. 286 mmol, Br-L$_{33}$), N-4-(bromoacetyl)-N-1-(tert-butoxycarbonyl)-piperazine (87.8 mg, 0.286 mmol, Br-L$_{34}$), 2-bromo-N-3'-

(5'-methylisoxazole)-acetamide (62.6 mg, 0.286 mmol, Br-L$_{11}$), N-(α-bromoacetyl)-4-methyl-2-amino-thiazole-(67.2 mg, 0.286 mmol, Br-L$_{26}$), and N-(α-Bromoacetyl)-2-aminobenzothiazole (77.5 mg, 0.286 mmol, Br-L$_4$). The crude material was treated with 2-mercaptoethanesulfonic acid, sodium salt to give the title library as a hygroscopic foam (661 mg). MS(ES+) m/z: 401, 427, 443, 453, 455, 469, 481, 485, 491, 495, 497, 509, 511, 517, 523, 533, 545, 559, 581.

Example 95

Preparation of Library 56

The title library was prepared as per the procedures of Example 90 using dithiouracil (144 mg, 1.00 mmol), 2-bromo-N'-(2'-ethyl-bis-N-tert-butoxycarbonylguanidino)-acetamide (121 mg, 0.286 mmol, Br-L$_{31}$), 2-bromo-N-(2'-ethyl-N'-tert-butoxycarbonylamino)-acetamide (80.3 mg, 0.286 mmol, Br-L$_{33}$), N-4-(bromoacetyl)-N-1-(tert-butoxycarbonyl)-piperazine (87.8 mg, 0.286 mmol, Br-L$_{34}$), N-(α-bromoacetyl)-m-nitroaniline (74.0 mg, 0.286 mmol, Br-L$_2$), N-(α-bromoacetyl)-3-amino-5-methylisoxazole (62.6 mg, 0.286 mmol, Br-L$_{11}$), N-(α-bromoacetyl)-4-methyl-2-amino-thiazole-(67.2 mg, 0.286 mmol, Br-L$_{26}$),N-(α-Bromoacetyl)-2-aminobenzothiazole (77.5 mg, 0.286 mmol, Br-L$_4$). The crude material was treated with 2-mercaptoethanesulfonic acid, sodium salt to give the title library as the HCl salt as an oil (754 mg). MS(ES+) m/z: 206 [M+2H$^+$], 215 [M+2H$^+$], 257 [M+2H$^+$], 345 [M+H$^+$], 371 [M+H$^+$], 383 [M+H$^+$], 387 [M+H$^+$], 399 [M+H$^+$], 413 [M+H$^+$], 423 [M+H$^+$], 425 [M+H$^+$], 435 [M+H$^+$], 441 [M+H$^+$]449 [M+H$^+$], 461 [M+H$^+$], 465 [M+H$^+$], 477 [M+H$^+$]. MS(ES−) m/z: 471, 487, 499, 511, 523.

Example 96

Preparation of Library 57

The title library was prepared as per the procedures of Example 90 using dithiouracil (144 mg, 1.00 mmol), 2-bromo-N'-(2'-ethyl-bis-N-tert-butoxycarbonylguanidino)-acetamide (106 mg, 0.25 mmol, Br-L$_{31}$), 2-bromo-N-(2'-ethyl-N'-tert-butoxycarbonylamino)-acetamide (70 mg, 0.25 mmol, Br-L$_{33}$), N-(α-bromoacetyl)-m-nitroaniline (65 mg, 0.25 mmol, Br-L$_2$), N-(α-Bromoacetyl)-2-aminobenzothiazole (68 mg, 0.25 mmol, Br-L$_4$). The crude material was treated with 2-mercaptoethanesulfonic acid, sodium salt to give the title library as the HCl salt as a solid (445 mg). MS(ES+) m/z: 345, 387, 423, 429, 435, 465, 477, 501, 513, 525.

Example 97

Preparation of Library 58

The title library was prepared as per the procedures of Example 90 using 4,5-diamino-2,6-dimercaptopyrimidine (193 mg, 1.00 mmol), 2-bromo-N'-(2'-ethyl-bis-N-tert-butoxycarbonylguanidino)-acetamide (121 mg, 0.286 mmol, Br-L$_{31}$), N'-4'-(bromoacetyl)-piperazino-N'-1'-(bis-N-tert-butoxycarbonyl-1-carboxamidine (128 mg, 0.286 mmol, Br-L$_{32}$), 2-bromo-N-(2'-ethyl-N'-tert-butoxycarbonylamino)-acetamide (80.3 mg, 0.286 mmol, Br-L$_{33}$), N-4-(bromoacetyl)-N-1-(tert-butoxycarbonyl)-piperazine (87.8 mg, 0.286 mmol, Br-L$_{34}$),N-(α-bromoacetyl)-3-amino-5-methylisoxazole (62.6 mg, 0.286 mmol, Br-L$_{11}$), N-(α-bromoacetyl)-4-methyl-2-amino-thiazole-(67.2 mg, 0.286 mmol, Br-L$_{26}$), and N-(α-Bromoacetyl)-2-aminobenzothiazole (77.5 mg, 0.286 mmol, Br-L$_4$). The crude material was treated with 2-mercaptoethanesulfonic acid, sodium salt to give the title library as the HCl salt as a hygroscopic foam (664 mg). MS(ES−) m/z: 400, 416, 427, 454, 469, 480, 495, 506, 517. MS(ES+) m/z: 373, 457.

Example 98

2-(N2-t-BOC)piperazinyl-4-chloromethyl-6-chloropyrimidine

A solution of 4-chloromethyl-2,6-dichloropyrimidine (10.4 g, 50 mmol, 95%), MeOH (50 mL), trietylyamine (15 mL, 110 mmol) and N-t-BOC-piperazine (9.3 g, 50 mmol) was heated for 20 hours at 45° C. The solution was cooled, concentrated, partitioned between EtOAc/H$_2$O and separated. The EtOAc phase was dried (MgSO$_4$) and concentrated. The resulting gum was purified by silica gel flash column chromatography using a gradient mixture of EtOAc and hexane to afford 11.4 g (68%) of the title compound. $^1$HNMR (CDCL$_3$): δ 1.49 (s, 9H, t-BOC), 3.56–3.70 (m, 4H, piperazine), 4.48 (s, 2H, CH$_2$Cl), 6.62 (s,1H, C5H).

Example 99

2-(N2-t-BOC)Piperazinyl-4-piperazinylmethyl-6-piperazinyl-pyrimidine

A solution of 2-(N2-t-BOC)piperazinyl-4-chloromethyl-6-chloro pyrimidine (12 g, 34 mmol), p-dioxane (1000 mL), N,N-diisopropylethylamine (70 mL, 400 mmol) and piperazine (75 g, 870 mmol) was refluxed for 16 hours. The suspension was then cooled, filtered and the mother liquor concentrated. The resulting oil was heated at reduced pressure to 100° C. for 16 hours. The resulting viscous oil was purified by silica gel flash column chromatography using MeOH:NH4OH (9/1, v/v) to give 11.0 g (72%) of the title compound. $^1$H NMR (DMSO): δ 1.43 (s, 9H, t-BOC), 2.33 (m,4H, piperazine), 2.7 (m, 8H, piperazine), 3.2 (s, 2H, CH$_2$), 3.38–3.57 (m, 12H, piperazine), 6.1 (s, 1H, C5H).

Example 100

2-Piperazinyl-4-(piperazinylmethyl-6-piperazinyl-pyrimidine ·6HCl

A solution of 2-(N2-t-BOC)piperazinyl-4-piperazinylmethyl-6-piperazinyl-pyrimidine (0.56 g, 1.3 mmol) in MeOH (30 mL) was treated with HCl (gas) 3.3 g/MeOH (30 mL) for 16 hours at room temp. The solution was concentrated to reduce the volume and EtOAc was added. The suspension was concentrated, leaving a solid. The solid material was triturated with ether to give 0.5 g of the title compound as the hydrochloride. Anal. Calcd. for C$_{17}$H$_{36}$Cl$_{16}$N$_8$ C, 36.12; H, 6.42; N,19.83 Found: C, 35.82; H, 6.70; N,19.70.

Example 101

2,4-Di(t-BOC-1-piperazinyl)-6-chloropyrimidine

A solution of 2,4,6-trichloropyrimidine (31.5 g, 172 mmol), triethylamine(210 mL, 1450 mmol), tert-butyl-1-piperazine carboxylate (70 g, 375 mmol) in EtOH (1500 mL) was refluxed for 4 hours. The mixture was filtered and the filter cake was dried under high vacuum to give 36.6 g (72%) of the title compound. $^1$H NMR (CDCl$_3$): δ 1.44 (s, 9H, t-boc), 3.42–3.70 (m, 16H, piperazine), 5.84 (s, 1H, C$_5$H).

Example 102

2,4-Di(t-BOC-1-piperazinyl)-6-hydrazino-pyrimidine

A solution of 2,4-di(t-BOC-1-piperazinyl)-6-chloropyrimidine (50.5 g, 105 mmol) and hydrazine (174 g, 5540 mmol) in p-dioxane (1200 mL) was heated at 85° C. for 16 hours. The solution was concentrated and the resultant solid triturated with EtOAc to afford 46 g (92%) of the title compound. $^1$H NMR (CDCl$_3$) δ 1.47 (s, 18H, t-BOC), 3.46–3.7 (m, 16H, piperazine), 5.27 (s, 1H, C5H), 5.82 (bs, 2H, NH$_2$).

Example 103

2,4-di(t-BOC-1-piperazinyl)-6-aminopyrimidine

A suspension of 2,4-di(t-BOC-1-piperazinyl)-6-hydrazino-pyrimidine (5.0 g, 10 mmol) and Raney Ni (3 g) in EtOAc (250 mL) was shaken in a Parr hydrogenator/shaker at 50 psi H$_2$ for 16 hours. The resulting suspension was filtered through celite and the filtrate concentrated. The resultant solid was triturated with ether to afford 4.1 g (85%) of the title compound. $^1$H NMR (CDCl$_3$) δ 1.47 (s, 18H, t-BOC), 3.41–3.7 (m, 16H, piperazine), 4.37 (bs, 2H, NH$_2$), 5.1 (s, 1H, C5H).

Example 104

2,4-Di(t-BOC-1-piperazinyl)-6-N-benzyl-2,6-diketopiperazine-pyrimidine

A suspension of N-benzylimino diacetic acid (20 g, 88 mmol) and 1,1'-carbonyldiimadazole (31 g, 190 mmol) in p-dioxane (800 mL) was heated at reflux for 20 minutes until cessation of gas evolution. The solution was cooled and 2,4-di(t-BOC-1-piperazinyl)-6-aminopyrimidine (23.6 g, 51 mmol) was added. The reaction was heated to reflux for 16 hours. The reaction mixture was concentrated and the residue was dissolved in CH$_2$Cl$_2$. The CH$_2$Cl$_2$ solution was washed with HCl (5%, aq), H$_2$O, dil. NaHCO$_3$ and brine. The CH$_2$Cl$_2$ phase was then dried (MgSO$_4$), filtered and concentrated. Trituration with MeOH gave 20.5 g (72%) of the title compound. $^1$H NMR (CDCl$_3$) δ 1.48 (s, 18H, t-BOC), 3.45–3.74 (m, 22H, piperazine, diketopiperazine, CH$_2$), 5.73 (s, 1H, C$_5$H), 7.34 (m, 5H, Ar).

Example 105

2,4-Di(N-benzylpiperazinyl)-6-chloropyrimidine

A solution of 2,4,6-trichloropyrimidine (9.43 g, 50 mmol), triethylamine (60 mL, 430 mmol) and N-benzylpiperazine (19.8 g, 110 mmol) in EtOH (500 mL) was heated to 50° C. for 16 hours. The reaction mixture was concentrated and the resulting residue purified by silica gel flash column chromatography using ethyl acetate:hexane (9/1, v/v) as the eluent. The appropriate fractions were combined and concentrated to give 20.2 g (87%) of the title compound (m.p. 151–152° C.). $^1$H NMR δ (CDCl$_3$) 2.44 (m, 8H, piperazine), 3.52–3.59 (m, 8H, piperazine), 3.72 (m, 4H, CH$_2$), 5.82 (s, 1H, C$_5$H), 7.30 (m, 10H, Ar).

Example 106

2,4-Di(N-benzylpiperazinyl)-6-hydrazinopyrimidine

A solution of 2,4-di(N-benzylpiperazinyl)-6-chloropyrimidine (48.4 g, 104 mmol), hydrazine (96 g, 3 mol), in p-dioxane (1000 mL) was heated at 75° C. for 16 hours. The reaction was concentrated, dissolved in CH$_2$-Cl$_2$, washed with H$_2$O, and dried (MgSO$_4$). Filtration and concentration of the resulting solution gave 46 g (97%) of the title compound as a foam. $^1$H NMR (CDCl$_3$) δ 2.44 (m, 8H, piperazine), 3.52–3.59 (m, 8H, piperazine), 3.71 (m, 4H, CH$_2$), 5.22 (s, 1H, C$_5$H), 5.72 (bs, 2H, NH$_2$), 7.30 (m, 10H, Ar).

Example 107

2,4-Di(N-benzylpiperazinyl)-6-aminopyrimidine

A suspension of 2,4-di(N-benzylpiperazinyl)-6-hydrazino pyrimidine (19.7 g, 43 mmol) and Raney Ni (5 g) in EtOAc (250 mL) was shaken in a Parr hydrogenator at 50 psi H$_2$ for 16 hours. The resulting suspension was filtered through celite and the filtrate was concentrated to give 18 g (94%) of the title compound as a foam. $^1$H NMR (CDCl$_3$) δ 2.47 (m, 8H, piperazine), 3.51 (m, 8H, piperazine), 3.77 (m, 4H, CH$_2$), 4.30 (bs, 2H, NH$_2$), 5.04 (s, 1H, C$_5$H), 7.3 (m, 10H, Ar).

Example 108

1,3-Dibenzylpiperazine-8-benzyl-7,8,9,10-tetrahydro-pyrimido[4,5-c][2,7]naphthyridin-6(5H, 8H)-one A solution of 2,4-Di(N-benzylpiperazinyl)-6-aminopyrimidine and 1-benzyl-3-carboethoxy-4-pyrrolidone (9.6 g, mmol) in HOAc (1000 mL) was heated to reflux for 16 hours. The solution was concentrated under reduced pressure to an oil. The oil was dissolved in H$_2$O and the pH was adjusted to 13 with 20% NaOH. The orange precipitate that formed was collected and dried. The solid was further purified by silica gel flash column chromatography using ethyl acetate:methanol (9/1, v/v) as the eluent. Concentration and drying of the appropriate fractions gave 17 g of the title compound. $^1$H NMR (CDCl$_3$) δ 2.33–2.55 (m, 10H, piperazine, CH$_2$), 3.29–3.67 (m, 16H, piperazine, CH$_2$Ar, CH$_2$), 4.62 (s, 2H, CH$_2$Ar), 6.26 (bs, 1H, NH) 7.25 (m, 15H, Ar)

Example 109

Preparation of Library 59, 2-(N-t-BOC)piperazinyl-4(N-L$_{6, 8, 9, 10, 27, 28, 29, 30, 35, and 36}$)-piperazinylmethyl-6-(N-L$_{6, 8, 9, 10, 27, 28, 29, 30, 35, and 36}$) piperazinyl-pyrimidine The title library was prepared by adding dropwise a solution of 10 selected alkylating agents (2.4 mmol each) (benzyl bromide, Br-L$_{35}$; m-chlorobenzylbromide, Br-L$_6$; m-bromobenzyl bromide, Br-L$_{30}$; α-Bromo-m-xylene, Br-L$_{27}$; m-triflouromethylbenzylbromide, Br-L$_{10}$; m-nitrobenzylbromide, Br-L$_8$; m-methylesterbenzylbromide, Br-L$_9$; 3-(bromomethyl)-benzonitrile, Br-L$_{29}$; m-fluoro-benzylbromide, L$_{28}$; and cinnamyl bromide, L$_{36}$) in CH$_3$CN (150 mL) to a suspension of 2-(N-t-BOC)piperazinyl-4-piperazinylmethyl-6-piperazinyl-pyrimidine (g, mmol) and K$_2$CO$_3$ (5 g, 36 mmol) in CH$_3$CN (200 mL). After the addition was complete the mixture was stirred for 2 hours. The suspension was filtered and the filtrate was concentrated. The resultant gum was partitioned between CH$_2$Cl$_2$/H$_2$O and the CH$_2$Cl$_2$ layer was dried (MgSO$_4$) and concentrated to a foam. The foam was purified by silica gel flash column chromatography using ethyl acetate:methanol (8/2, v/v) as the eluent. The appropriate fractions were concentrated and dried to give 7.34 g of the title library. Theoretical M.S. m+H+ 627.76–785.56; observed M.S. m+H+ 627–786.

Example 110

Preparation of Library 60, 2-piperazinyl-4-(N-L$_{6, 8, 9, 10, 27, 28, 29, 30, 35, \text{ and } 36}$)-piperazinylmethyl-6-(N-L$_{6, 8, 9, 10, 27, 28, 29, 30, 35, \text{ and } 36}$)-piperazinyl-pyrimidine A solution of Library 59 (0.71 g, 1 mmol) in MeOH (70 mL) was treated with a solution of HCl (4.1 g, gas) in methanol (50 mL) for 16 hours at ambient temperature. The solution was concentrated and triturated with ether to give 0.85 g of the title library.

Example 111

Preparation of Library 61, 2-(N-L$_{6, 8, 9, 10, 27, 28, 29, 30, 35, \text{ and } 36}$) piperazinyl-4-(N-L$_{6, 8, 9, 10, 27, 28, 29, 30, 35, \text{ and } 36}$)-piperazinylmethyl-6-(N-L$_{6, 8, 9, 10, 27, 28, 29, 30, 35, \text{ and } 36}$) piperazinyl-pyrimidine The title library is prepared as per the procedures illustrated in Example 109. Library 60 is treated with the selected 10 alkylating agents to give the title library.

Example 112

2,4-Di(piperazinyl)-6-(N-benzyl-2,6-diketopiperazine-pyrimidine·6HCl

A solution of 2,4-di(t-BOC-1-piperazinyl)-6-(N-benzyl-2,6-diketopiperazine-pyrimidine (1.3 mmol) in MeOH (30 mL) is treated with HCl (gas) 3.3 g/MeOH (30 mL) for 16 hours at room temp. The solution is concentrated to reduce the volume and EtOAc is added. The suspension is concentrated and the crude material is triturated with ether to give the title compound as the hydrochloride.

Example 113

Preparation of Library 62, 2,4-Di[(N-L$_{6, 8, 9, 10, 27, 28, 29, 30, 35, \text{ and } 36}$) piperazinyl]-6-(N-benzyl-2,6-diketopiperazine)-pyrimidine 2,4-Di(piperazinyl)-6-(N-benzyl-2,6-diketopiperazine)-pyrimidine. 6HCl is treated as per the procedures illustrated in Example 109 to give the title library.

Example 114

Bis-Boc-guanidinyl piperazine

A mixture of piperazine (34.46 g, 0.4 mol) and 1,3-bis(t-Boc)-2-methyl-2-thiopseudourea (29.0 g, 0.1 mol) in DMF (260 mL) was stirred at 50–60 ° C. for 2 hours. The solvent was evaporated to dryness and the residue was dissolved in water-chloroform. The organic phase was separated and the aqueous phase was extracted with chloroform. The combined organic phase was washed with brine, dried (Na$_2$SO$_4$) and concentrated. The residue was purified by silica gel flash column chromatography initially using hexanes:EtOAc (½, v/v) and ending with EtOAc:MeOH (1/1, v/v) as eluents to afford 27.2 g (83%) of the title compound as a white solid. Silica gel TLC R$_f$ 0.34 (100% MeOH). $^1$H NMR (CDCl$_3$) δ 1.42 (s, 18H), 2.78–2.91 (m, 4H), 3.40–3.66 (m, 4H). HRMS (FAB) m/z 329.218 (M+H)$^+$ (C$_{15}$H$_{29}$N$_4$O$_4$ requires 329.218).

Example 115

N-Bromoacetyl-N(bis-Boc-guanidinyl)piperazine

A solution of bromoacetyl bromide (2.06 g, 10.2 mmol) in THF (20 mL) was added dropwise to a stirred solution of bis-t-Boc-guanidinyl piperazine (3.28 g, 10 mmol) and diisopropylethylamine (2.1 mL, 1.56 g, 12 mmol) in THF (50 mL) at −30° C. The dry ice/acetone bath was removed and the reaction mixture was stirred for an additional 1.5 hours. The mixture was concentrated and the resulting residue was dissolved in chloroform. The resultant solution was washed with water, brine, dried (Na$_2$SO$_4$) and concentrated. The residue was purified by silica gel flash column chromatography using hexanes:EtOAc (5/1, 2/1 and then 1/1, v/v) to give 3.5 g (78%) of the title compound as a white solid. Silica gel TLC R$_f$ 0.45 hexanes:EtOAc (½, v/v). $^1$H NMR (CDCl$_3$)δ 1.46 (s, 18H), 3.48–3.75 (m, 8H), 3.85 (s, 2H). HRMS (FAB) m/z 449.141 (M+H)$^+$ (C$_{17}$H$_{30}$N$_4$BrO$_5$ requires 449.140).

Example 116

N-(4-chloromethylbenzoyl)-N(bis-Boc-guanidinyl)-piperazine

The title compound was prepared as per the procedures illustrated for Example 115 using bis-t-Boc-guanidinyl piperazine (6.56 g, 20 mmol), 4-chloromethyl benzoyl chloride (3.88 g, 20 mmol) and diisopropylethyl amine (4.2 mL, 3.1 g, 24 mmol) in THF (150 mL). Purification gave 9.6 g (98%) of the title compound as a white solid. Silica gel R$_f$ 0.38 hexanes:EtOAc (1:1, v/v). $^1$H NMR (CDCl$_3$) δ 1.36 (s, 18H), 3.25–3.80 (m, 8H), 4.48 (s, 2H), 7.25–7.37 (m, 4H), 10.05 (br, 1H). MS (FAB) m/z 503 (M+Na)$^+$. HRMS (FAB) m/z 481.220 (M+H)$^+$ (C$_{23}$H$_{34}$N$_4$ClO$_5$ requires 481.221).

Example 117

N-(3-chloromethylbenzoyl)-N(bis-Boc-guanidinyl)piperazine

The title compound was prepared as per the procedures illustrated for Example 115 using bis-t-Boc-guanidinyl piperazine (3.28 g, 10 mmol), 3-chloromethyl benzoyl chloride (1.94 g, 10.26 mmol) and diisopropylethyl amine (2.1 mL, 1.56 g, 12 mmol) in THF (70 mL). Purification gave 4.33 g (90%) of the title compound as a white solid. Silica gel R$_f$ 0.42 hexanes:EtOAc (1/1, v/v). $^1$H NMR (CDCl$_3$) δ 1.37 (s, 18H), 3.28–3.85 (m, 8H), 4.48 (s, 2H), 7.20–7.40 (m, 4H), 10.10 (br, 1H); MS (FAB) m/z 503 (M+Na)$^+$. HRMS (FAB) m/z 481.222 (M+H)$^+$ (C$_{23}$H$_{34}$N$_4$ClO$_5$ requires 481.221).

PROCEDURE 1

Antimicrobial Assays

A. *Streptococcus Pyogenes*

In this assay, the strain *S. aureus* ATCC 14289 (American Type Culture Collection) is used in the bioassay. To initiate the exponential phase of bacterial growth prior to the assay, a sample of bacteria is grown overnight at 37° C. in 1× Todd-Hewitt broth. This bacteria is then used to reinoculate sample wells of 96-well microtiter plates. The assays are carried out in the 96-well microtiter plates in 150 μL volume with approximately 1×10$^6$ cells per well.

Bacteria in 1× Todd-Hewitt broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

B. E. coli imp-

In this assay, the strain E. coli imp- obtained from Spenser Bensen (Sampson., B. A., Misra, R. & Benson, S. A. (1989), Genetics, 122, 491–501, Identification and characterization of a new gene of Escherichia coli K-12 involved in outer membrane permeability) is used. To initiate the exponential phase of bacterial growth prior to the assay, a sample of bacteria is grown overnight at 37° C. in Luria broth. This bacteria is then used to reinoculate sample wells of 96-well microtiter plates. The assays are carried out in the 96-well microtiter plates in 150 $\mu$L volume with approximately 1×10$^6$ cells per well.

Bacteria in Luria broth (75 $\mu$L) is added to the compound mixtures in solution in 75 $\mu$L water in the individual well of the microtiter plate. Final concentrations of the compound mixtures are 25 $\mu$M, 10 $\mu$M and 1 $\mu$M. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

C. Staphylococcus aureus

Staphylococcus aureus is known to cause localized skin infections as a result of poor hygiene, minor trauma, psoriasis or eczema. It also causes respiratory infections, pneumonia, toxic shock syndrome and septicemia. It is a common cause of acute food poisoning. It exhibits rapid emergence of drug resistance to penicillin, cephalosporin, vancomycin and nafcillin.

In this assay, the strain S. aureus ATCC 25923 (American Type Culture Collection) is used in the bioassay. To initiate the exponential phase of bacterial growth prior to the assay, a sample of bacteria is grown overnight at 37° C. in typtocase soy broth (BBL). This bacteria is then used to reinoculate sample wells of 96-well microtiter plates. The assays are carried out in the 96-well microtiter plates in 150 $\mu$L volume with approximately 1×10$^6$ cells per well.

Bacteria in typtocase soy broth (75 $\mu$L) is added to the compound mixtures in solution in 75 $\mu$L water/4% DMSO in the individual well of the microtiter plate. Final concentrations of the compound mixtures are 25 $\mu$M, 10 $\mu$M and 1 $\mu$M. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

Libraries in accordance with the present invention have been tested for antibacterial activity utilizing assays that determine the minimum inhibitory concentration (MIC). The antibacterial assays utilize streptococcus pyogenes and escherichia coli imp-. Activity has been detected in a number of libraries of the present invention.

| Library #/Ex. # | imp ($\mu$M) | S. pyogenes ($\mu$M) |
|---|---|---|
| Library 14/25 | 6–12 | 12–25 |
| Library 25/36 | 12–25 | >100 |
| Library 14/37 | ~50 | >100 |
| Library 29/40 | >50 | >50 |
| Library 30/41 | 12–25 | 12–25 |
| Library 31/42 | 12–25 | 12–25 |
| Library 32/42 | 12–25 | 12–25 |
| Library 33/42 | >50 | 25–50 |
| Library 34/42 | 6–12 | 6–12 |
| Library 35/42 | 12–25 | 25–50 |
| Library 36/42 | 12–25 | 12–25 |
| Library 37/42 | 12–25 | 12–25 |
| Library 38/42 | 12–25 | 12–25 |
| Library 39/42 | >50 | >50 |

Selected libraries have been deconvoluted to final compounds and tested for minimum inhibitory activity in the above assays. 6-[(2-Aminobenzothiazole acetyl)piperazinyl]-2-[(m-chlorobenzyl)-piperazinyl]-N9-[(N'-t-Boc-N"-acetyl)piperazinyl]purine-Compound 46 (Example 46) and 6-[(2-aminobenzothiazole acetyl)piperazinyl]-2-[(N-m-triflouromethylbenzyl)piper-azinyl]-N9-[(N'-t-Boc-N"-acetyl)piperazinyl]purine-Compound 50 (Example 50) were each deblocked as per the procedures illustrated in Example 25 and examined in selected antimicrobial assays.

| Assay | Compound 46 | Compound 50 |
|---|---|---|
| Streptococcus pyogenes | 3–6 $\mu$M | 3–6 $\mu$M |
| E. coli. imp- | 3–6 $\mu$M | 3 $\mu$M |
| Staphylococcus aureus | 3–6 $\mu$M | 3–6 $\mu$M |
| Entercoccus hirae | 3–6 $\mu$M | 3 $\mu$M |
| Escherichia coli | 50–100 $\mu$M | >100 |
| Klebsiella pneumoniae | 3–6 $\mu$M | 3–6 $\mu$M |

PROCEDURE 2

Antifungal Assay

C. albicans

In this assay, the strain C. albicans ATCC 10231 (American Type Culture Collection) is used in the bioassay. To initiate the exponential phase of yeast growth prior to the assay, a sample of yeast is grown overnight at 37° C. in YM media. This yeast is then used to reinoculate sample wells of 96-well microtiter plates. The assays are carried out in the 96-well microtiter plates in 150 $\mu$L volume with approximately 1×10$^6$ cells per well.

Yeast in YM media (75 $\mu$L) is added to the compound mixtures in solution in 75 $\mu$L water in the individual well of the microtiter plate. Final concentrations of the compound mixtures are 25 $\mu$M, 10 $\mu$M and 1 $\mu$M. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Amphotericin B positive control is concurrently tested in each screening assay.

PROCEDURE 3

RNA Binding Assay

The Effect of Libraries on tat/TAR Interactions

A. ELISA Method

The effects of libraries on tat/TAR, RNA/protein interactions are examined using a rapid and reproducible binding assay. The assay consists of a biotinylated truncated version of the HIV-1 TAR stem-loop, which is anchored to the wells of a 96 well ELISA plate which has been coated with streptavidin. The TAR RNA is recognized by the HIV-1 protein tat and the amount of tat bound is quantitated using an antibody raised against tat and a secondary antibody conjugated to an alkaline phosphatase or HRP enzyme to produce a calorimetric reaction.

Materials:

A 39 residue tat peptide (aa 49–85 of HIV tat protein). This is the C terminal basic binding domain of the tat protein. This peptide was synthesized by a contract lab.

A 30 base RNA oligonucleotide consisting of the bulge and stem/loop structure of HIV TAR which has also been Biotin conjugated. This RNA oligonucleotide was synthesized in house.

A biotinylated HIV RRE RNA oligonucleotide synthesized in house.

Binding buffer: 40 mM Tris-HCl (pH 8.0), 0.01% NP-40, 20% glycerol, 1.5 mM $MgCl_2$, 0.01% $NaN_3$, 50 mM KCl.

Streptavidin coated 96 well microtitre plates (Elkay Labsystems).

Protein A/G alkaline phosphatase (Pierce).

Anti tat antiserum (BioDesign).

PNPP substrate (Pierce).

Methods:

To each well of a Streptavidin coated 96 well ELISA plate is added 200 µl of a solution of the 30 base TAR sequence (20 nM) in binding buffer. The plate is incubated at 4° C. for 1 hour. The biotintylated HIV RRE RNA oligonucleotide is bound to selected wells as a negative control RNA. The plate is washed with binding buffer three times and 100 µl of a 100 nM solution of the 39 residue tat peptide in binding buffer is added to each well. Libraries are added to selected wells of the plate at initial concentrations of 100 µM. The plate is incubated for 1 hour at room temperature.

The plate is washed with binding buffer three times and blocked with binding buffer+5% FCS. 100 µl of tat antiserum diluted 1:700 in binding buffer is added to the wells of the plate and the plate is incubated for 1.5 hours at 4° C. The plate is washed three times with binding buffer and 150 µL of a solution of protein A/G alkaline phosphatase diluted 1:5000 in binding buffer is added to each well. The plate is incubated for 1.5 hours at 4° C. followed by washing three times with binding buffer. 150 µL of PNPP substrate is added to each well and the plate is incubated for 1 hour at 37° C. The absorbance of each well is read in a multiwell plate reader.

B. SPA Method (Scintillation Proximity Assay)

A faster assay targeting tat/TAR interactions was developed for high through-put screening. The assay is used to rapidly identify compounds which are capable of disrupting the interaction of HIV-1 tat protein with the TAR RNA stem/loop structure.

Materials:

A 39 residue tat peptide (aa 48–86 of HIV-1 tat protein). This is the C terminal basic binding domain of the tat protein. This peptide was synthesized by a contract lab and further labeled with $^{125}I$ (specific activity 100 µCi/mL) at Amersham Life Sciences.

A 30 base RNA oligonucleotide (TAR oligonucleotide) consisting of the bulge and stem/loop structure of HIV TAR which has also been Biotin conjugated at the 3' end. This RNA oligonucleotide was synthesized in house.

PRB buffer: 50 mM Tris-HCl (pH 8.0), 0.01% NP-40, 10% glycerol, 1.5 mM $MgCl_2$, and 50 mM KCl.

Streptavidin coated SPA beads(Amersham Life Sciences).

Opaque 96 well plates.

Methods:

Streptavidin coated SPA beads are incubated for 20 minutes at room temperature in a PRB buffer with 0.1 µCi of the labeled peptide and 100 nM of the biotin conjugated RNA oligonucleotide. Incubations are performed in the presence or absence of test samples in a volume of 50 µl in an opaque 96 well plate. Following the incubation the plates are spun at 1000 rpm for 5 minutes to settle the SPA beads. The biotintylated TAR oligonucleotide binds the steptavidin coated SPA bead. The labeled tat peptide associated with the biotintylated TAR oligonucleotide excites the scintillant in the SPA bead, resulting in a quantifiable signal which can be read in the TopCount 96 well scintillation counter. Compounds that interfere with the tat/TAR interaction result in $^{125}I$ tat floating free in buffer where excited electrons are quenched before transferring energy to scintillant in the SPA bead. This is observed as a decrease in signal.

Library 51, from Example 90, was observed in the above tat/TAR SPA assay to have an $IC_{50}$ of about 10 µM. This library has a complexity of 27 compounds and is currently undergoing deconvolution studies.

PROCEDURE 4

Antimicrobial Mechanistic Assay

Bacterial DNA Gyrase

DNA gyrase is a bacterial enzyme which can introduce negative supercoils into DNA utilizing the energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all library pools are screened for inhibitory activity at 30 µM and then a dose response analysis is effected with active subsets. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The $IC_{50}$ was determined to be 8 nM, sufficient to identify the activity of a single active species of comparable activity in a library having 30 µM concentration.

PROCEDURE 5

Using Libraries for Identifying Metal Chelators and Imaging Agents

This procedure is used to identify compounds of the invention from libraries of compounds constructed to include a ring that contains an ultraviolet chromophore. Further the chemical functional groups attached to the compounds of the invention are selected from metal binders, coordinating groups such as amine, hydroxyl and carbonyl groups, and other groups having lone pairs of electrons, such that the compounds of the invention can form coordination complexes with heavy metals and imaging agents. The procedure is used to identify compounds of the invention useful for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the pool under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library pool being assayed.

PROCEDURE 6

Assay of Combinatorial Library for PLA$_2$ Inhibitors

A preferred target for assay of combinatorially generated pools of compounds is the phospholipase A$_2$ family. Phospholipases A$_2$ (PLA$_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, New York, 1983). Elevated levels of type II PLA$_2$ are correlated with a number of human inflammatory diseases. The PLA$_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lyso-phospholipid can be a precursor to platelet-activating factor. PLA$_2$ is regulated by pro-inflammatory cytokines and, thus, occupies a central position in the inflammatory cascade (Dennis, ibid.; Glaser et al., *TiPs Reviews* 1992, 14, 92; and Pruzanski et al., *Inflammation* 1992, 16, 451). All mammalian tissues evaluated thus far have exhibited PLA$_2$ activity. At least three different types of PLA$_2$ are found in humans: pancreatic (type I), synovial fluid (type II) and cytosolic. Studies suggest that additional isoenzymes exist. Type I and type II, the secreted forms of PLA$_2$, share strong similarity with phospholipases isolated from the venom of snakes. The PLA$_2$ enzymes are important for normal functions including digestion, cellular membrane remodeling and repair, and in mediation of the inflammatory response. Both cytosolic and type II enzymes are of interest as therapeutic targets. Increased levels of the type II PLA$_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of PLA$_2$ in promoting the pathophysiology observed in certain chronic inflammatory disorders was the observation that injection of type II PLA$_2$ into the footpad of rats (Vishwanath et al., *Inflammation* 1988, 12, 549) or into the articular space of rabbits (Bomalaski et al., *J. Immunol.* 1991, 146, 3904) produced an inflammatory response. When the protein was denatured before injection, no inflammatory response was produced.

The type II PLA$_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted PLA$_2$ enzymes from venom and pancreatic PLA$_2$, with and without inhibitors, have been reported (Scott et al., *Science* 1990, 250, 1541). Recently, the crystal structure of PLA$_2$ from human synovial fluid has been determined (Wery et al., *Nature* 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., *Cold Spring Harbor Symp. Quant. Biol.* 1987, 52, 441; Cho et al., *J. Biol. Chem.* 1988, 263, 11237; Yang et al., *Biochem. J.* 1989, 262, 855; and Noel et al., *J. Am. Chem. Soc.* 1990, 112, 3704).

Much work has been reported in recent years on the study of the mechanism and properties of PLA$_2$-catalyzed hydrolysis of phospholipids. In in vitro assays, PLA$_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in PLA$_2$ activity occur concurrently with changes in the fluorescence of a membrane probe (Burack et al., *Biochemistry* 1993, 32, 583). This suggests that lipid rearrangement is occurring during the interfacial activation process. PLA$_2$ activity is maximal around the melting temperature of the lipid, where regions of gel and liquid-crystalline lipid coexist. This is also consistent with the sensitivity of PLA$_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., *FEBS Lett.* 1989, 252, 73). These studies clearly show that PLA$_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of PLA$_2$ is that maximal catalytic activity is observed on substrate that is aggregated (i.e. phospholipid above its critical micelle concentration), while low levels of activity are observed on monomeric substrate. As a result, competitive inhibitors of PLA$_2$ either have a high affinity for the active site of the enzyme before it binds to the substrate bilayer or partition into the membrane and compete for the active site with the phospholipid substrate. Although a number of inhibitors appear to show promising inhibition of PLA$_2$ in biochemical assays (Yuan et al., *J. Am. Chem. Soc.* 1987, 109, 8071; Lombardo et al., *J. Biol. Chem.* 1985, 260, 7234; Washburn et al., *J. Biol. Chem.* 1991, 266, 5042; Campbell et al., *J. Chem. Soc., Chem. Commun.* 1988, 1560; and Davidson et al., *Biochem. Biophys. Res. Commun.* 1986, 137, 587), reports describing in vivo activity are limited (Miyake et al., *J. Pharmacol. Exp. Ther.* 1992, 263, 1302).

In one preferred embodiment, compounds of the invention are selected for their potential to interact with, and preferably inhibit, the enzyme PLA$_2$. Thus, compounds of the invention can be used for topical and/or systemic treatment of inflammatory diseases including atopic dermatitis and inflammatory bowel disease. In selecting the functional groups, advantage can be taken of PLA$_2$'s preference for anionic vesicles over zwitterionic vesicles. Preferred compounds of the invention for assay for PLA$_2$ include those having aromatic diversity groups to facilitate binding to the cleft of the PLA$_2$ enzyme (Oinuma et al., *J. Med. Chem.* 1991, 34, 2260; Marki et al., *Agents Actions* 1993, 38, 202; and Tanaka et al., *J. Antibiotics* 1992, 45, 1071). Benzyl and 4-hexylbenzyl groups are preferred aromatic diversity groups. $PLA_2$-directed compounds of the invention can further include hydrophobic functional groups such as tetraethylene glycol groups. Since the $PLA_2$ enzyme has a hydrophobic channel, hydrophobicity is believed to be an important property of inhibitors of the enzyme.

After each round of synthesis as described in the above examples, the resulting libraries or pools of compounds are screened for inhibition of human type II $PLA_2$ enzymatic activity. The assay is effected at the conclusion of each round of synthesis to identify the wining pool from that round of synthesis. Concurrently, the libraries additionally can be screened in other in vitro assays to determine further mechanisms of inhibition.

The pools of the libraries are screened for inhibition of $PLA_2$ in the assay using *E. coli* labeled with $^3$H-oleic acid (Franson et al., *J. Lipid Res.* 1974, 15, 380; and Davidson et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each of the library pools is done in water: 10 $\mu$l of each pool is incubated for 5 minutes at room temperature with a mixture of 10 $\mu$l $PLA_2$, 20 $\mu$l 5×$PLA_2$ Buffer (500 mM Tris 7.0–7.5, 5 mM $CaCl_2$) and 50 $\mu$l water. Samples of each pool are run in duplicate. At this point, 10 $\mu$l of $^3$H *E. coli* cells is added. This mixture is incubated at 37° C. for 15 minutes. The enzymatic reaction is stopped with the addition of 50 $\mu$L 2M HCl and 50 $\mu$L fatty-acid-free BSA (20 mg/mL PBS), vortexed for 5 seconds, and centrifuged at high speed for 5 minutes. 165 $\mu$L of each supernate is then put into a scintillation vial containing 6 ml of scintillant (ScintiVerse) and cpms are measured in a Beckman Liquid Scintillation Counter. As a control, a reaction without the combinatorial pool is run alongside the other reactions as well as a baseline reaction containing no compounds of the invention as well as no $PLA_2$ enzyme. CPMs are corrected for by subtracting the baseline from each reaction data point.

Confirmation of the "winners" is made to confirm that a compound of the invention binds to enzyme rather than substrate and that the inhibition by a compound of the invention that is selected is specific for type II $PLA_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and a compound of the invention. $^{14}$C-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

PROCEDURE 7

Probes for the Detection of Specific Proteins and mRNA in Biological Samples

For the reliable, rapid, simultaneous quantification of multiple varieties of proteins or mRNA in a biological sample without the need to purify the protein or mRNA from other cellular components, a protein or mRNA of interest from a suitable biological sample, i.e., a blood borne virus, a bacterial pathogen product in stool, urine and other like biological samples, is identified using standard microbiological techniques. A probe comprising a compound of a combinatorial library of the invention is identified by a combinatorial search as noted in the above examples. Preferred for the protein probe are compounds synthesized to include chemical functional groups that act as hydrogen bond donors and acceptors, sulfhydryl groups, hydrophobic lipophilic moieties capable of hydrophobic interactions groups and groups capable of ionic interactions. The probe is immobilized on insoluble CPG solid support utilizing the procedure of Pon, R. T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the probe thereon for a time sufficient to hybridize the protein or mRNA to the probe and thus form a linkage via the probe to the solid support. This immobilizes the protein or mRNA present in the sample to the CPG support. Other non-immobilized materials and components are then washed off the CPG with a wash media suitable for use with the biological sample. The mRNA on the support is labeled with ethidium bromide, biotin or a commercial radionucleotide and the amount of label immobilized on the CPG support is measured to indicate the amount of mRNA present in the biological sample. In a similar assay a protein is also labeled and quantified.

PROCEDURE 8

Leukotriene $B_4$ Assay

Leukotriene $B_4$ ($LTB_4$) has been implicated in a variety of human inflammatory diseases, and its pharmacological effects are mediated via its interaction with specific surface cell receptors. Library subsets are screened for competitive inhibition of radiolabeled $LTB_4$ binding to a receptor preparation.

A Nenquest™ Drug Discovery System Kit (NEN Research Products, Boston, Mass.) is used to select an inhibitor of the interaction of Leukotriene $B_4$ ($LTB_4$) with receptors on a preparation of guinea pig spleen membrane. [$^3$H]Leukotriene $B_4$ reagent is prepared by adding 5 mL of ligand diluent (phosphate buffer containing NaCl, $MgCl_2$, EDTA and Bacitracin, pH 7.2) to 0.25 mL of the radioligand. The receptor preparation is made by thawing the concentrate, adding 35 mL of ligand diluent and swirling gently in order to re-suspend the receptor homogeneously. Reagents are kept on ice during the course of the experiment, and the remaining portions are stored at −20° C.

Library subsets prepared as per general procedure of examples above are diluted to 5 $\mu$M, 50 $\mu$M and 500 $\mu$M in phosphate buffer (1×PBS, 0.1% azide and 0.1% BSA, pH 7.2), yielding final test concentrations of 0.5 $\mu$M, 5 $\mu$M and 50 $\mu$M, respectively. Samples are assayed in duplicate. [$^3$H]$LTB_4$ (25 $\mu$L) is added to 25 $\mu$L of either appropriately diluted standard (unlabeled $LTB_4$) or library subset. The receptor suspension (0.2 mL) is added to each tube. Samples are incubated at 4° C. for 2 hours. Controls include [$^3$H]$LTB_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total counts to determine the net cpm for each sample. The degree of inhibition of binding for each library subset is determined relative to the standard (sample of ligand and receptor without library molecules).

PROCEDURE 9
Red Blood Lysis Assay

Compositions are tested for hemolysis of mammalian red blood cells. Horse red blood cells (Colorado Serum Co. #CS0004) are diluted 1:5 in 1×phosphate buffered saline (PBS). 50 µL of test compound in 1×PBS (total volume= 1009 µL) in a round bottom 96-well microplate, mixed gently, and incubated for 1 hour at 37° C. The microplate is then centrifuged for 5 minutes at 1000 rpm. The supernatant is diluted 1:5 (20 µL supernatant +80 µL 1×PBS) into a clean flat bottom 96-well microplate. Absorbance at 540 nm is read using a BioRad model 3550 UV microplate reader.

Compounds are tested in duplicate at multiple doses to dertermine the minimum hemolytic concentration. A minimum hemolytic concentration of 50–100 µM was determined for Compound 46 in the assay.

Persons of skill in the art will appreciate that the foregoing examples are provided for purposes of illustration only and are not to be considered to be limiting.

What is claimed is:

1. A method for preparing a library of compounds of the formula

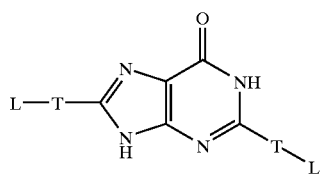

wherein:
each tether moiety T is —NHR$^1$NH—, —NH(R$^1$)O—, —NHR$^2$NH—, —NHR$^2$SO$_2$NH—, —NHR$^1$—, —N(R$^4$)$_2$, —N=N—, O, S, Se, —P(=O)(O)$_2$, NH, OR$^2$, OR$^3$, malonato, pyrrolidinyl, piperidinyl, piperazinyl, morpholino, imidazolyl, pyrrolyl, pyrazolyl, indolyl, 1H-indolyl, α-carbolinyl, carbazolyl, phenothiazinyl, phenoxazinyl, tetrazolyl, or triazolyl;

R$^1$ is alkylene; R$^2$ is aryl; R$^3$ is H or C$_1$–C$_{10}$ alkyl; R$^4$ is alkyleneoxy; and each chemical substituent L is, independently, C$_1$–C$_{10}$ alkyl, substituted C$_1$–C$_{10}$ alkyl, C$_2$–C$_{10}$ alkenyl, substituted C$_2$–C$_{10}$ alkenyl, C$_2$–C$_{10}$ alkynyl, substituted C$_2$–C$_{10}$ alkynyl, C$_4$–C$_7$ carbocyclic alkyl, substituted C$_4$–C$_7$ carbocyclic alkyl, C$_4$–C$_{10}$ alkenyl carbocyclic, substituted C$_4$–C$_{10}$ alkenyl carbocyclic, C$_4$–C$_{10}$ alkynyl carbocyclic, substituted C$_4$–C$_{10}$ alkynyl carbocyclic, C$_6$–C$_{14}$ aryl, substituted C$_6$–C$_{14}$ aryl, heteroaryl, substituted heteroaryl, a nitrogen, oxygen or sulfur containing heterocycle, a substituted nitrogen, oxygen or sulfur containing heterocycle, a mixed heterocycle, or a substituted mixed heterocycle; wherein each of the substituent groups is selected from a group consisting of alkyl, alkenyl, alkynyl, aryl, hydroxyl, alkoxy, benzyl, nitro, thiol, thioalkyl, thioalkoxy and halo; or L is, independently, phthalimido, an ether having 2 to 10 carbon atoms and 1 to 4 oxygen or sulfur atoms, hydrogen, halogen, hydroxyl, thiol, keto, carboxyl, NR$^1$R$^2$, CONR$^1$, amidine, guanidine, glutamyl, nitro, nitrate, nitrile, trifluoromethyl, trifluoromethoxy, NH-alkyl, N-dialkyl, O-aralkyl, S-aralkyl, NH-aralkyl, azido, hydrazino, hydroxylamino, sulfoxide, sulfone, sulfide, disulfide, silyl, a nucleosidic base, an amino acid side chain, or a carbohydrate, comprising:

contacting a purine heterocyclic scaffold having two functionalizable atoms, wherein one of said functionalizable atoms is blocked, with a mixture of at least six different chemical substituents to append said chemical substituents to said heterocyclic scaffold directly to form a substituent-appended scaffold;

deblocking said blocked functionalizable atom of said substituent-appended scaffold; and contacting said substituent-appended scaffold with a mixture ofat least six different chemical sub stituents to append said chemical substituents to said substituent-appended scaffold via a tether moiety covalently attached to one of said functionalizable atoms.

2. The method of claim 1 wherein said compounds of said library are within 20 mole percent of equimolarity.

3. The method of claim 1 wherein said contacting steps are carried out in one reaction vessel.

4. The method of claim 1 wherein said scaffold is contacted with a mixture of at least ten different chemical substituents.

5. The method of claim 1 wherein said scaffold is contacted with a mixture of at least fifteen different chemical substituents.

6. The method of claim 1 wherein said method is performed in solution phase.

7. A method for preparing a library of compounds of the formula:

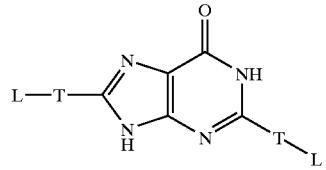

wherein:
each tether moiety T is —NHR$^1$NH—, —NH(R$^1$)O—, —NHR$^2$NH—, —NHR$^2$SO$_2$NH—, —NHR$^1$—, —N(R$^4$)$_2$, —N=N—, O, S, Se, —P(=O)(O)$_2$, NH, OR$^2$, OR$^3$, malonato, pyrrolidinyl, piperidinyl, piperazinyl, morpholino, imidazolyl, pyrrolyl, pyrazolyl, indolyl, 1H-indolyl, α-carbolinyl, carbazolyl, phenothiazinyl, phenoxazinyl, tetrazolyl, or triazolyl;

R$^1$ is alkylene; R$^2$ is aryl; R$^3$ is H or C$_1$–C$_{10}$ alkyl; R$^4$ is alkyleneoxy; and each chemical substituent L is, independently, C$_1$–C$_{10}$ alkyl, substituted C$_1$–C$_{10}$ alkyl, C$_2$–C$_{10}$ alkenyl, substituted C$_2$–C$_{10}$ alkenyl, C$_2$–C$_{10}$ alkynyl, substituted C$_2$–C$_{10}$ alkynyl, C$_4$–C$_7$ carbocyclic alkyl, substituted C$_4$–C$_7$ carbocyclic alkyl, C$_4$–C$_{10}$ alkenyl carbocyclic, substituted C$_4$–C$_{10}$ alkenyl carbocyclic, C$_4$–C$_{10}$ alkynyl carbocyclic, substituted C$_4$–C$_{10}$ alkynyl carbocyclic, C$_6$–C$_{14}$ aryl, substituted C$_6$–C$_{14}$ aryl, heteroaryl, substituted heteroaryl, a nitrogen, oxygen or sulfur containing heterocycle, a substituted nitrogen, oxygen or sulfur containing heterocycle, a mixed heterocycle, or a substituted mixed heterocycle; wherein each of the substituent groups is selected from a group consisting of alkyl, alkenyl, alkynyl, aryl, hydroxyl, alkoxy, benzyl, nitro, thiol, thioalkyl, thioalkoxy and halo; or L is, independently, phthalimido, an ether having 2 to 10 carbon atoms and 1 to 4 oxygen or sulfur atoms, hydrogen, halogen, hydroxyl, thiol, keto, carboxyl, NR$^1$R$^2$, CONR$^1$, amidine, guanidine, glutamyl, nitro, nitrate, nitrile, trifluoromethyl, trifluoromethoxy, NH-alkyl, N-dialkyl, O-aralkyl, S-aralkyl, NR-aralkyl, azido, hydrazino, hydroxylamino, sulfoxide, sulfone, sulfide, disulfide, silyl, a nucleosidic base, an amino acid side chain, or a carbohydrate, comprising:

contacting a purine heterocyclic scaffold having two functionalizable atoms, wherein one of said functionalizable atoms is blocked, with a mixture of at least six different chemical substituents to append said chemical substituents to said heterocyclic scaffold via a tether moiety covalently attached to one of said functionalizable atoms to form a substituent-appended scaffold;

deblocking said blocked functionalizable atom of said substituent-appended scaffold; and contacting said substituent-appended scaffold with a mixture of at least six different chemical substituents to append said chemical substituents to said substituent-appended scaffold via a tether moiety covalently attached to one of said functionalizable atoms.

8. The method of claim 7 wherein said compounds of said library are within 20 mole percent of equimolarity.

9. The method of claim 7 wherein said contacting steps are carried out in one reaction vessel.

10. The method of claim 7 wherein said scaffold is contacted with a mixture of at least ten different chemical substituents.

11. The method of claim 7 wherein said scaffold is contacted with a mixture of at least fifteen different chemical substituents.

12. The method of claim 7 wherein said method is performed in solution phase.

13. A method for preparing a library of compounds of the formula:

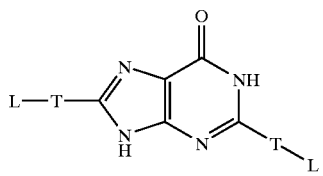

wherein:
each tether moiety T is —NHR$^1$NH—, —NH(R$^1$)O—, —NHR$^2$NH—, —NHR$^2$SO$_2$NH—, —NHR$^1$—, —N(R$^4$)$_2$, —N=N—, O, S, Se, —P(=O)(O)$_2$, NH, OR$^2$, OR$^3$, malonato, pyrrolidinyl, piperidinyl, piperazinyl, morpholino, imidazolyl, pyrrolyl, pyrazolyl, indolyl, 1H-indolyl, α-carbolinyl, carbazolyl, phenothiazinyl, phenoxazinyl, tetrazolyl, or triazolyl;

R$^1$ is alkylene; R$^2$ is aryl; R$^3$ is H or C$_1$–C$_{10}$ alkyl; R$^4$ is alkyleneoxy; and each chemical substituent L is, independently, C$_1$–C$_{10}$ alkyl, substituted C$_1$–C$_{10}$ alkyl, C$_2$–C$_{10}$ alkenyl, substituted C$_2$–C$_{10}$ alkenyl, C$_2$–C$_{10}$ alkynyl, substituted C$_2$–C$_{10}$ alkynyl, C$_4$–C$_7$ carbocyclic alkyl, substituted C$_4$–C$_7$ carbocyclic alkyl, C$_4$–C$_{10}$ alkenyl carbocyclic, substituted C$_4$–C$_{10}$ alkenyl carbocyclic, C$_4$–C$_{10}$ alkynyl carbocyclic, substituted C$_4$–C,0 alkynyl carbocyclic, C$_6$–C$_{14}$ aryl, substituted C$_6$–C$_{14}$ aryl, heteroaryl, substituted heteroaryl, a nitrogen, oxygen or sulfur containing heterocycle, a substituted nitrogen, oxygen or sulfur containing heterocycle, a mixed heterocycle; or a substituted mixed heterocycle; wherein each of the substituent groups is selected from a group consisting of alkyl, alkenyl, alkynyl, aryl, hydroxyl, alkoxy, benzyl, nitro, thiol, thioalkyl, thioalkoxy and halo; or L is, independently, phthalimido, an ether having 2 to 10 carbon atoms and 1 to 4 oxygen or sulfur atoms, hydrogen, halogen, hydroxyl, thiol, keto, carboxyl, NR$^1$R$^2$, CONR$^1$, amidine, guanidine, glutamyl, nitro, nitrate, nitrile, trifluoromethyl, trifluoromethoxy, NH-alkyl, N-dialkyl, O-aralkyl, S-aralkyl, NH-aralkyl, azido, hydrazino, hydroxylamino, sulfoxide, sulfone, sulfide, disulfide, silyl, a nucleosidic base, an amino acid side chain, or a carbohydrate, comprising: contacting a purine heterocyclic scaffold molecule having a plurality of functionalizable atoms with a mixture of at least six different chemical substituents in one reaction vessel to append said chemical substituents to said scaffold via a tether moiety covalently attached to one of said functionalizable atoms.

14. The method of claim 13 wherein said compounds of said library are within 20 mole percent of equimolarity.

15. The method of claim 13 wherein said scaffold is contacted with a mixture of at least ten different chemical substituents.

16. The method of claim 13 wherein said scaffold is contacted with a mixture of at least fifteen different chemical substituents.

17. The method of claim 13 wherein said method is performed in solution phase.

* * * * *

UNITED STATES PATENT AND TRADEMARK OFFICE
CERTIFICATE OF CORRECTION

PATENT NO. : 6,991,902 B2
APPLICATION NO. : 10/087424
DATED : January 31, 2006
INVENTOR(S) : Phillip Dan Cook It is certified that error appears in the above-identified patent and that said Letters Patent is hereby corrected as shown below:

On the title page
1) Title Page:
Item [56], References Cited, OTHER PUBLICATIONS, "Norman" reference, please delete "6430-7431" and insert therefore --7430-7431--;

Column 84, Claim 1, line 16, please delete "ofat" and insert therefore --of at--;

Column 84, Claim 1, line 16, please delete "sub stituents" and insert therefore --substituents--;

Column 86, Claim 13, line 15, please delete "$C_4$-C,0" and insert therefore --$C_4$-$C_{10}$--;

Column 86, Claim 13, line 20, please delete ";" and insert therefore --,--.

Signed and Sealed this

First Day of August, 2006

JON W. DUDAS
*Director of the United States Patent and Trademark Office*